(12) United States Patent
Fujiwara et al.

(10) Patent No.: US 10,754,248 B2
(45) Date of Patent: Aug. 25, 2020

(54) SULFONIUM SALT, RESIST COMPOSITION, AND PATTERNING PROCESS

(71) Applicant: SHIN-ETSU CHEMICAL CO., LTD., Tokyo (JP)

(72) Inventors: Takayuki Fujiwara, Joetsu (JP); Ryo Mitsui, Joetsu (JP); Kazuhiro Katayama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 7 days.

(21) Appl. No.: 15/903,652

(22) Filed: Feb. 23, 2018

(65) Prior Publication Data
US 2018/0275516 A1  Sep. 27, 2018

(30) Foreign Application Priority Data

Mar. 22, 2017 (JP) .................................. 2017-55526

(51) Int. Cl.
*G03F 7/039* (2006.01)
*G03F 7/029* (2006.01)
(Continued)

(52) U.S. Cl.
CPC .............. *G03F 7/039* (2013.01); *C07C 69/00* (2013.01); *C07C 309/12* (2013.01);
(Continued)

(58) Field of Classification Search
CPC ...... G03F 7/039; G03F 7/2059; G03F 7/0397; G03F 7/0045; G03F 7/029; G03F 7/0048;
(Continued)

(56) References Cited

U.S. PATENT DOCUMENTS

2003/0013039 A1  1/2003  Kobayashi et al.
2006/0141383 A1  6/2006  Miyamatsu et al.
(Continued)

FOREIGN PATENT DOCUMENTS

CN      103787923 A      5/2014
JP      2003-066612 A    3/2003
(Continued)

OTHER PUBLICATIONS

"Refractive index" Website Name: Encyclopaedia Britannica Publisher: Encyclopaedia Britannica, Inc. Date Published: Dec. 28, 2018 URL: https://www.britannica.com/science/refractive-index Access Date: Jul. 26, 2019, one page. (Year: 2018).*
(Continued)

*Primary Examiner* — Cynthia Hamilton
(74) *Attorney, Agent, or Firm* — Oliff PLC

(57) ABSTRACT

The present invention provides a sulfonium salt capable of providing a resist composition having few defects in photolithography where a high energy beam is used as a light source, and excellent in lithography performance by controlling acid diffusion.
The present invention was accomplished by a sulfonium salt including an anion and a cation, the cation having a partial structure represented by the following general formula (1), except for a sulfonium salt having a cation represented by the following general formula (1'), (1)

(Continued)

-continued

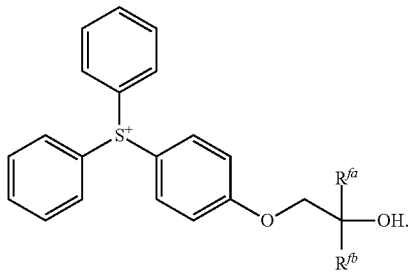

(1')

23 Claims, 1 Drawing Sheet

(51) Int. Cl.
| | |
|---|---|
| C07C 381/12 | (2006.01) |
| G03F 7/004 | (2006.01) |
| C08L 33/06 | (2006.01) |
| C07D 335/02 | (2006.01) |
| C07C 309/20 | (2006.01) |
| C07C 69/00 | (2006.01) |
| C07D 333/46 | (2006.01) |
| C07C 309/12 | (2006.01) |
| G03F 7/20 | (2006.01) |
| C08K 5/098 | (2006.01) |
| C08K 5/42 | (2006.01) |

(52) U.S. Cl.
CPC .......... *C07C 309/20* (2013.01); *C07C 381/12* (2013.01); *C07D 333/46* (2013.01); *C07D 335/02* (2013.01); *C08L 33/06* (2013.01); *G03F 7/0045* (2013.01); *G03F 7/0048* (2013.01); *G03F 7/029* (2013.01); *G03F 7/0397* (2013.01); *G03F 7/2041* (2013.01); *C07C 2603/74* (2017.05); *C08K 5/098* (2013.01); *C08K 5/42* (2013.01); *G03F 7/2059* (2013.01)

(58) Field of Classification Search
CPC ..... C07C 69/00; C07C 309/20; C07C 309/12; C07C 381/12; C07C 2603/74; C07D 335/02; C07D 333/46; C08L 33/06; C08K 5/42; C08K 5/098
See application file for complete search history.

(56) References Cited

U.S. PATENT DOCUMENTS

| | | |
|---|---|---|
| 2007/0231738 A1 | 10/2007 | Kaneko et al. |
| 2008/0085469 A1 | 4/2008 | Ohsawa et al. |
| 2008/0090172 A1 | 4/2008 | Hatakeyama et al. |
| 2008/0090173 A1 | 4/2008 | Harada et al. |
| 2008/0118860 A1 | 5/2008 | Harada et al. |
| 2008/0153030 A1 | 6/2008 | Kobayashi et al. |
| 2008/0318160 A1 | 12/2008 | Ohsawa et al. |
| 2009/0081588 A1 | 3/2009 | Hatakeyama et al. |
| 2009/0111047 A1 | 4/2009 | Yamashita |
| 2009/0208867 A1 | 8/2009 | Harada et al. |
| 2009/0208873 A1 | 8/2009 | Harada et al. |
| 2009/0246694 A1 | 10/2009 | Ohsawa et al. |
| 2009/0274978 A1 | 11/2009 | Ohashi et al. |
| 2009/0280434 A1 | 11/2009 | Harada et al. |
| 2010/0035185 A1 | 2/2010 | Hagiwara et al. |
| 2010/0055608 A1 | 3/2010 | Ohashi et al. |
| 2010/0099042 A1 | 4/2010 | Ohashi et al. |
| 2010/0112482 A1 | 5/2010 | Watanabe et al. |
| 2010/0119970 A1 | 5/2010 | Ohsawa et al. |
| 2010/0136482 A1 | 6/2010 | Harada et al. |
| 2010/0143830 A1 | 6/2010 | Ohashi et al. |
| 2010/0209827 A1 | 8/2010 | Ohashi et al. |
| 2010/0266957 A1 | 10/2010 | Harada et al. |
| 2011/0008735 A1 | 1/2011 | Ohsawa et al. |
| 2011/0236826 A1 | 9/2011 | Hatakeyama et al. |
| 2012/0045724 A1 | 2/2012 | Ohsawa et al. |
| 2012/0100486 A1 | 4/2012 | Sagehashi et al. |
| 2012/0214100 A1* | 8/2012 | Kobayashi ............ G03F 7/0045 430/285.1 |
| 2012/0225386 A1 | 9/2012 | Watanabe et al. |
| 2013/0224657 A1 | 8/2013 | Ohashi et al. |
| 2013/0337378 A1 | 12/2013 | Ohashi et al. |
| 2014/0114080 A1 | 4/2014 | Sagehashi et al. |
| 2014/0120471 A1 | 5/2014 | Aqad et al. |
| 2014/0199629 A1 | 7/2014 | Ohashi et al. |
| 2014/0248562 A1 | 9/2014 | Shibuya et al. |
| 2014/0272707 A1 | 9/2014 | Fukushima et al. |
| 2014/0322650 A1 | 10/2014 | Ohashi et al. |
| 2015/0253666 A1 | 9/2015 | Hatakeyama et al. |
| 2015/0323865 A1 | 11/2015 | Sagehashi et al. |
| 2016/0004155 A1 | 1/2016 | Ohashi et al. |
| 2016/0152755 A1 | 6/2016 | Fujiwara et al. |
| 2017/0226252 A1* | 8/2017 | Sagehashi ............ C08F 222/20 |
| 2018/0059543 A1* | 3/2018 | Mitsui .................. C07D 327/08 |
| 2019/0010119 A1* | 1/2019 | Suzuki .................. C07C 309/25 |

FOREIGN PATENT DOCUMENTS

| | | |
|---|---|---|
| JP | 3760952 B2 | 3/2006 |
| JP | 3790649 B2 | 6/2006 |
| JP | 2007-145797 A | 6/2007 |
| JP | 2007-297590 A | 11/2007 |
| JP | 4025039 B2 | 12/2007 |
| JP | 2008-088343 A | 4/2008 |
| JP | 2008-106045 A | 5/2008 |
| JP | 2008-111103 A | 5/2008 |
| JP | 2008-122932 A | 5/2008 |
| JP | 2008-158339 A | 7/2008 |
| JP | 2009-007327 A | 1/2009 |
| JP | 2009-098638 A | 5/2009 |
| JP | 2009-109595 A | 5/2009 |
| JP | 2009-191151 A | 8/2009 |
| JP | 2009-192784 A | 8/2009 |
| JP | 2009-258695 A | 11/2009 |
| JP | 2009-269953 A | 11/2009 |
| JP | 2009-276363 A | 11/2009 |
| JP | 2010-077404 A | 4/2010 |
| JP | 2010-107695 A | 5/2010 |
| JP | 2010-113209 A | 5/2010 |
| JP | 2010-116550 A | 5/2010 |
| JP | 2010-134012 A | 6/2010 |
| JP | 2010-155824 A | 7/2010 |
| JP | 2010-215608 A | 9/2010 |
| JP | 2010-250105 A | 11/2010 |
| JP | 2011-016746 A | 1/2011 |
| JP | 4621806 B2 | 1/2011 |
| JP | 2011-042789 A | 3/2011 |
| JP | 2011-221513 A | 11/2011 |
| JP | 2011-231312 A | 11/2011 |
| JP | 2012-041320 A | 3/2012 |
| JP | 2012-046501 A | 3/2012 |
| JP | 2012-106986 A | 6/2012 |
| JP | 2012-153644 A | 8/2012 |
| JP | 2012-181306 A | 9/2012 |
| JP | 2013-209360 A | 10/2013 |
| JP | 2014-001259 A | 1/2014 |
| JP | 2014-006491 A | 1/2014 |
| JP | 2014-122204 A | 7/2014 |
| JP | 2014-133723 A | 7/2014 |
| JP | 2014-166983 A | 9/2014 |
| JP | 2014-177407 A | 9/2014 |
| JP | 2014-225005 A | 12/2014 |
| JP | 2015-166833 A | 9/2015 |
| JP | 2015-180748 A | 10/2015 |
| JP | 2015-214634 A | 12/2015 |
| JP | 2016-018007 A | 2/2016 |

(56) References Cited

FOREIGN PATENT DOCUMENTS

| JP | 2018-035096 A | | 3/2018 | | |
|---|---|---|---|---|---|
| JP | 2019015802 A | * | 1/2019 | ……… | G03F 7/0046 |
| TW | 201245880 A | | 11/2012 | | |
| TW | 201616222 A | | 5/2016 | | |

OTHER PUBLICATIONS

English translation of JP 2014-122204 A, as generated Apr. 26, 2019, from JPTO and INPIT website, 24 pages. (Year: 2019).*
Partial machine generated English translation of Japanese Application No. 2017-131534 obtained from Global Dossier website with note that this Japanese application was published as JP 2019-0158802 A, obained Feb. 1, 2020, 90 pages. (Year: 2020).*
English translation generated machine of the description of Japanese Application No. 2017-131534 Translation of description text only obtained from Espacenet patent search for jp 2017131534 on Feb. 1, 2020, 27 pages. (Year: 2020).*
Nov. 12, 2019 Office Action issued in Japanese Patent Application No. 2017-055526.
Nov. 1, 2019 Office Action issued in Chinese Patent Application No. 201810234145.6.

* cited by examiner

PHOTORESIST COATING

PHOTORESIST EXPOSURE

ORGANIC SOLVENT DEVELOPMENT

SULFONIUM SALT, RESIST COMPOSITION, AND PATTERNING PROCESS

TECHNICAL FIELD

The present invention relates to a sulfonium salt having a specific partial structure, a resist composition containing the sulfonium salt, and a patterning process using the resist composition.

BACKGROUND

Recent higher integration and speed of LSI integrated circuits has required more advanced micropatterning in patterning conditions and thus high-resolution resist patterns. In addition to lithography characteristics such as pattern shapes, contrast, mask error enhancement factor (MEEF), and roughness in particular, the improvement in defects (surface defect) of developed resist patterns has been more increasingly urgent than conventionally required. Such defects are known as faults detected with surface defect viewing instrument ("KLA", Product from KLA-Tencor Corporation) that observes developed resist patterns from the above, such as scum, bubbles, dust, and bridges between resist patterns in developed resist patterns. The resulting defects are partially attributed to low solubility to a cast solvent in a resist composition such as a photo acid generator and residual defects after the use of a developer.

One common means for reducing defects caused by the use of a photo acid generator is to improve the solubility to a developer and a resist solvent by modification from a photo acid generator. The improvement in solubility to an organic solvent may require introduction of a linear alkyl group, a fluorine atom and others, while the alkaline developer solubility can be improved by introducing a polar group such as a hydroxy group. A known effective method for improving the solubility to a solvent is to introduce a hexafluoroalcohol unit, e.g., those having excellent compatibility in the following sulfonium cation illustrated in Patent Documents 1 and 2. As a resist composition, the use of the photo acid generators disclosed in these documents can certainly reduce defects, but it is very hard to obtain satisfactory lithography performance due to swelling and increasing acid diffusion length. Likewise, anion modification is expected to improve the compatibility, while the resulting acid diffusion promotion can degrade lithography performance,

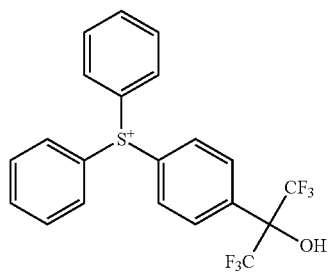 [SMILES: OC(c1ccc([S+](c2ccccc2)c2ccccc2)cc1)(C(F)(F)F)C(F)(F)F]

PRIOR ART DOCUMENTS

Patent Documents

Patent Document 1: JP-B-4621806
Patent Document 2: JP-A-2014-122204

SUMMARY OF THE INVENTION

Problem to be Solved by the Invention

Amid growing recent demands for high-resolution resist patterns, it is hard to satisfy both defect reduction and stable lithography performance in a resist composition using a conventional photo acid generator. The introduction of a fluorine atom or an alkyl group is effective in defect reduction, but this approach unfortunately fails to control acid diffusion and thus obtain a satisfactory lithography performance such as mask error factor (MEF), exposure latitude (EL), line width roughness (LWR), and critical dimension uniformity (CDU).

The present invention was made in view of the situation to solve the problems, and has an object to provide a sulfonium salt capable of providing a resist composition having few defects by its use as a photo acid generator in photolithography where a high energy beam is used as a light source, and excellent in lithography performance by controlling acid diffusion, a resist composition containing the sulfonium salt, and a patterning process using the resist composition.

Means for Solving the Problem

To solve these problems, the present invention provides a sulfonium salt including an anion and a cation, the cation having a partial structure represented by the following general formula (1),

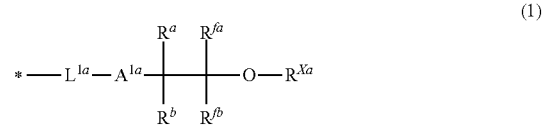

(1)

wherein, each of $R^{fa}$ and $R^{fb}$ independently represents a fluoroalkyl group having 1 to 4 carbon atoms; $R^{Xa}$ represents a hydrogen atom or an acid labile group; each of $R^a$ and $R^b$ independently represents a hydrogen atom, or a monovalent hydrocarbon group having 1 to 10 carbon atoms optionally containing a heteroatom, $R^a$ and $R^b$ may be bonded to form a ring together with a carbon atom bonded thereto; A1a represents an ether bond or a thioether bond; $L^{1a}$ represents a single bond, or a divalent linking group having 1 to 20 carbon atoms optionally containing a heteroatom; "*" represents a bond, and the sulfonium salt doesn't correspond to a sulfonium salt having a cation represented by the following general formula (1'),

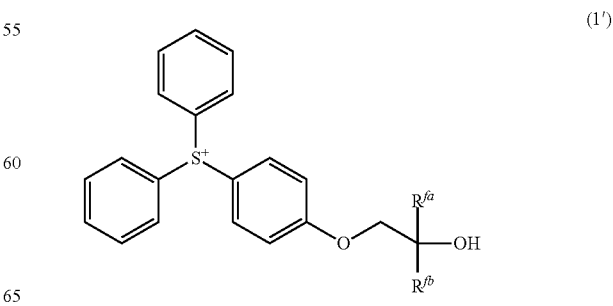

(1')

wherein, $R^{fa}$ and $R^{fb}$ represent the same meanings as before.

The sulfonium salt thus obtained may be a sulfonium salt capable of providing a resist composition having few defects by its use as a photo acid generator in photolithography where a high energy beam is used as a light source, and excellent in lithography performance by controlling acid diffusion.

Preferably, the sulfonium salt is represented by the following general formula (2),

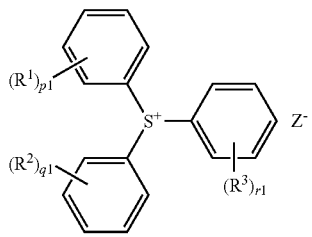

(2)

wherein, each of $R^1$, $R^2$, and $R^3$ independently represents any of a hydrogen atom, a partial structure represented by the general formula (1), a linear, a branched, or a cyclic monovalent hydrocarbon group having 1 to 20 carbon atoms optionally containing a heteroatom, or direct binding with an adjacent benzene ring; each of "p1", "q1", and "r1" independently represents an integer of 0 to 5, and when "p1", "q1", or "r1" represents 2 or more, a plurality of $R^1$s, $R^2$s, or $R^3$s corresponding thereto may be the same or different, when p1+q1+r1 represents 2 or more, a plurality of $R^1$s, $R^2$s, or $R^3$s may be bonded to form a ring together with a carbon atom on a benzene ring bonded thereto, and $R^1$ and $R^2$, $R^1$ and $R^3$, or $R^2$ and $R^3$ may be bonded to form a ring together with two benzene rings bonded thereto and a sulfur atom in the formula; one or more of $R^1$, $R^2$, and $R^3$ represent a partial structure represented by the general formula (1), "*" in the general formula (1) represents a bond with a benzene ring; and $Z^-$ represents a monovalent anion.

Such a sulfonium salt can further improve the lithography performance of a resist composition.

Also, $R^{Xa}$ in the general formula (1) preferably represents an acid labile group.

When $R^{Xa}$ is an acid labile group, the dissolution contrast of a resist composition can be improved.

Preferably, $R^{fa}$ and $R^{fb}$ in the general formula (1) represent a trifluoromethyl group, and $R^a$ and $R^b$ represent a hydrogen atom.

When each of $R^{fa}$ and $R^{fb}$ represents a trifluoromethyl group, the sulfonium salt can readily be synthesized, and the compatibility of a resist composition and lithography performance such as LWR can further be improved. When each of $R^a$ and $R^b$ represents a hydrogen atom, the sulfonium salt can readily be synthesized, and the compatibility of a resist composition and lithography performance such as MEF can further be improved.

Preferably, $L^{1a}$ in the general formula (1) represents a single bond.

When $L^{1a}$ represents a single bond, the sulfonium salt can readily be synthesized, and the effect of controlling acid diffusion can further be improved.

Preferably, $A^{1a}$ in the general formula (1) represents an ether bond.

When $A^{1a}$ represents an ether bond, the lithography performance of a resist composition can further be improved. When $L^{1a}$ represents a single bond and a partial structure represented by the general formula (1) directly bonds with a benzene ring via the ether bond $A^{1a}$, the storage stability of a resist composition can be improved.

Preferably, the anion is represented by the following general formula (3),

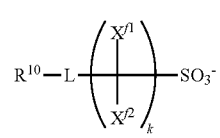

(3)

wherein, $R^{10}$ represents a linear, a branched, or a cyclic monovalent hydrocarbon group having 1 to 40 carbon atoms optionally containing a heteroatom; "L" represents a single bond or a divalent linking group; each of $X^{f1}$ and $X^{f2}$ independently represents a hydrogen atom, a fluorine atom, or an alkyl group substituted by one or more fluorine atoms; and "k" represents an integer of 0 to 4.

Such an anion can further improve the lithography performance of a resist composition.

Preferably, the anion is represented by the following general formula (4a), (4b), or (4c),

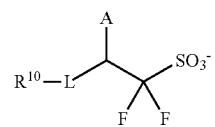

(4a)

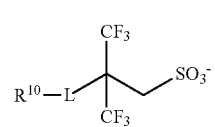

(4b)

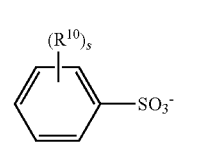

(4c)

wherein, $R^{10}$ represents a linear, a branched, or a cyclic monovalent hydrocarbon group having 1 to 40 carbon atoms optionally containing a heteroatom; "L" represents a single bond or a divalent linking group; "A" represents a hydrogen atom or a trifluoromethyl group; and "s" represents an integer of 0 to 5.

Such an anion can further improve the lithography performance of a resist composition.

Also, the present invention provides a resist composition including:
(A) the sulfonium salt;
(B) a base resin; and
(C) an organic solvent.

The resist composition thus obtained has few defects in photolithography where a high energy beam is used as a light source, and is excellent in lithography performance by controlling acid diffusion.

Preferably, the resist composition further includes one or more selected from:
(D) a photo acid generator other than the component (A);
(E) a quencher; and
(F) a surfactant.

The resist composition of the present invention, in addition to the components (A) to (C), as required, can include one or more selected from the components (D) to (F).

In addition, the component (B) is preferably a polymer including a repeating unit represented by the following general formula (6) and a repeating unit represented by the following general formula (7),

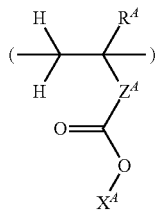

(6)

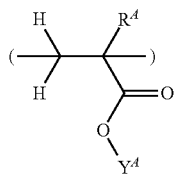

(7)

wherein, $R^A$ represents any of a hydrogen atom, a fluorine atom, a methyl group, or a trifluoromethyl group; $Z^A$ represents any of a single bond, a phenylene group, a naphthylene group, or a (main chain) —C(=O)—O—Z'—; Z' represents a linear, a branched, or a cyclic alkylene group having 1 to 10 carbon atoms optionally containing any of a hydroxy group, an ether bond, an ester bond, or a lactone ring, a phenylene group, or a naphthylene group; $X^A$ represents an acid labile group; and $Y^A$ represents a hydrogen atom, or a polar group having one or more structures selected from a hydroxy group, a cyano group, a carbonyl group, a carboxyl group, an ether bond, an ester bond, a sulfonic ester bond, a carbonate bond, a lactone ring, a sultone ring, and a carboxylic acid anhydride.

Such the resist composition including a component (B) provides high dissolution contrast, excellent lithography performance such as LWR, few defects and excellently rectangle patterns.

Also, $X^A$ in the general formula (6) is preferably represented by any of the following general formula (6a), (6b), or (6c),

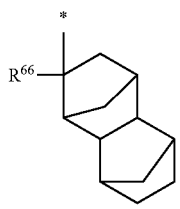

(6a)

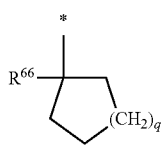

(6b)

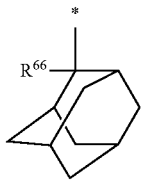

(6c)

wherein, $R^{66}$ represents a linear, a branched, or a cyclic monovalent hydrocarbon group having 1 to 10 carbon atoms optionally containing a heteroatom; "q" represents 1 or 2; and "*" represents a bond with an ester site in the general formula (6).

Such the resist composition including a component (B) provides extremely high dissolution contrast, excellent lithography performance such as LWR, few defects and excellently rectangle patterns.

$Z^A$ in the general formula (6) preferably represents a single bond.

Such the resist composition including a component (B) is more excellent in dissolution contrast and pattern's rectangle property.

In addition, the component (D) is preferably represented by the following general formula (8) or the following general formula (9),

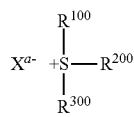

(8)

wherein, each of $R^{100}$, $R^{200}$, and $R^{300}$ independently represents a linear, a branched, or a cyclic monovalent hydrocarbon group having 1 to 20 carbon atoms optionally containing a heteroatom, and two or more of $R^{100}$, $R^{200}$, and $R^{300}$ may be bonded to form a ring together with a sulfur atom in the formula; and $X^{a-}$ represents an anion represented by any of the following general formula (8A), (8B), (8C) or (8D),

(8A)

(8B)

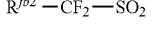

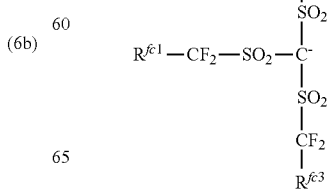

(8C)

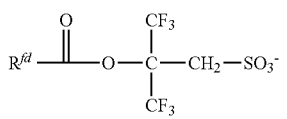

wherein, each of $R^{fb1}$, $R^{fb2}$, $R^{fc1}$, $R^{fc2}$, and $R^{fc3}$ independently represents a fluorine atom, or a linear, a branched, or a cyclic monovalent hydrocarbon group having 1 to 40 carbon atoms optionally containing a heteroatom; $R^{fb1}$ and $R^{fb2}$, and $R^{fc1}$ and $R^{fc2}$ may be bonded to form a ring together with a carbon atom bonded thereto and an atom therebetween; and $R^{fd}$ represents a linear, a branched, or a cyclic monovalent hydrocarbon group having 1 to 40 carbon atoms optionally containing a heteroatom,

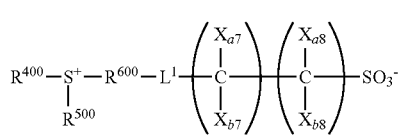

wherein, each of $R^{400}$ and $R^{500}$ independently represents a linear, a branched, or a cyclic monovalent hydrocarbon group having 1 to 30 carbon atoms optionally containing a heteroatom; $R^{600}$ represents a linear, a branched, or a cyclic divalent hydrocarbon group having 1 to 30 carbon atoms optionally containing a heteroatom; two or more of $R^{400}$, $R^{500}$, and $R^{600}$ may be bonded to form a ring together with a sulfur atom in the formula; $L^1$ represents a single bond, an ether bond, or a linear, a branched, or a cyclic divalent hydrocarbon group having 1 to 20 carbon atoms optionally containing a heteroatom; each of $X_{a7}$, $X_{b7}$, $X_{a8}$, and $X_{b8}$ independently represents any of a hydrogen atom, a fluorine atom, or a trifluoromethyl group; one or more of $X_{a7}$, $X_{b7}$, $X_{a8}$, and $X_{b8}$ represent a fluorine atom or a trifluoromethyl group.

In such a resist composition including a component (D), acid diffusion is more controlled and lithography performance is further improved.

Preferably, the component (E) includes an amine compound or a compound represented by the following general formula (10) or the following general formula (11),

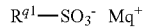

wherein, $R^{q1}$ represents a hydrogen atom, or a linear, a branched, or a cyclic monovalent hydrocarbon group having 1 to 40 carbon atoms optionally containing a heteroatom, except for cases where a hydrogen atom on a carbon atom at a-position of a sulfo group is substituted by a fluorine atom or a fluoroalkyl group when $R^{q1}$ represents a monovalent hydrocarbon group; $R^{q2}$ represents a hydrogen atom, or a linear, a branched, or a cyclic monovalent hydrocarbon group having 1 to 40 carbon atoms optionally containing a heteroatom; and $Mq^+$ represents an onium cation.

In such a resist composition including a component (E), acid diffusion is more controlled and lithography performance is further improved.

In addition, the component (F) is preferably a surfactant that is insoluble or poorly soluble in water and soluble in an alkaline developer, or a surfactant that is insoluble or poorly soluble in water and an alkaline developer.

Such a resist composition including a component (F) contained not only improves the coating property, but also controls the elution of water-soluble components from a resist film.

Preferably, the resist composition is a chemically amplified resist composition.

Such a chemically amplified resist composition is more excellent in resolution.

In addition, the present invention provides a patterning process, including applying the resist composition to a substrate; exposing the composition with any of a high energy beam with a wavelength of 140 to 250 nm, an electron beam, or EUV via a photo mask after heating the composition before exposure; and developing the composition with a developer after heating the composition after exposure.

The patterning process thus obtained can readily form an excellently rectangle fine pattern having few defects.

Also, in the patterning process of the present invention, an alkaline aqueous solution is used as the developer to obtain a positive pattern in which an exposed area is dissolved and a non-exposed area is not dissolved.

Also, in the patterning process of the present invention, an organic solvent is used as the developer to obtain a negative pattern in which a non-exposed area is dissolved and an exposed area is not dissolved.

Preferably, the developer comprises one or more organic solvents selected from the group consisting of 2-octanone, 2-nonanone, 2-heptanone, 3-heptanone, 4-heptanone, 2-hexanone, 3-hexanone, disobutyl ketone, methyl cyclohexanone, acetophenone, methylacetophenone, propyl acetate, butyl acetate, isobutyl acetate, amyl acetate, butenyl acetate, isoamyl acetate, propyl formate, butyl formate, isobutyl formate, amyl formate, isoamyl formate, methyl valerate, methyl pentenoate, methyl crotonate, ethyl crotonate, methyl propionate, ethyl propionate, ethyl 3-ethoxy propionate, methyl lactate, ethyl lactate, propyl lactate, butyl lactate, isobuthyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

When an organic solvent is used for development in the patterning process of the present invention, these organic solvents can desirably be used as a developer.

In the step of exposure, a liquid with a refractive index of 1.0 or more is preferably mediated between an applied resist film and a projection lens for liquid immersion exposure.

Such liquid immersion exposure can further form micropatterns.

Preferably, a top coat is further formed on the applied resist film, and the liquid is mediated between the top coat and the projection lens for liquid immersion exposure.

Such a top coat is formed to prevent eluate coming out of a resist film and enhance the water-sliding property of the film surface.

Effect of the Invention

As described above, the sulfonium salt of the present invention can provide a chemically amplified resist composition having few defects in photolithography where a high energy beam such as KrF and ArF excimer laser lights, electron beam (EB), and extreme ultraviolet rays (EUV) is used as a light source, and excellent in lithography performance such as MEF, EL, LWR, and CDU by controlling acid diffusion. By using a resist composition including the sulfonium salt, excellently rectangle micropatterns having few defects can readily be formed.

DESCRIPTION OF THE PREFERRED EMBODIMENTS

Figure 1A:
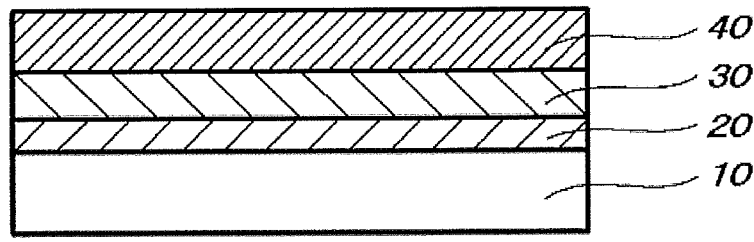
FIG. 1(A) is a cross-sectional view of a photoresist film formed on a substrate for illustrating one example of the patterning process of the present invention.

As described above, the development of a photo acid generator capable of providing a resist composition having few defects in photolithography where a high energy beam is used as a light source, and excellent in lithography performance by controlling acid diffusion has been demanded.

Inventors of the present invention have carried out an extended investigation and found that a resist composition using a sulfonium salt having a specific partial structure including a fluoroalcohol unit in a cation as a photo acid generator is effective in precise microprocessing as a resist composition having few defects, and excellent in lithography performance such as MEF, EL, LWR, and CDU by controlling acid diffusion. Based on that information, the present invention was accomplished.

Specifically, the present invention provides a sulfonium salt including an anion and a cation, wherein the cation has a partial structure represented by the following general formula (1),

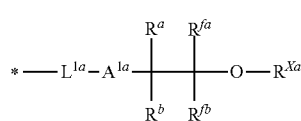

(1)

wherein, each of $R^{fa}$ and $R^{fb}$ independently represents a fluoroalkyl group having 1 to 4 carbon atoms; $R^{Xa}$ represents a hydrogen atom or an acid labile group; each of $R^a$ and $R^b$ independently represents a hydrogen atom, or a monovalent hydrocarbon group having 1 to 10 carbon atoms optionally containing a heteroatom, $R^a$ and $R^b$ may be bonded to form a ring together with a carbon atom bonded thereto; $A^{1a}$ represents an ether bond or a thioether bond; $L^{1a}$ represents a single bond, or a divalent linking group having 1 to 20 carbon atoms optionally containing a heteroatom; "*" represents a bond, and the sulfonium salt doesn't correspond to a sulfonium salt having a cation represented by the following general formula (1'),

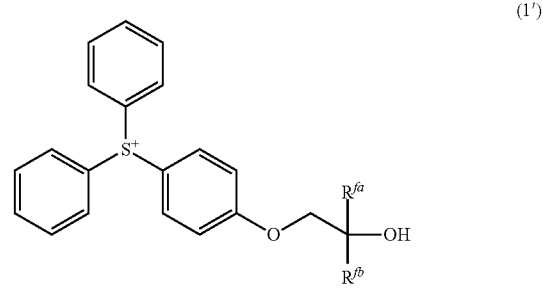

(1')

wherein, $R^{fa}$ and $R^{fb}$ represent the same meanings as before.

The present invention will be described in detail, but the present invention is not restricted thereto. Herein, in cases where some structures represented by a chemical formula include an asymmetric carbon and also enantiomers and diastereomers, such isomers are represented by one formula. These isomers may be used singularly or mixed in combination therewith as a mixture. Herein, "Me" refers to a methyl group, "Ac" an acetyl group, "nBn" an n-butyl group, "tBu" a tert-butyl group, and "Ts" a tosyl group.

[Sulfonium Salt]

The sulfonium salt of the present invention has a partial structure represented by the general formula (1) in a cation, except for a sulfonium salt having a cation represented by the general formula (1').

Each of $R^{fa}$ and $R^{fb}$ in the general formula (1) independently represents a fluoroalkyl group having 1 to 4 carbon atoms (alkyl fluoride group). Illustrative example thereof includes a trifluoromethyl group, pentafluoroethyl group, heptafluoropropyl group, and nonafluorobutyl group. $R^{fa}$ and $R^{fb}$ preferably represent a trifluoromethyl group. When each of $R^{fa}$ and $R^{fb}$ represents a trifluoromethyl group, since the sulfonium salt can readily be synthesized and the compatibility is high, the sulfonium salt is uniformly dispersed in a resist film to improve lithography performance such as LWR. The $R^{fa}$ and $R^{fb}$ in the general formula (1') represent the same groups as the $R^{fa}$ and $R^{fb}$ in the general formula (1), respectively.

Each of $R^a$ and $R^b$ in the general formula (1) independently represents a hydrogen atom, or a monovalent hydrocarbon group having 1 to 10 carbon atoms optionally containing a heteroatom. $R^a$ and $R^b$ may be bonded to form a ring together with a carbon atom bonded thereto. Illustrative example of the monovalent hydrocarbon group includes a methyl group, an ethyl group, a propyl group, an isopropyl group, an n-butyl group, an n-pentyl group, an n-hexyl group, an n-octyl group, an n-nonyl group, an n-decyl group, a cyclopentyl group, a cyclohexyl group, and an adamantyl group. Part of a hydrogen atom in these groups may be substituted by a heteroatom such as an oxygen atom, a sulfur atom, a nitrogen atom, and a halogen atom, or mediated by a heteroatom. Accordingly, a hydroxy group, a cyano group, a carbonyl group, an ether bond, an ester bond, a sulfonic ester bond, a carbonate bond, a lactone ring, a sultone ring, a carboxylic acid anhydride, and a haloalkyl group may be formed or mediated. Each of $R^a$ and $R^b$ preferably represents a hydrogen atom or a methyl group. When each of $R^a$ and $R^b$ represents a hydrogen atom or a methyl group, the sulfonium salt can readily be synthesized and the compatibility is high. In addition, there are few three-dimensional obstacles, resulting in smooth five-membered ring conformation in the effect of controlling acid diffusion by later-described two ether bonds. The resulting high ability to control acid diffusion can improve lithography performance such as MEF.

Ala in the general formula (1) represents an ether bond (—O—) or a thioether bond (—S—). Ala preferably represents an ether bond. When Ala represents an ether bond, a proton is effectively complemented from a lone pair on a highly basic oxygen atom to provide the effect of controlling acid diffusion due to the later-described five-membered ring conformation and improve lithography performance. In addition, when $L^{1a}$ represents a single bond and a partial structure represented by the general formula (1) directly bonds with a benzene ring via an ether bond $A^{1a}$, a sulfonium cation is stabilized due to resonance effect from a lone pair of an oxygen atom to improve the storage stability of a resist composition.

$R^{Xa}$ in the general formula (1) represents a hydrogen atom or an acid labile group. Illustrative example of the acid labile group includes an acetal such as a methoxy methyl group, an ethoxyethyl group, a tetrahydropyranyl group, a 1-methoxy-2-methylpropyl group; a tertiary ether such as a tert-butyl group, a tert-amyl group, a 1-methylcyclopentyl group, a 1-ethylcyclopentyl group, a 1-methylcyclohexyl group, and a 1-ethylcyclohexyl group; silyl ether such as a trimethylsilyl group, a triethylsilyl group, a triisopropylsilyl group, and a tert-butyldimethylsilyl group; and a alkoxycarbonyl group such as a tert-butoxycarbonyl group and a tert-amyloxycarbonyl group. When $R^{Xa}$ represents an acid labile group, the $R^{Xa}$ is decomposed due to generated acid after exposure to turn into a hydrogen atom, i.e. to generate a hydroxy group as a polar unit to improve the contrast. When $R^{Xa}$ represents a hydrogen atom, a fluoroalcohol unit having high compatibility such as hexafluoroalcohol unit is generated, which is effective in defect reduction. $R^{Xa}$ preferably represents a hydrogen atom or a methoxy methyl group. When $R^{Xa}$ represents a hydrogen atom or a methoxy methyl group, the sulfonium salt can readily be synthesized, the compatibility is excellent and acid diffusion is controlled from a hydroxy group or an ether bond to improve the lithography performance.

$L^{1a}$ in the general formula (1) represents a single bond, or a divalent linking group having 1 to 20 carbon atoms optionally containing a heteroatom. Illustrative example of the divalent linking group includes a linear alkanediyl group such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group, and a heptadecane-1,17-diyl group; a saturated cyclic hydrocarbon group such as a cyclopentanediyl group, a cyclohexanediyl group, a norbornanediyl group, and an adamantanediyl group; and an unsaturated cyclic hydrocarbon group such as a phenylene group and a naphthylene group. Part of hydrogen atoms of these groups may be substituted by an alkyl group such as a methyl group, an ethyl group, a propyl group, an n-butyl group, and a t-butyl group. Part of hydrogen atoms of these groups may be substituted by a heteroatom-containing group such as an oxygen atom, a sulfur atom, a nitrogen atom, and a halogen atom. A heteroatom-containing group such as an oxygen atom, a sulfur atom, and a nitrogen atom may be mediated between carbon atoms of part of these groups. As a result, part of hydrogen atoms of these groups may include a hydroxy group, a cyano group, a carbonyl group, an ether bond, an ester bond, a sulfonic ester bond, a carbonate bond, a lactone ring, a sultone ring, a carboxylic acid anhydride, or a haloalkyl group. An $L^{1a}$ portion, which can be replaced with one of the above illustrated various linking groups to adjust the solvent solubility, is preferably a single bond. When $L^{1a}$ represents a single bond, the sulfonium salt can readily be synthesized, and the resulting shorter chain portion can control the motion of the sulfonium salt in the resist film, improving the effect of controlling acid diffusion.

The sulfonium salt having a partial structure represented by the general formula (1) in a cation is preferably a sulfonium salt represented by the following general formula (2),

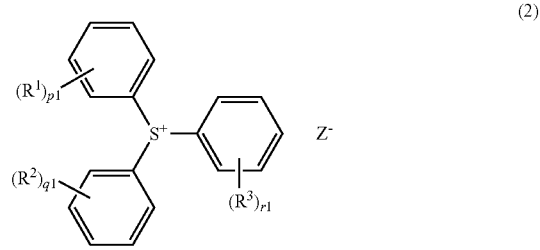

wherein, each of $R^1$, $R^2$, and $R^3$ independently represents any of a hydrogen atom, a partial structure represented by the general formula (1), a linear, a branched, or a cyclic monovalent hydrocarbon group having 1 to 20 carbon atoms optionally containing a heteroatom, or direct binding with an adjacent benzene ring; each of "p1", "q1", and "r1" independently represents an integer of 0 to 5, and when "p1", "q1", or "r1" represents 2 or more, a plurality of $R^1$s, $R^2$s, or $R^3$s corresponding thereto may be the same or different, when p1+q1+r1 represents 2 or more, a plurality of $R^1$s, $R^2$s, or $R^3$s may be bonded to form a ring together with a carbon atom on a benzene ring bonded thereto, and $R^1$ and $R^2$, $R^1$ and $R^3$, or $R^2$ and $R^3$ may be bonded to form a ring together with two benzene rings bonded thereto and a sulfur atom in the formula, one or more of $R^1$, $R^2$, and $R^3$ represent a partial structure represented by the general formula (1); "*" in the general formula (1) represents a bond with a benzene ring; and $Z^-$ represents a monovalent anion.

Each of $R^1$, $R^2$, and $R^3$ in the general formula (2) independently represents any of a hydrogen atom, a partial structure represented by the general formula (1), a linear, a branched, or a cyclic monovalent hydrocarbon group having 1 to 20 carbon atoms optionally containing a heteroatom, or a direct binding with an adjacent benzene ring. One or more of $R^1$, $R^2$, and $R^3$ represent a partial structure represented by the general formula (1), and "*" in the general formula (1) represents a bond with a benzene ring. Illustrative example of the monovalent hydrocarbon group includes an alkyl group, an alkenyl group, an aryl group, an aralkyl group, and an aryloxoalkyl group. Illustrative example of the alkyl group includes a methyl group, an ethyl group, a propyl group, an isopropyl group, a n-butyl group, a sec-butyl group, a tert-butyl group, a tert-amyl group, a n-pentyl group, a n-hexyl group, a n-octyl group, a n-nonyl group, a n-decyl group, a cyclopentyl group, a cyclohexyl group, a 2-ethylhexyl group, a cyclopentylmethyl group, a cyclopentylethyl group, a cyclopentylbutyl group, a cyclohexylmethyl group, a cyclohexylethyl group, a cyclohexylbutyl group, a norbornyl group, a tricyclo[5.2.1.0$^{2,6}$]decanyl group, an adamantyl group, and an adamantylmethyl group. Illustrative example of the alkenyl group includes a vinyl group, an aryl group, a propenyl group, a butenyl group, a hexenyl group, and a cyclohexenyl group. Illustrative example of the aryl group includes an alkoxyphenyl group such as a phenyl group, a naphthyl group, a thienyl group, a 4-hydroxyphenyl group, a 4-methoxyphenyl group, a 3-methoxyphenyl group, a 2-methoxyphenyl group, a 4-ethoxyphenyl group, a 4-tert-butoxyphenyl group, and a 3-tert-butoxyphenyl group; an alkylphenyl group such as a 2-methylphenyl group, a 3-methylphenyl group, a 4-methylphenyl group, a 4-ethylphenyl group, a 4-tert-butylphenyl group, a 4-n-butylphenyl group, a 2,4-dimethylphenyl group, and a 2,4,6-triisopropylphenyl; an alkylnaphthyl group such as a methylnaphthyl group and an ethylnaphthyl group; an alkoxynaphthyl group such as a methoxynaphthyl group, an ethoxynaphthyl group, a n-propoxynaphthyl group, and a n-butoxynaphthyl group; a dialkylnaphthyl group such as a dimethylnaphthyl group and a diethylnaphthyl group; and a dialkoxynaphthyl group such as a dimethoxynaphthyl group and a diethoxynaphthyl group. Illustrative example of the aralkyl group includes a benzyl group, a 1-phenylethyl group, and a 2-phenylethyl group. Illustrative example of the aryloxoalkyl group includes a 2-aryl-2-oxoethyl group such as a 2-phenyl-2-oxoethyl group, a 2-(1-naphthyl)-2-oxoethyl group, and a 2-(2-naphthyl)-2-oxoethyl group. Part of hydrogen atoms of these groups may be substituted by a heteroatom such as an oxygen atom, a sulfur atom, a nitrogen atom, and a halogen atom, or may be mediated by a heteroatom such as an oxygen atom, a sulfur atom, and a nitrogen atom. As a result, part of hydrogen atoms of these groups may form or mediate a hydroxy group, a cyano group, a carbonyl group, an ether bond, an ester bond, a sulfonic ester bond, a carbonate bond, a lactone ring, a sultone ring, a carboxylic acid anhydride, and a haloalkyl group. A specific partial structure may be a dibenzothiophene skeleton when $R^1$, $R^2$, or $R^3$ represents a direct binding with an adjacent benzene ring.

Each of "p1", "q1", and "r1" in the general formula (2) independently represents an integer of 0 to 5. When each of "p1", "q1", or "r1" represents two or more, a plurality of $R^1$s, $R^2$s, or $R^3$s corresponding thereto may be the same or different. When p1+q1+r1 represents two or more, a plurality of $R^1$s, $R^2$s, or $R^3$s may be bonded to form a ring together with a carbon atom on a benzene ring bonded thereto, and $R^1$ and $R^2$, $R^1$ and $R^3$, or $R^2$ and $R^3$ may be bonded to form a ring together with two benzene rings bonded thereto and a sulfur atom in the formula.

Illustrative example of the case where a plurality of $R^1$s, $R^2$s, or $R^3$s may be bonded to form a ring together with a carbon atom on a benzene ring bonded thereto (that is, a ring is formed on a benzene ring) is shown. The present invention is not restricted thereto,

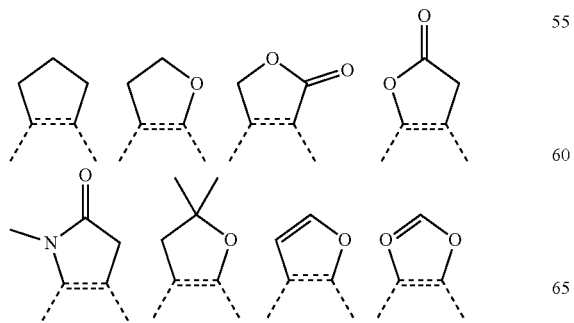

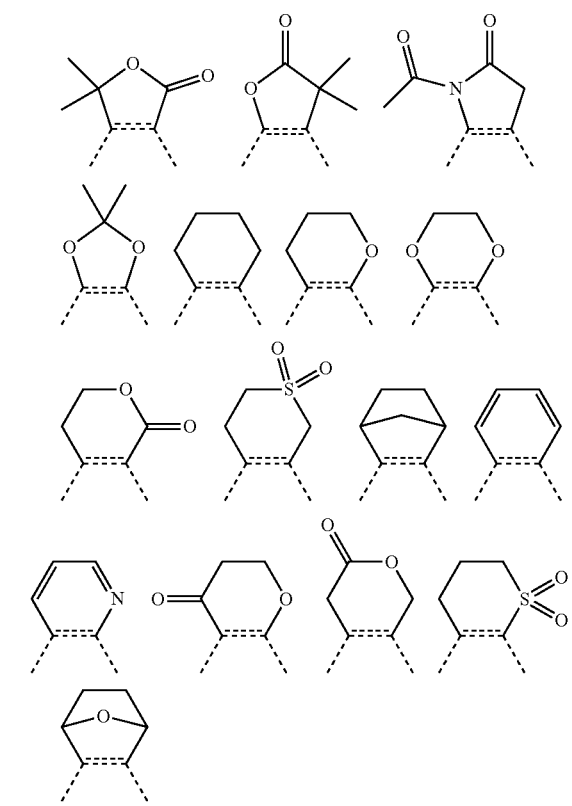

wherein, the broken line represents part of a benzene ring.

Illustrative example of the case where $R^1$ and $R^2$, $R^1$ and $R^3$, or $R^2$ and $R^3$ may be bonded to form a ring together with two benzene rings bonded thereto and a sulfur atom in the formula (that is, two benzene rings form a ring via a sulfur atom) is shown. The present invention is not restricted thereto,

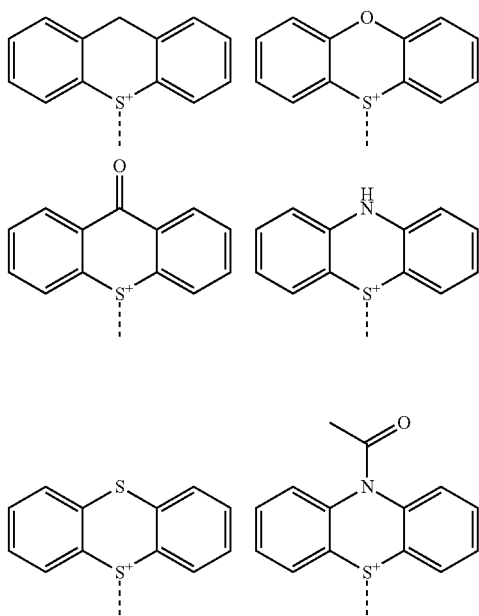

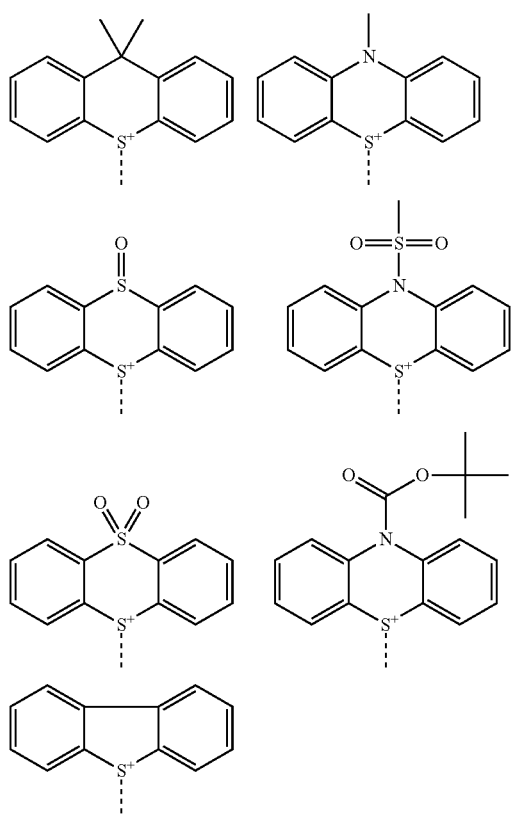
wherein, the broken line represents a bond.
Illustrative example of the cation having a partial structure represented by the general formula (1) includes the following cations, but the present invention is not restricted thereto,
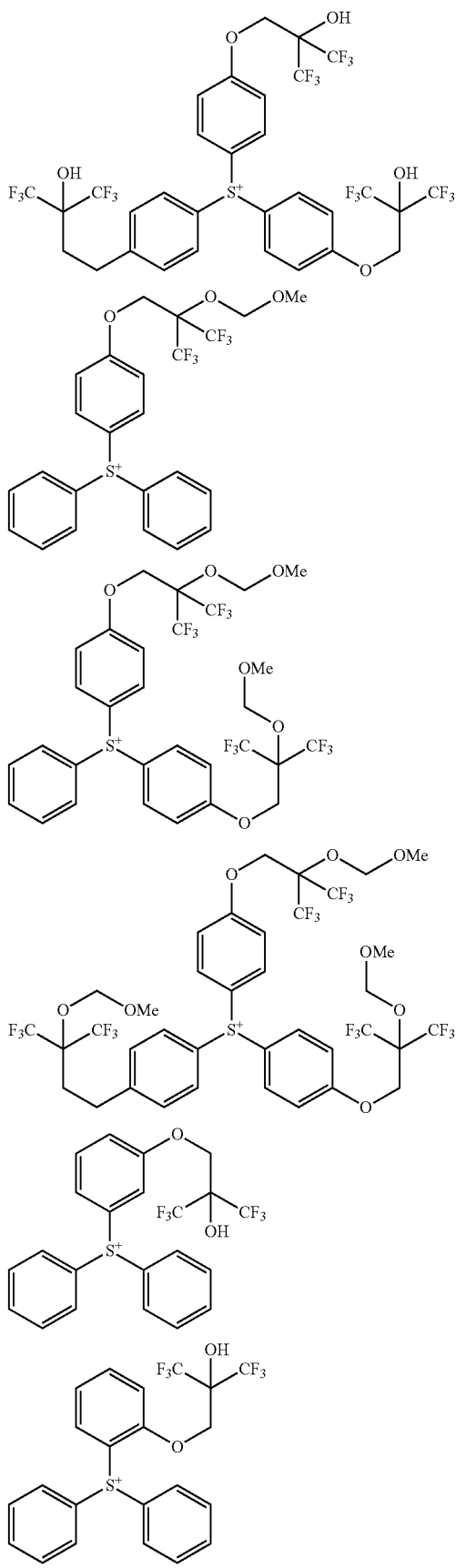

-continued
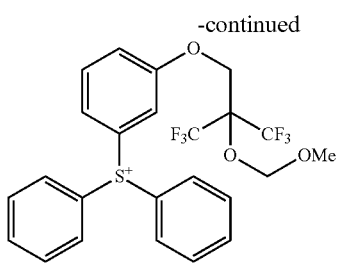
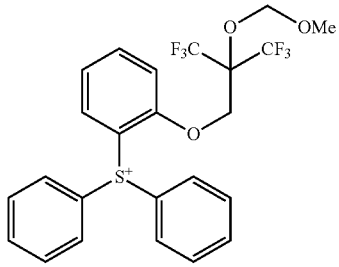
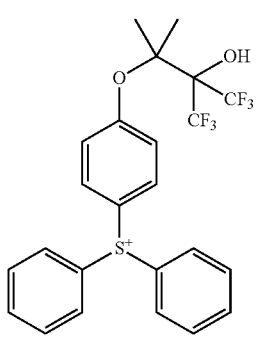
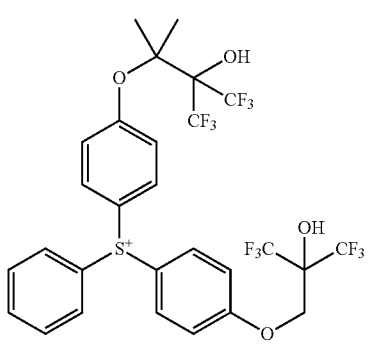
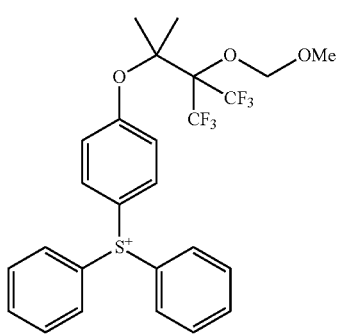
-continued
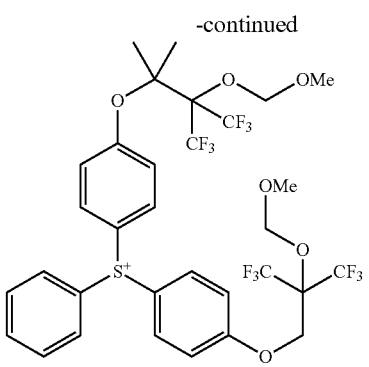
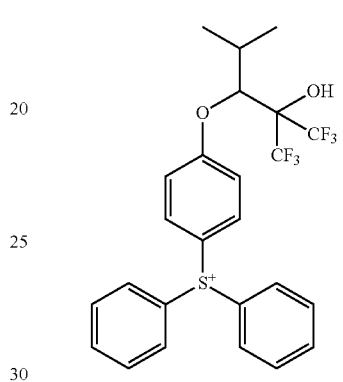
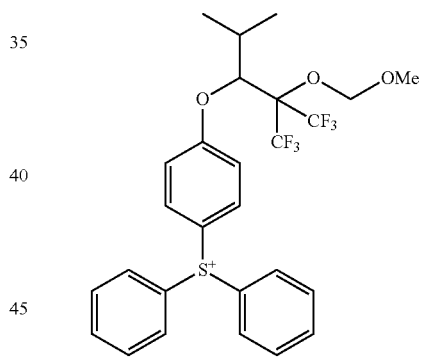
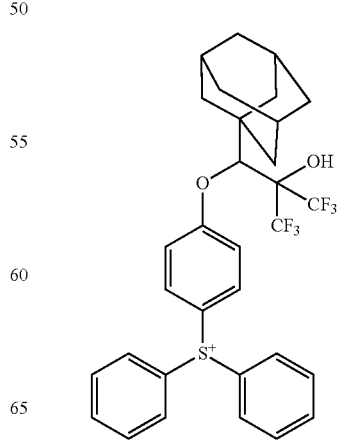

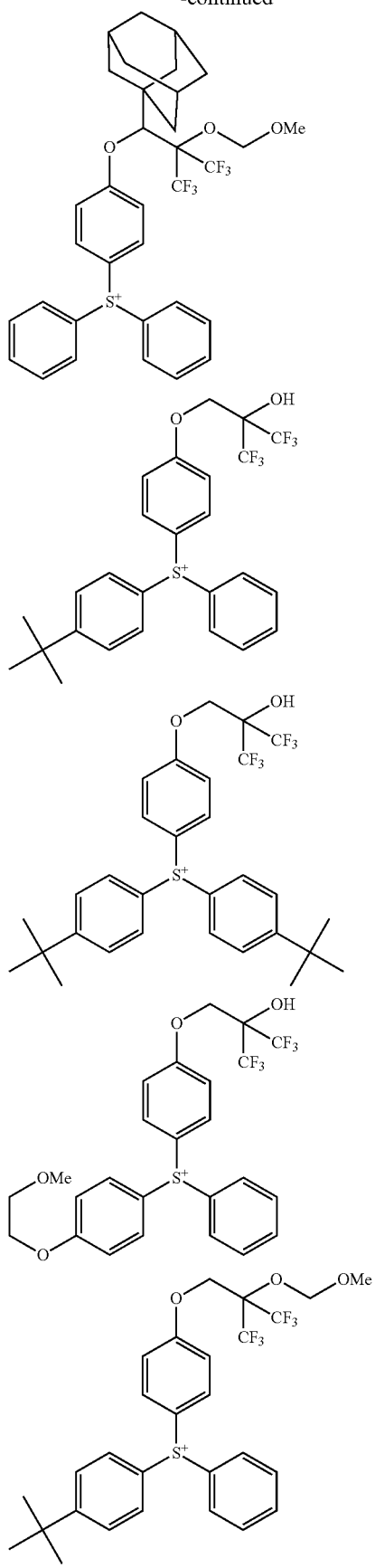
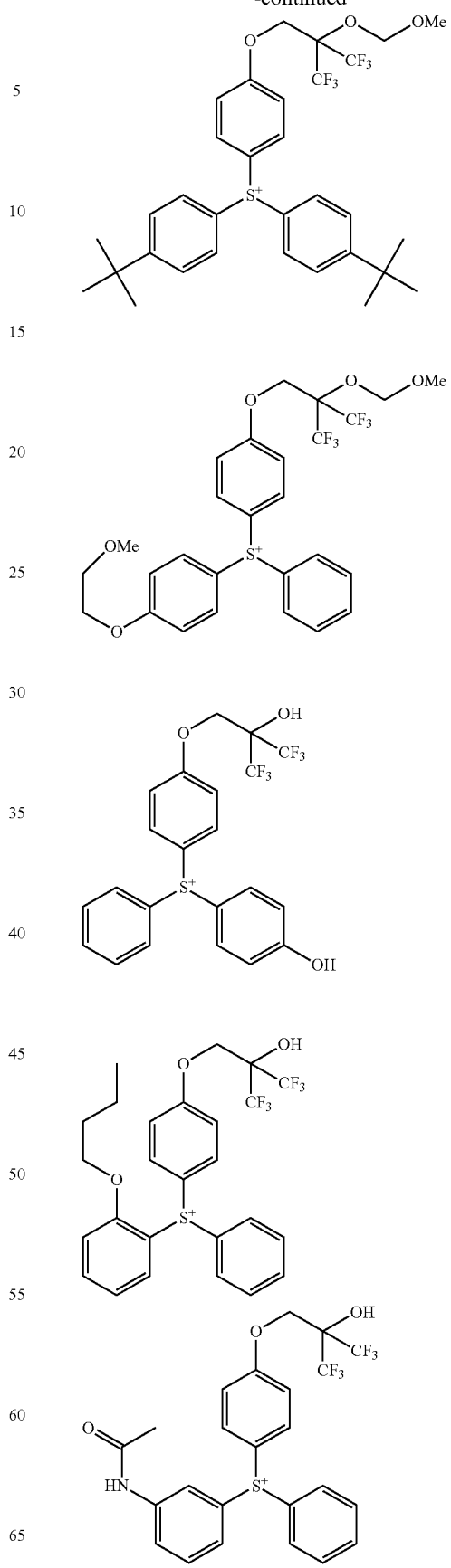

-continued
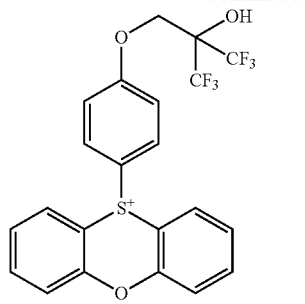
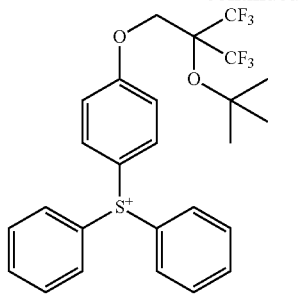
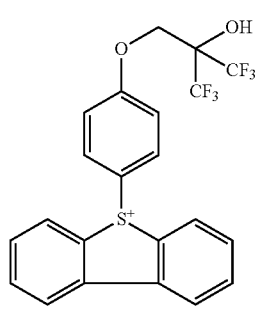
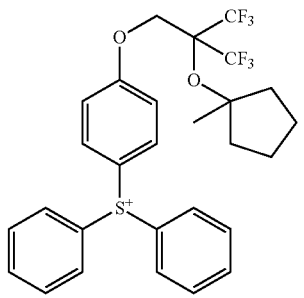
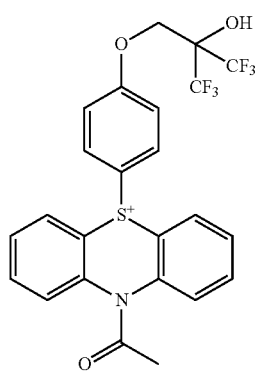
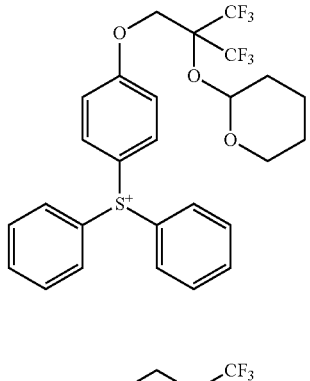
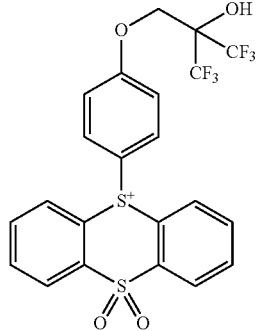
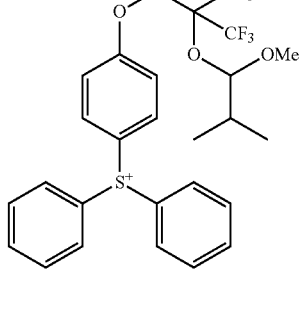
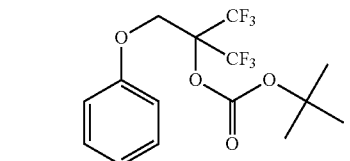
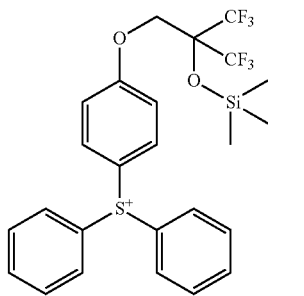

-continued
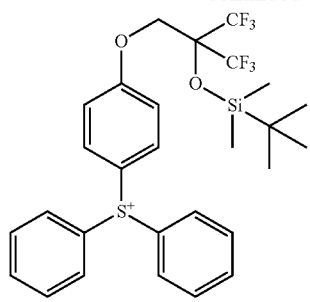
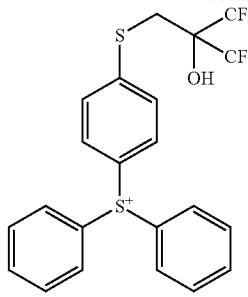
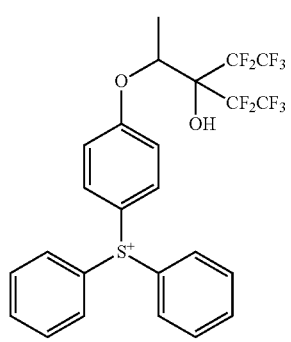
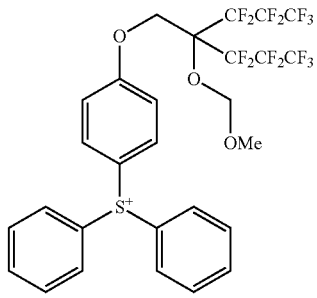
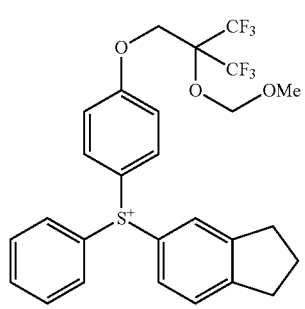
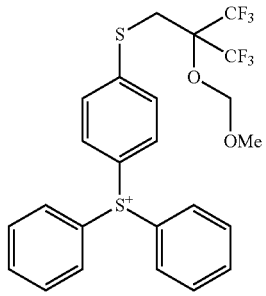
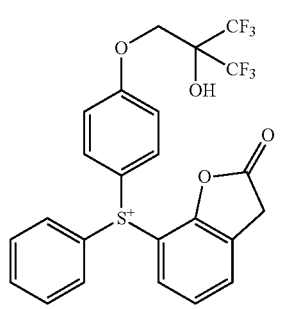
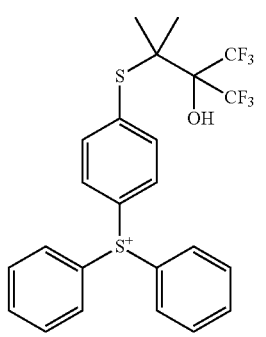
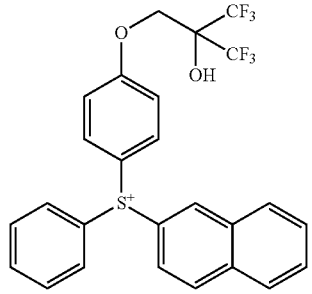
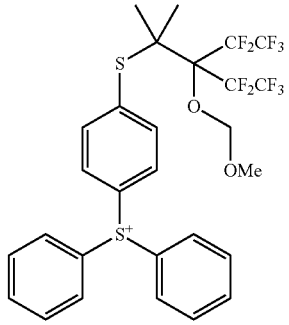

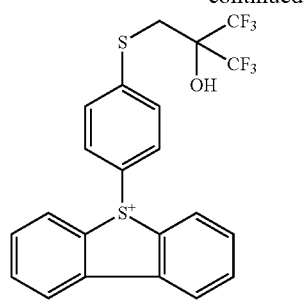
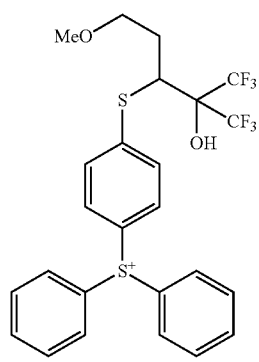
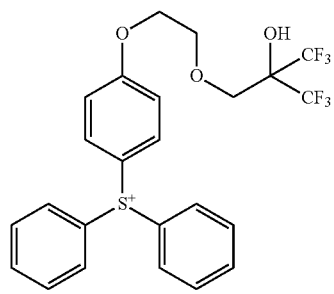
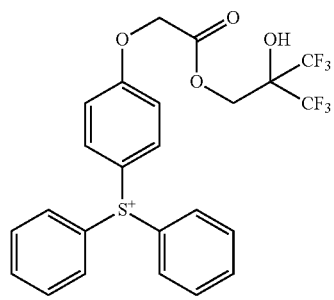
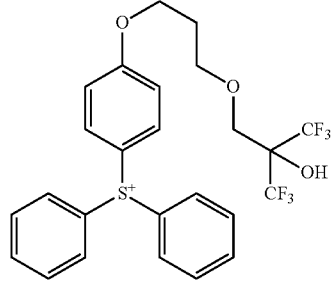
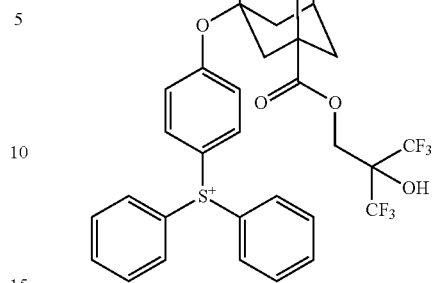
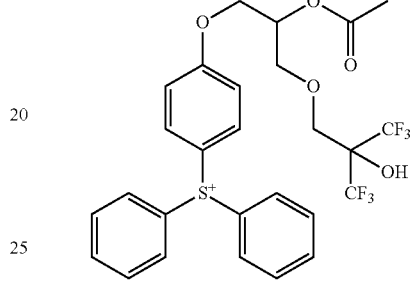
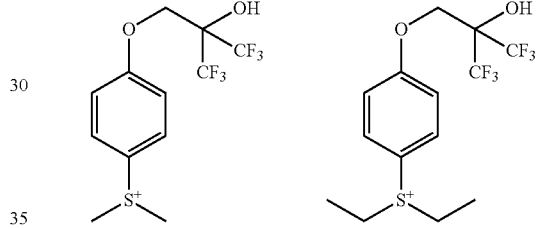
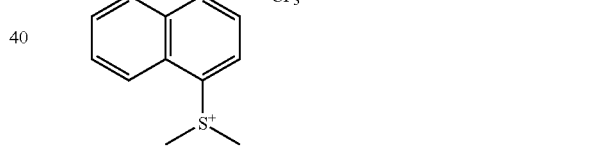
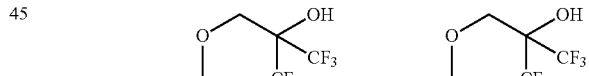
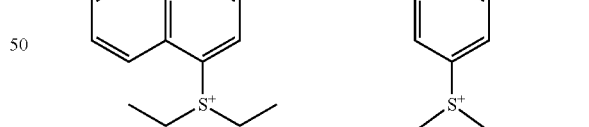
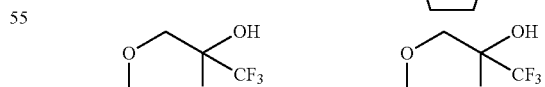

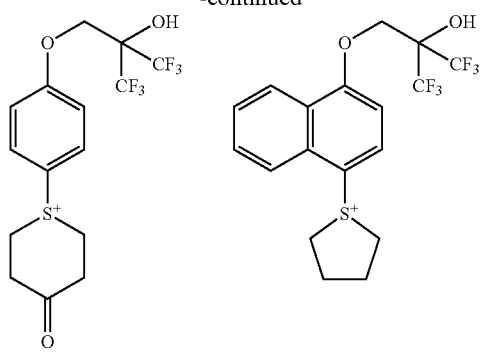
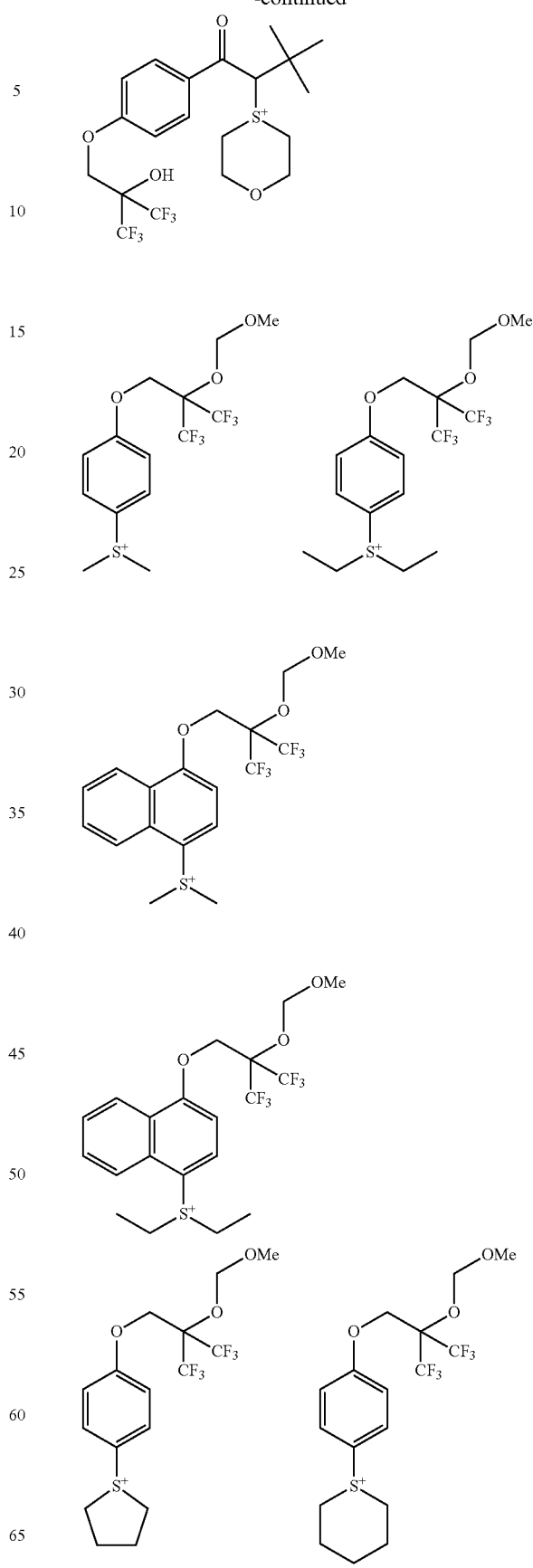

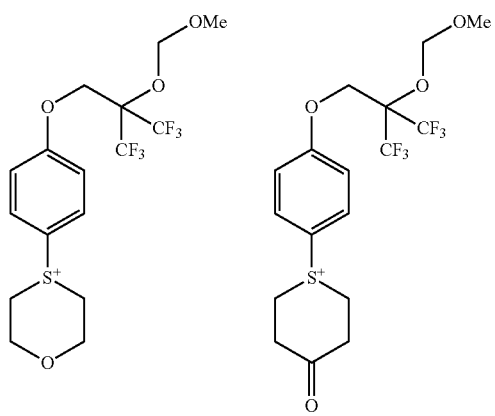
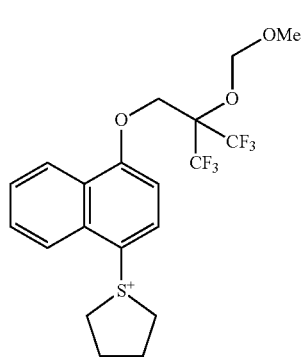
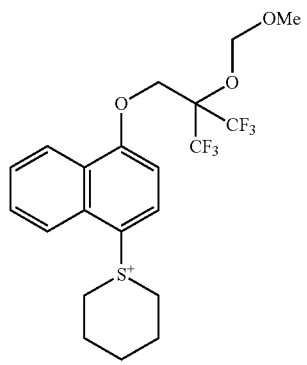
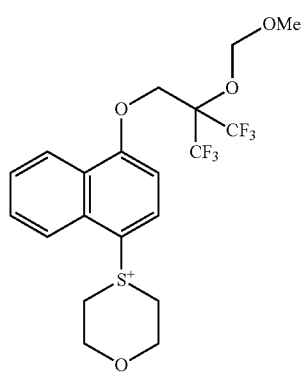
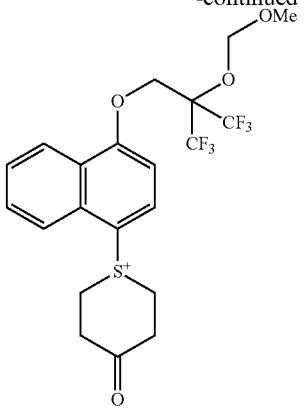
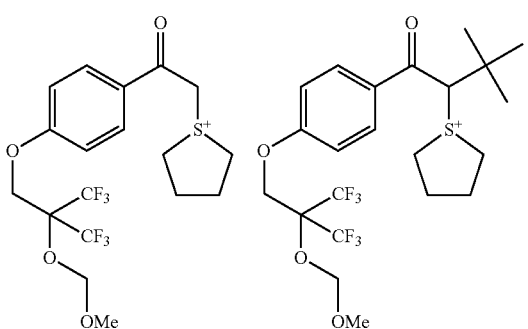
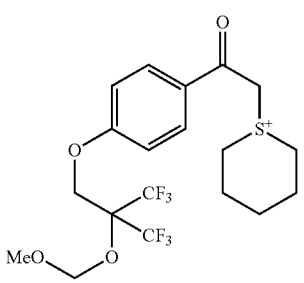
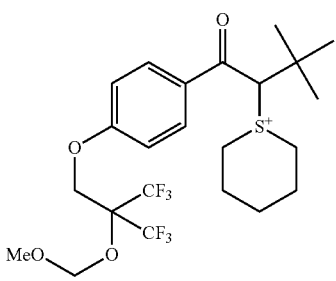
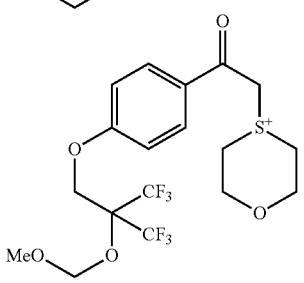

31
-continued
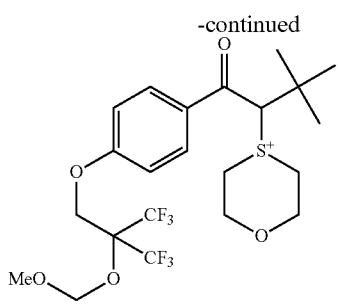
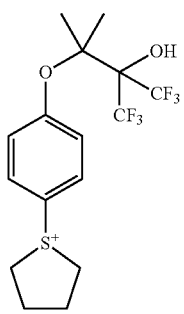 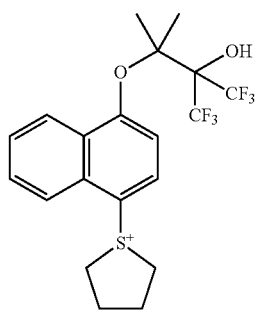
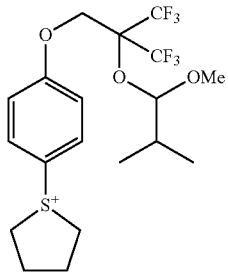
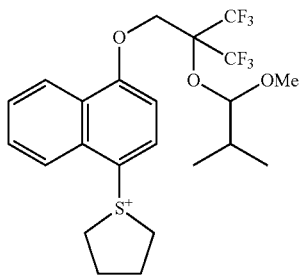
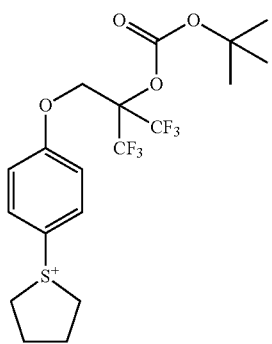
32
-continued
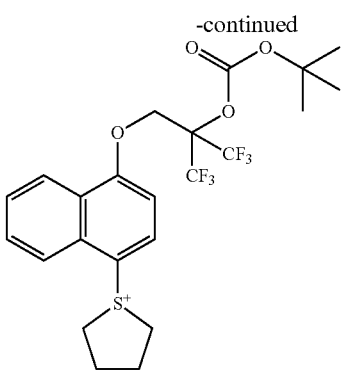
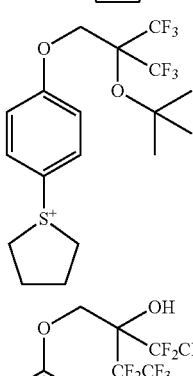 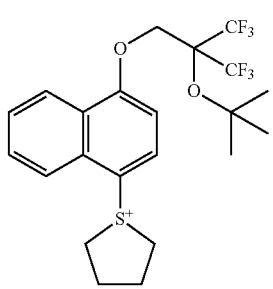
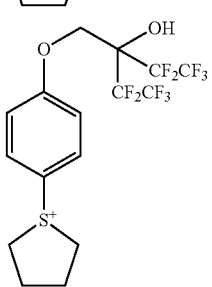
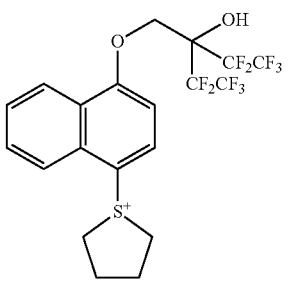
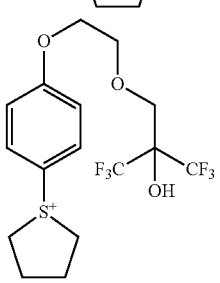
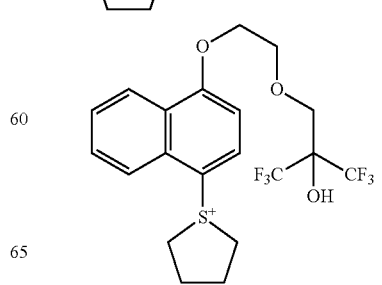

-continued

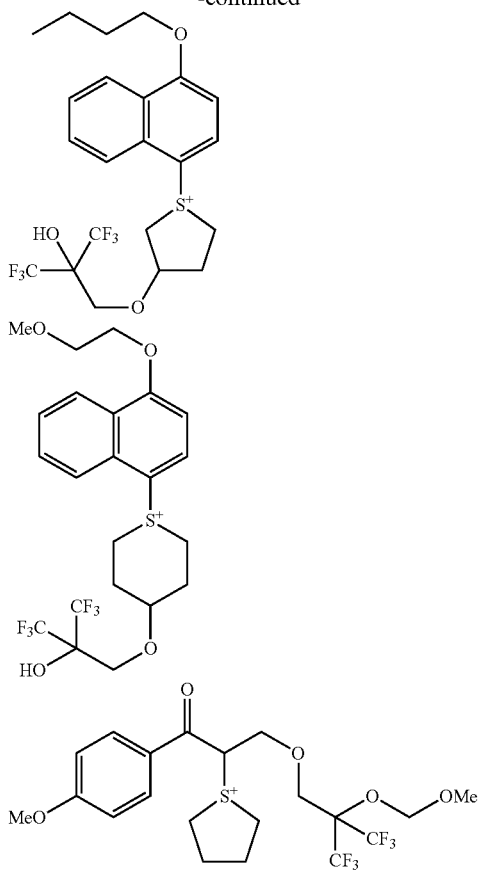

Z⁻ in the general formula (2) represents a monovalent anion. Z⁻ is not particularly restricted, but an anion derived from (fluoro)alkane sulfonate, benzene sulfonate, (fluoro) alkane carboxylic acid, imide acid, or methide acid may be used, preferably (fluoro)alkane sulfonate, benzene sulfonate, imide acid, or methide acid, and more preferably an anion represented by the following general formula (3),

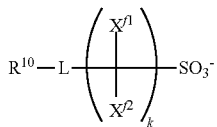

(3)

wherein, $R^{10}$ represents a linear, a branched, or a cyclic monovalent hydrocarbon group having 1 to 40 carbon atoms optionally containing a heteroatom; "L" represents a single bond or a divalent linking group; each of $X^{f1}$ and $X^{f2}$ independently represents a hydrogen atom, a fluorine atom, or an alkyl group substituted by one or more fluorine atoms; and "k" represents an integer of 0 to 4.

Each of $X^{f1}$ and $X^{f2}$ in the general formula (3) independently represents a hydrogen atom or a fluorine atom, or an alkyl group substituted by one or more fluorine atoms, preferably a hydrogen atom, a fluorine atom, or a trifluoromethyl group.

"k" in the general formula (3) represents an integer of 0 to 4, preferably an integer of 0 to 3, and particularly preferably an integer of 0 to 2.

The structure of an anion represented by the general formula (3) showing favorable structures of $X^{f1}$, $X^{f2}$, and "k" is represented by the following general formula (4a) or (4b). Other preferable anions include an anion represented by the following general formula (4c),

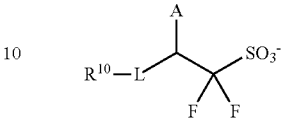

(4a)

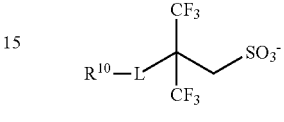

(4b)

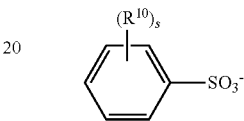

(4c)

wherein, $R^{10}$ and "L" represent the same meanings as before; "A" represents a hydrogen atom or a trifluoromethyl group; and "s" represents an integer of 0 to 5.

"L" in each of the general formulae (3), (4a), and (4b) represents a single bond or a divalent linking group, preferably a single bond, an ether bond, an ester bond, a sulfonic ester bond, an amide bond, a carbonate bond, and a carbamate bond, particularly preferably a single bond, an ether bond, and an ester bond.

$R^{10}$ in each of the general formulae (3) and (4a) to (4c) represents a linear, a branched, or a cyclic monovalent hydrocarbon group having 1 to 40 carbon atoms optionally containing a heteroatom. Illustrative example of the monovalent hydrocarbon group includes groups as shown in the examples of the $R^1$ to $R^3$, and in such groups, part of hydrogen atoms may be substituted by a substituent such as an alkyl group, an alkoxy group, an alkylcarbonyloxy group, and an alkyloxycarbonyl group. Illustrative example of the monovalent hydrocarbon group also includes a monovalent hydrocarbon group having a steroid skeleton and a monovalent hydrocarbon group having a dehydrocholic acid structure whose part of a steroid skeleton is modified with a substituent. $R^{10}$ preferably has a ring structure as a partial structure. The acid diffusion of an anion is controlled by a ring structure to improve lithography performance.

The Z⁻ is shown as follows. Illustrative example of the fluoroalkane sulfonateanion includes trifluoromethane sulfonate, pentafluoroethane sulfonate, and nonafluorobutanesulfonate. Illustrative example of the alkane sulfonateanion includes methane sulfonate and 10-camphor sulfonate. Illustrative example of the benzene sulfonate anion includes 4-methylphenyl sulfonate, 2,4,6-triisopropylphenyl sulfonate, and 2,4,6-tricyclohexylphenyl sulfonate. Illustrative example of the fluoroalkane carboxylic acid anion includes trifluoro acetate, pentafluoro propionate, and 3,3,3-trifluoro-2-hydroxy-2-trifluoromethyl propionate. Illustrative example of the alkane carboxylic acid anion includes benzoate, and 4-tert-butyl benzoate. Illustrative example of the imide acid anion includes bis(trifluoro methanesulfonyl)imide, bis(nonafluoro butanesulfonyl)imide, and N,N-hexafluoro-1,3-disulfonylimide. Illustrative example of the methide acid anion includes tris(trifluoromethanesulfonyl) methide.

Furthermore, illustrative example of the anion represented by each of the general formulae (3), (4a) to (4c) preferably used as $Z^-$ includes the following anions, but the anion in the sulfonium salt of the present invention is not restricted thereto. "A" in the formula represent the same meanings as before,
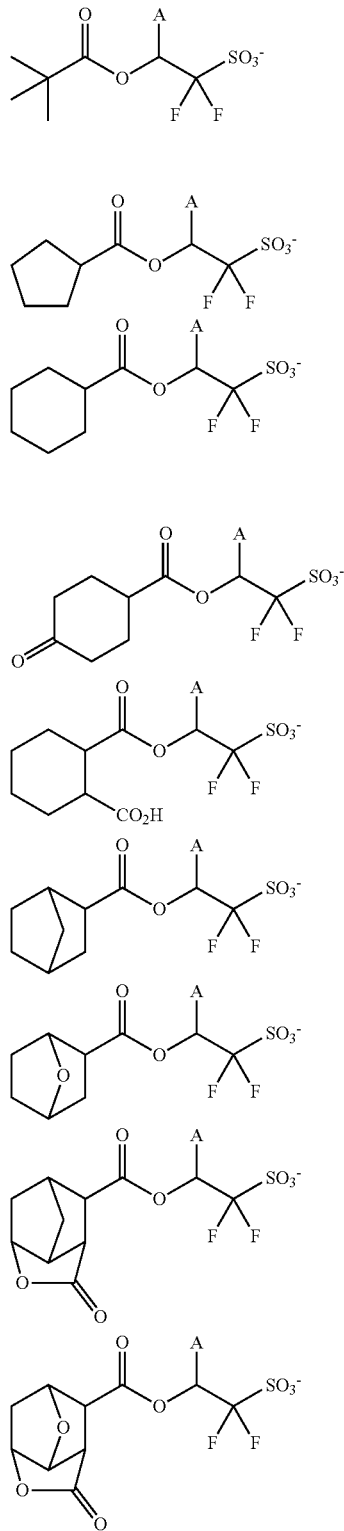
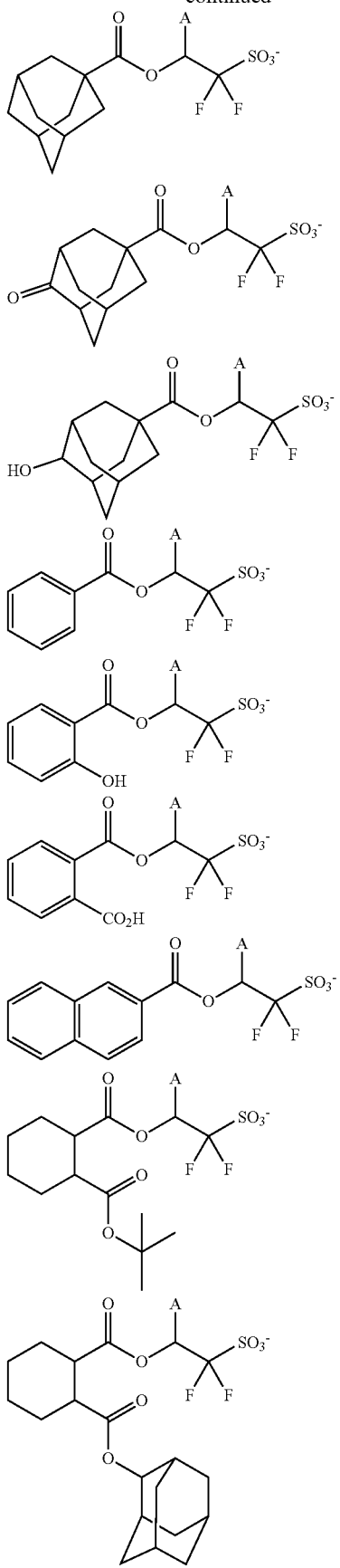

-continued
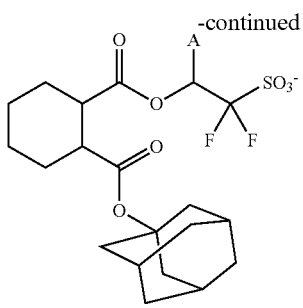
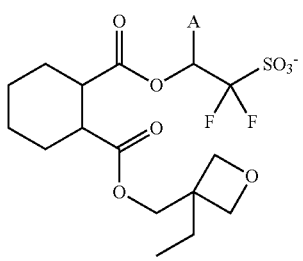
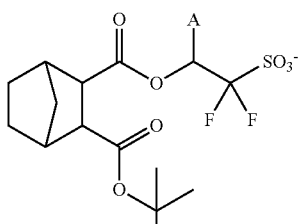
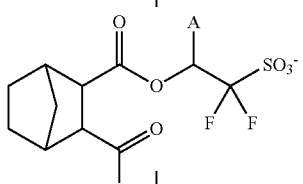
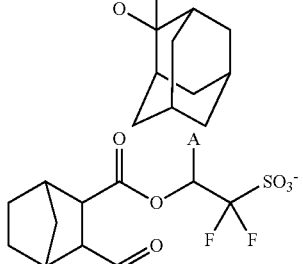
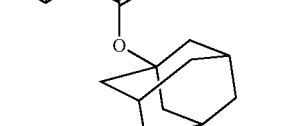
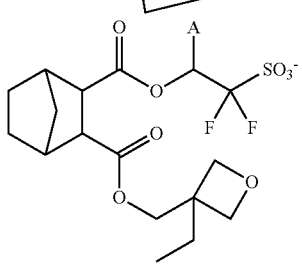
-continued
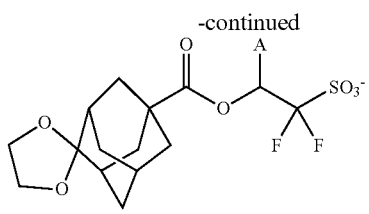
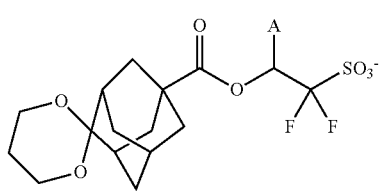
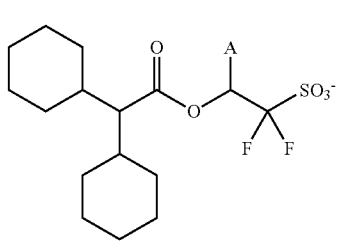
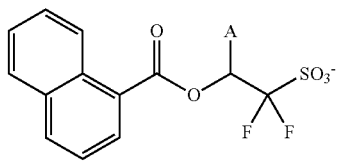
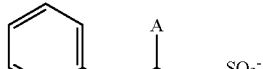
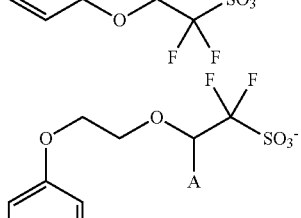
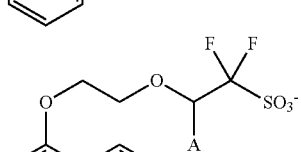
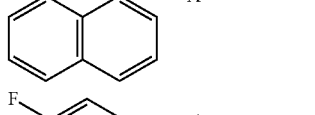
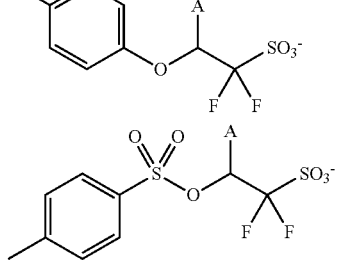

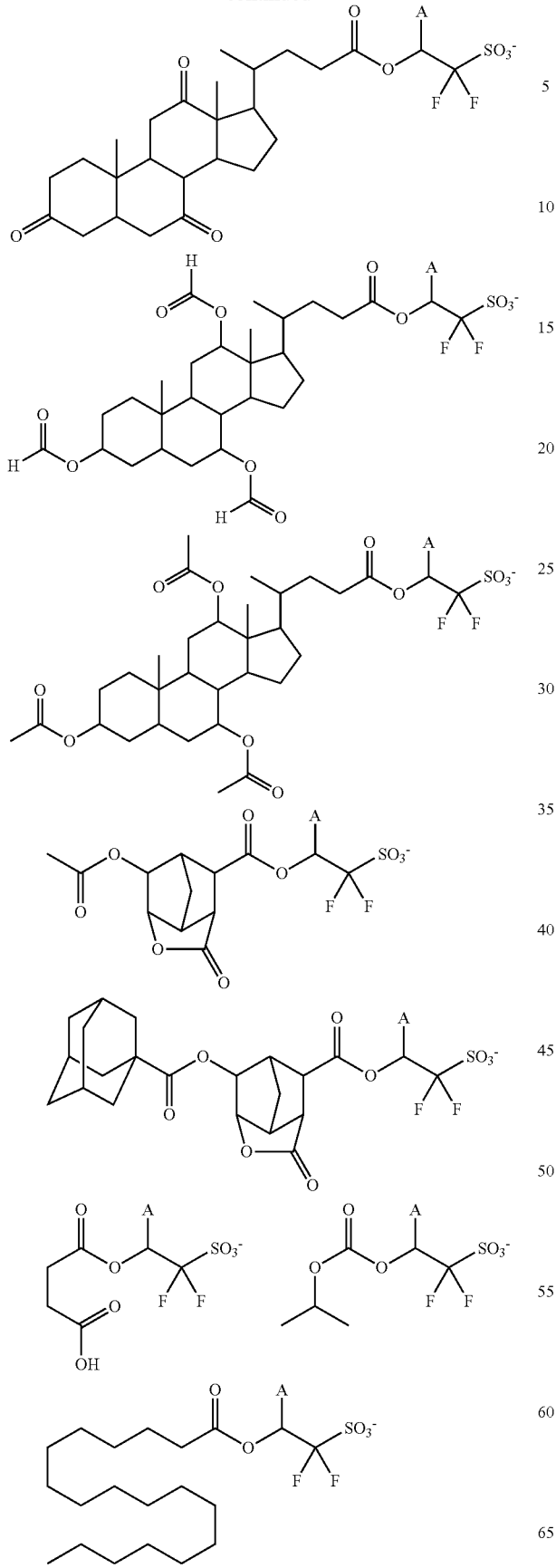
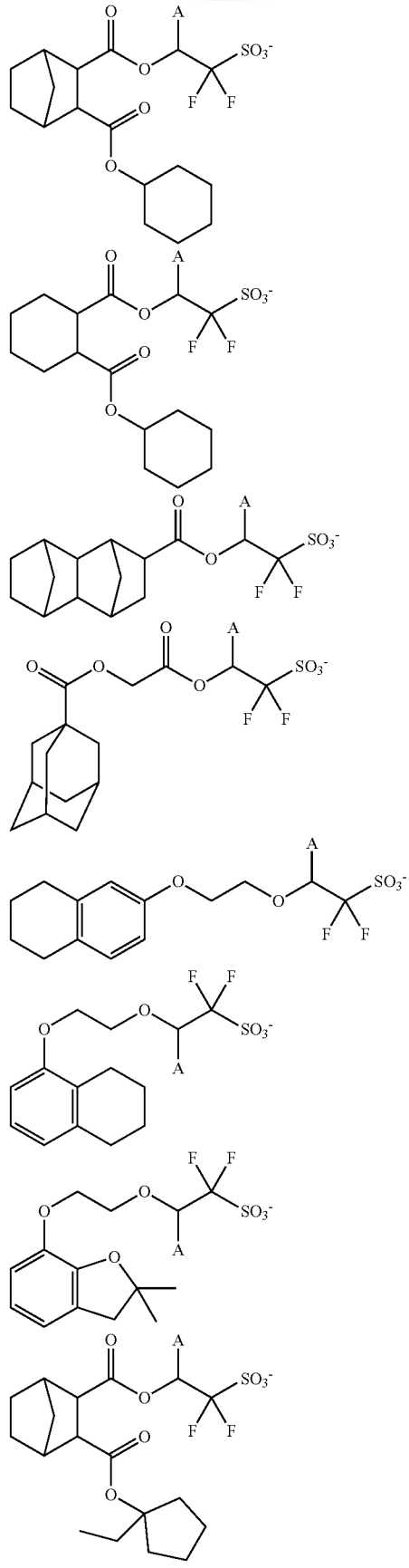

41
-continued
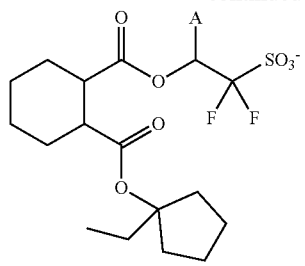
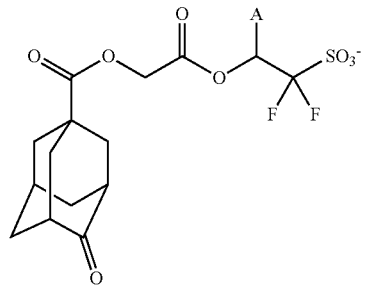
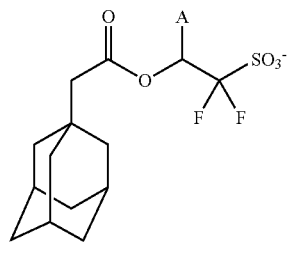
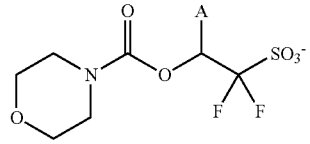
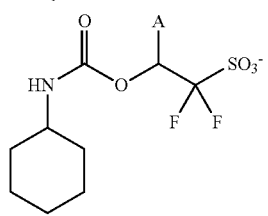
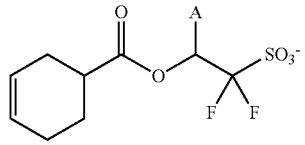
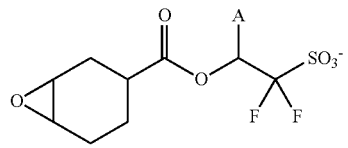
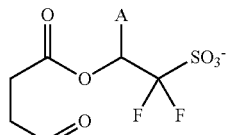
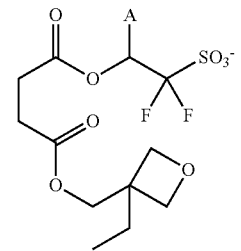
42
-continued
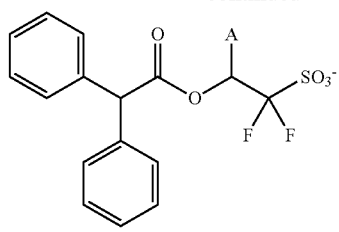
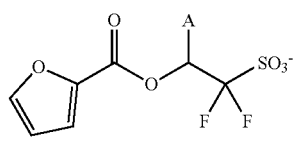
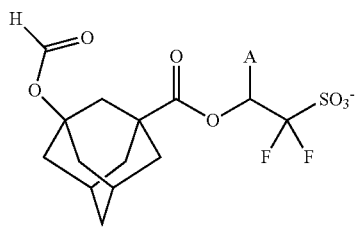
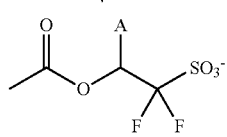
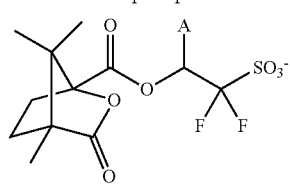
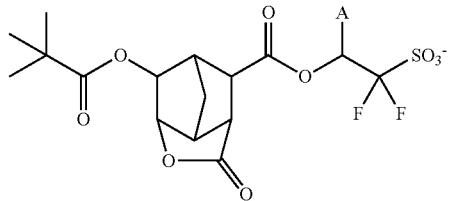
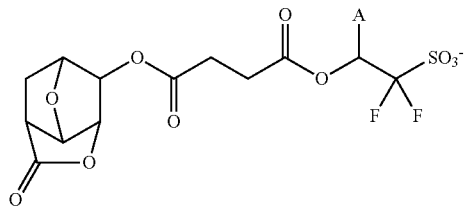
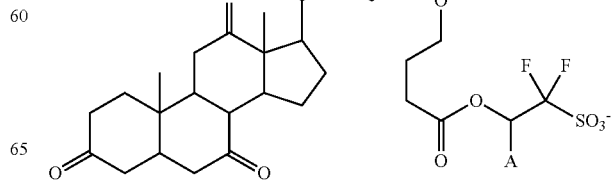

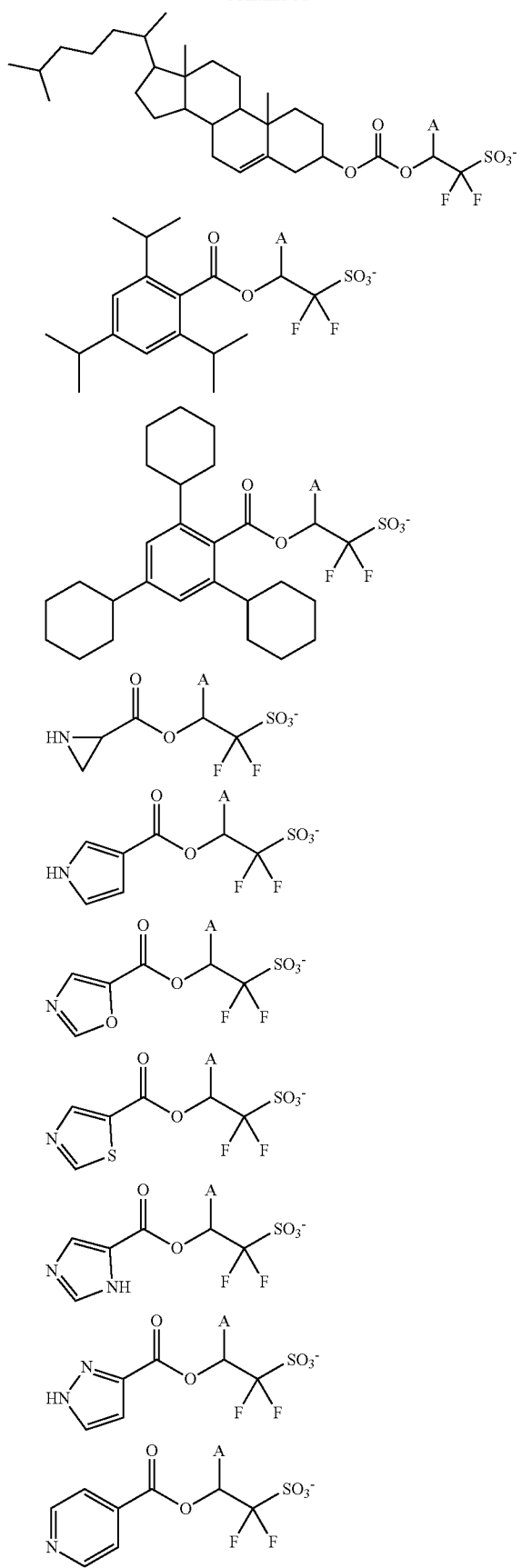
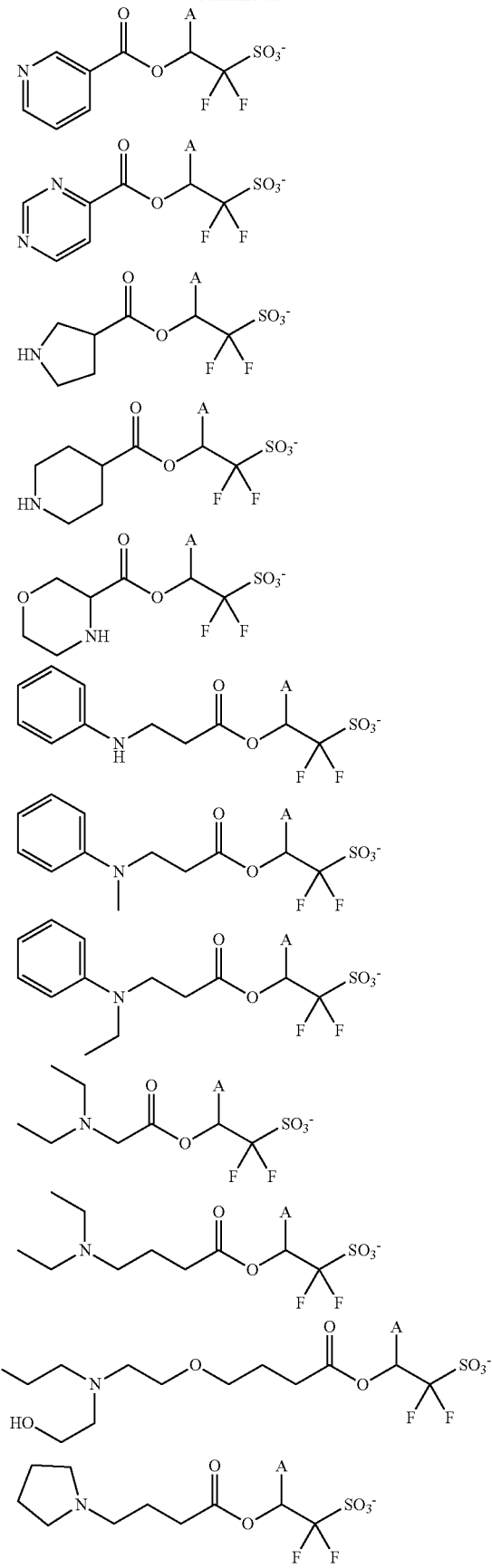

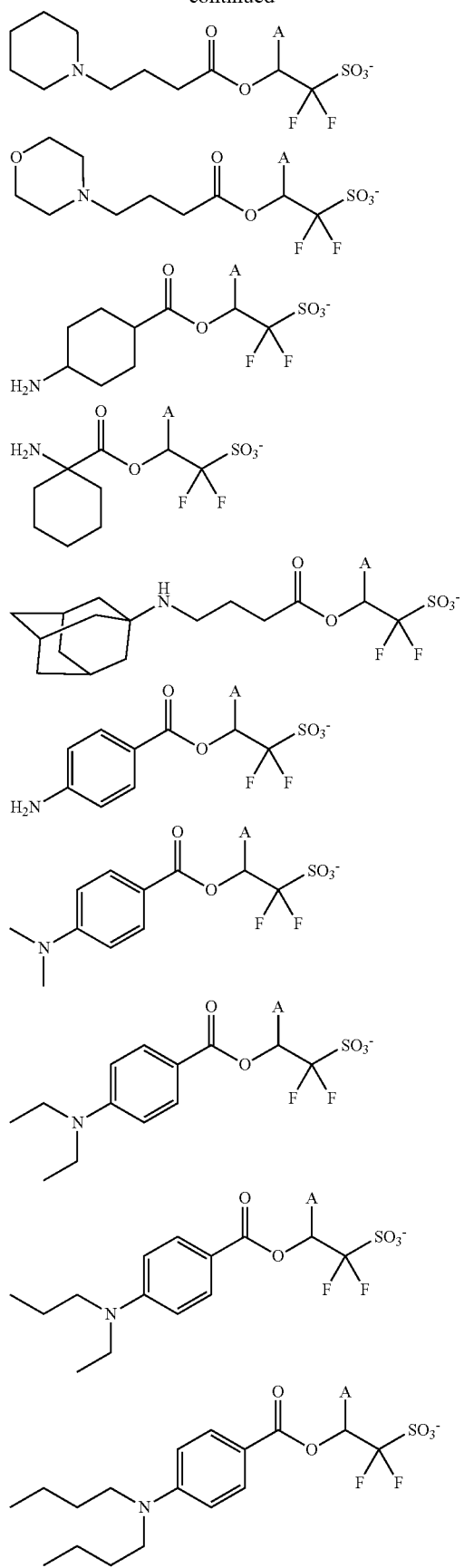
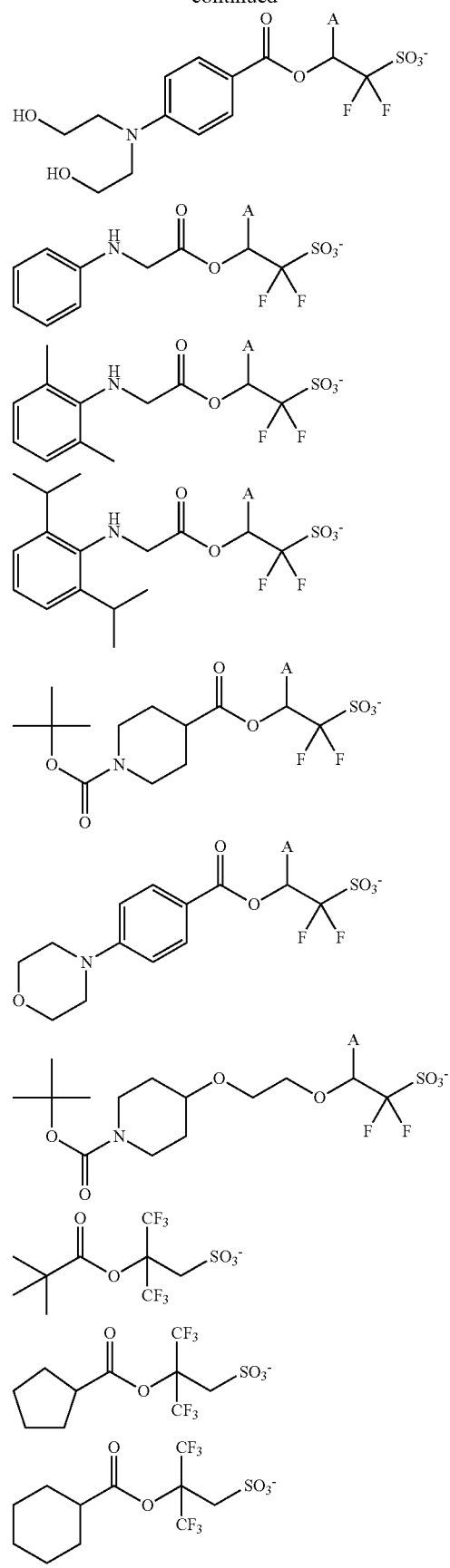

-continued
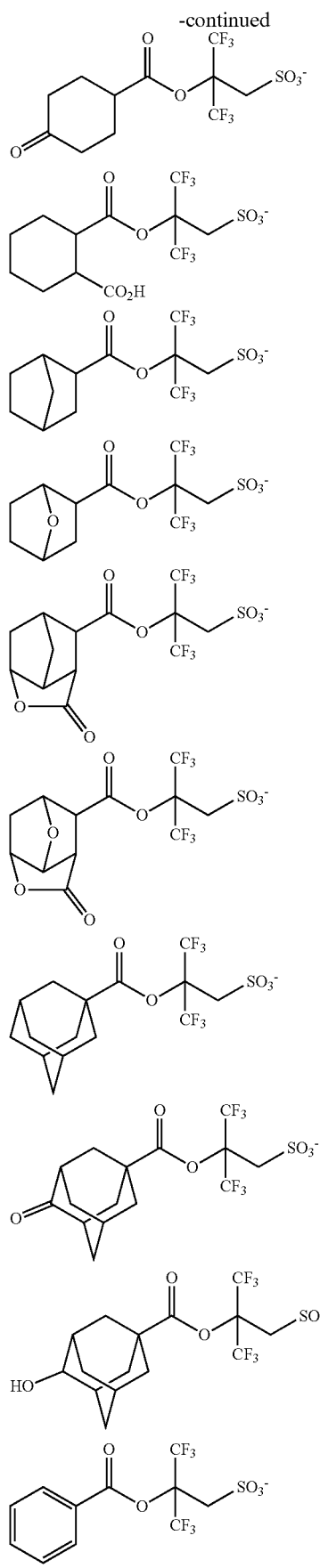
-continued
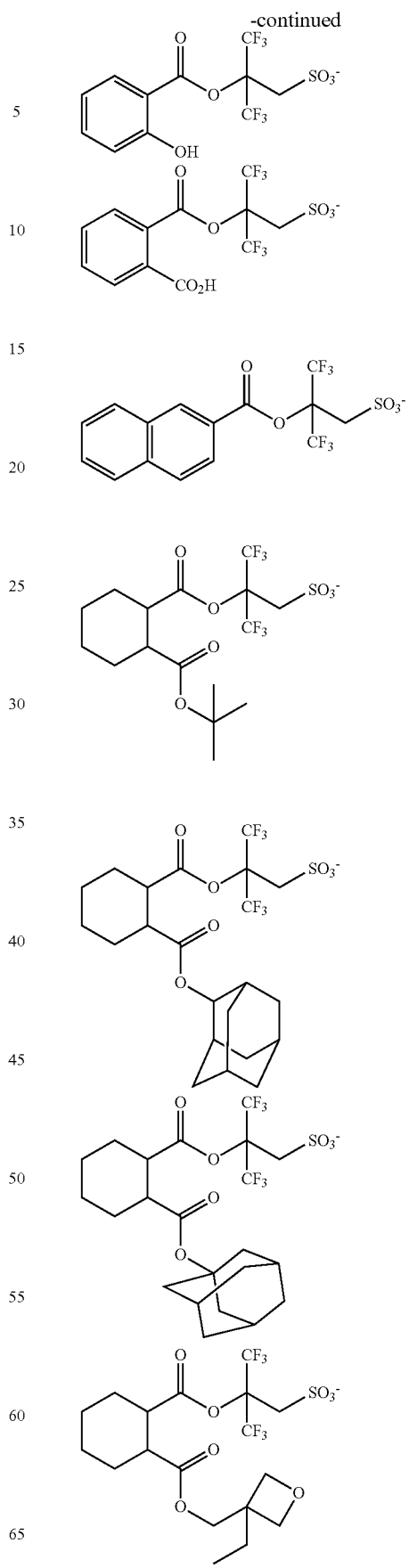

-continued
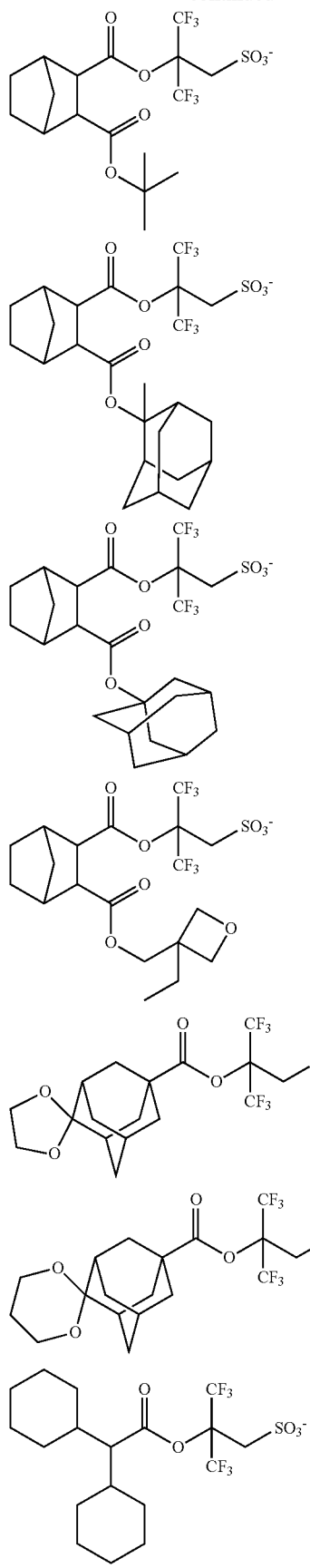
-continued
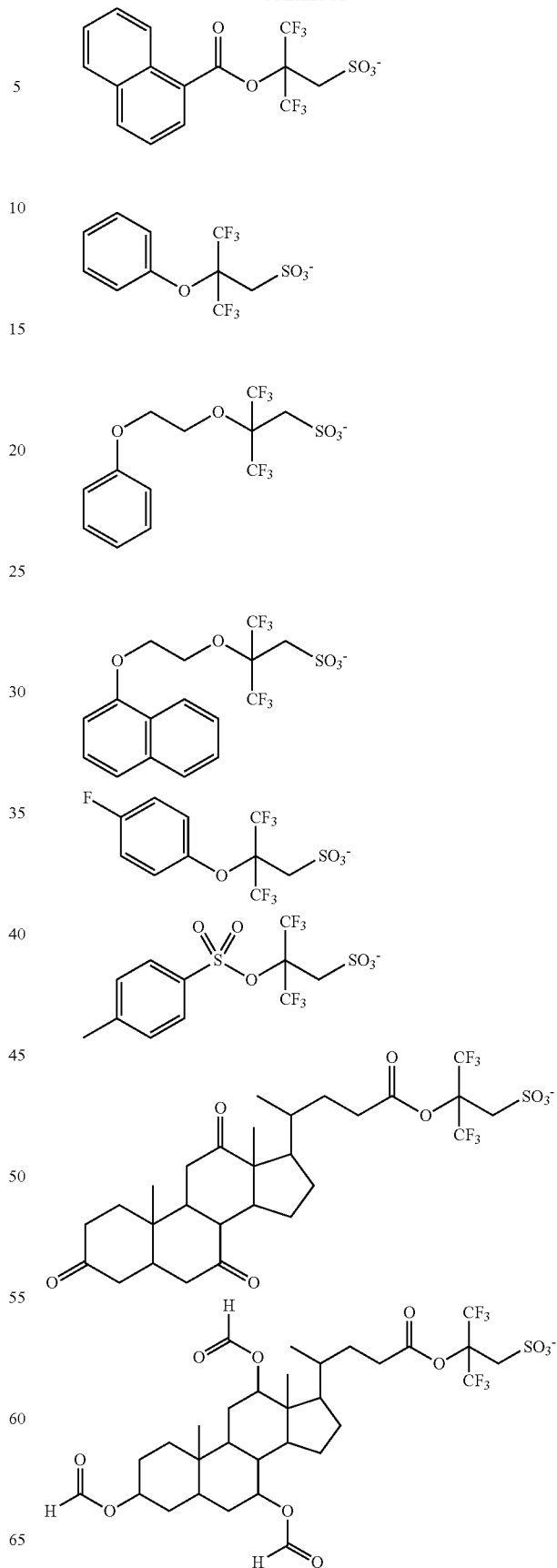

51
-continued
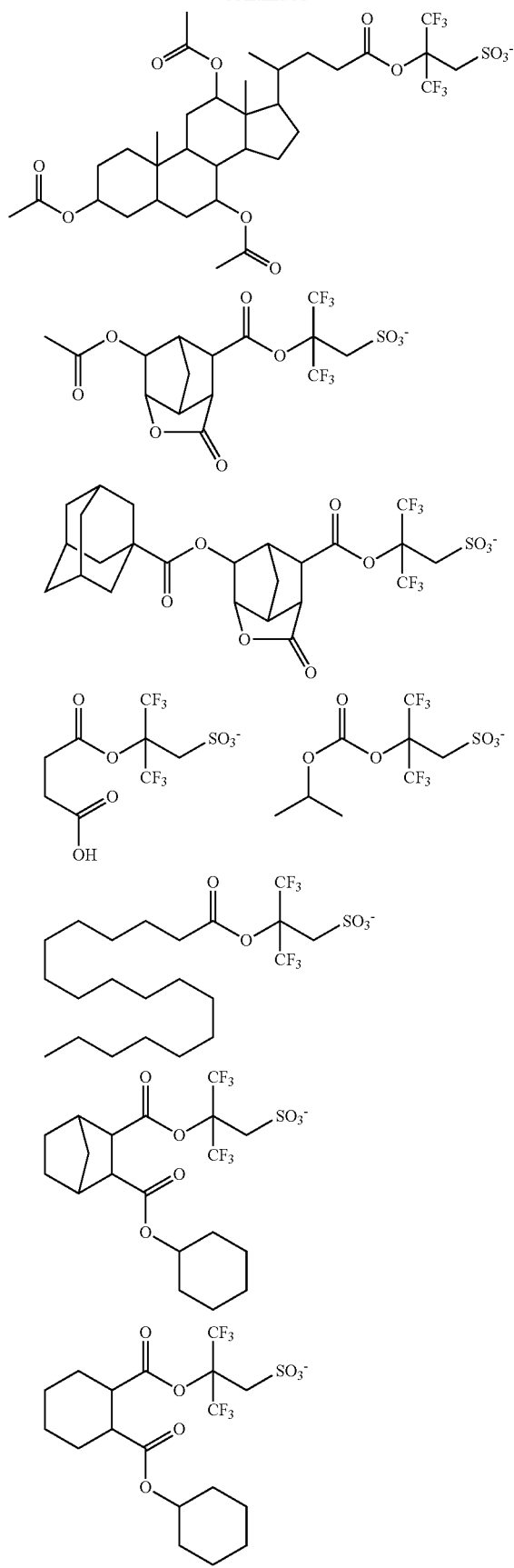
52
-continued
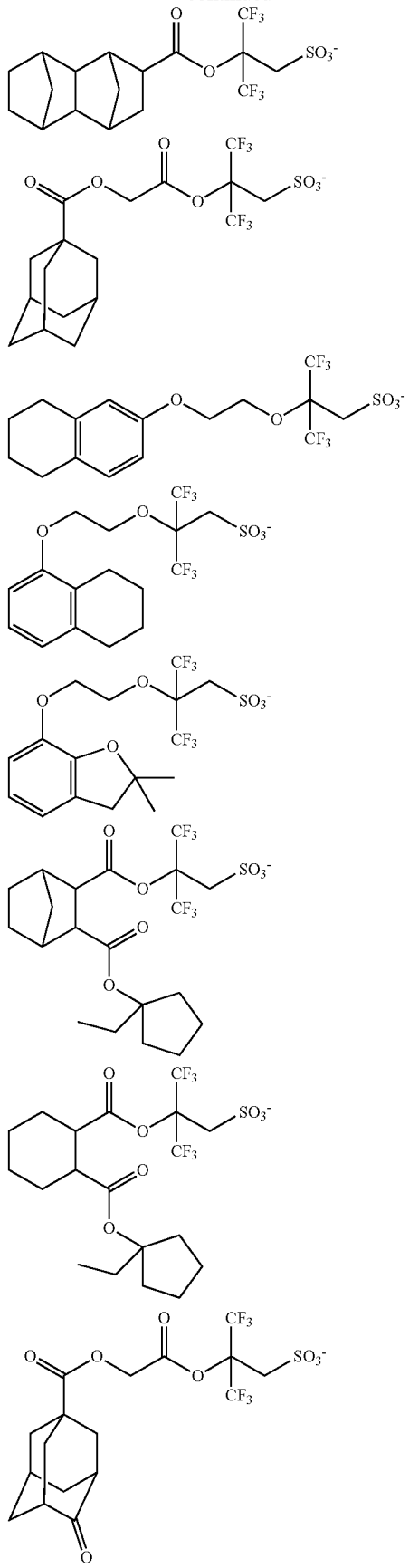

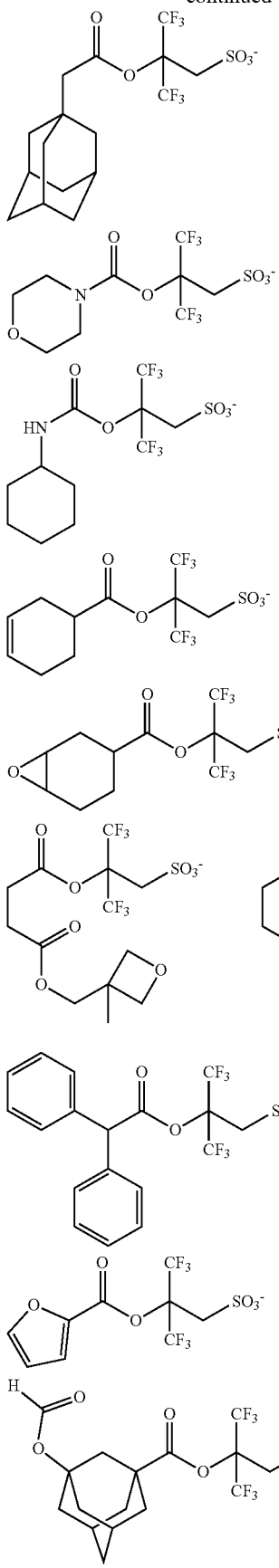
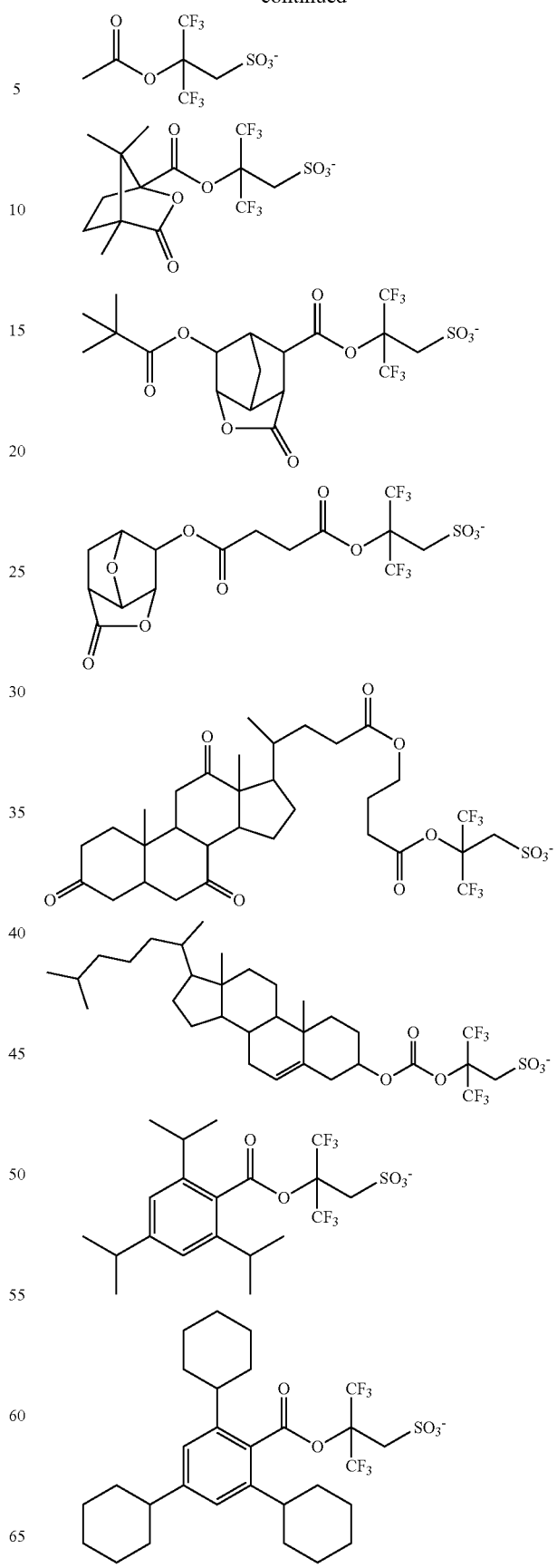

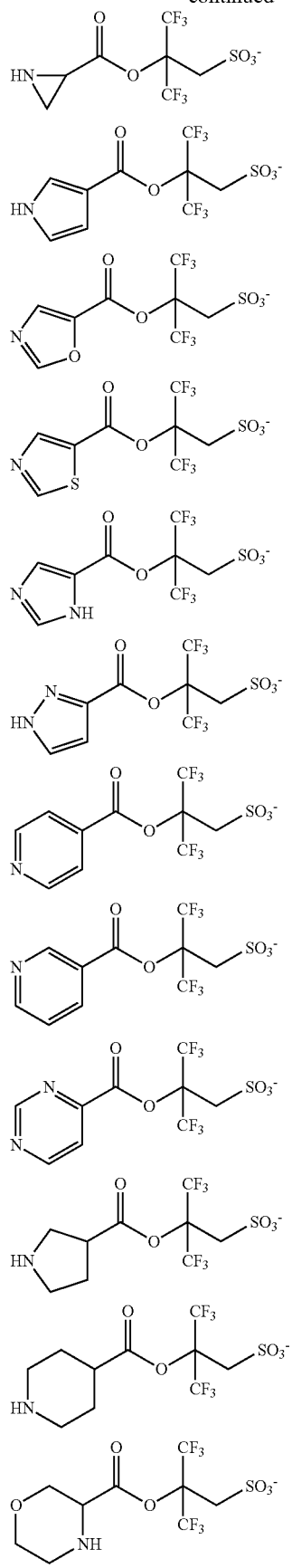
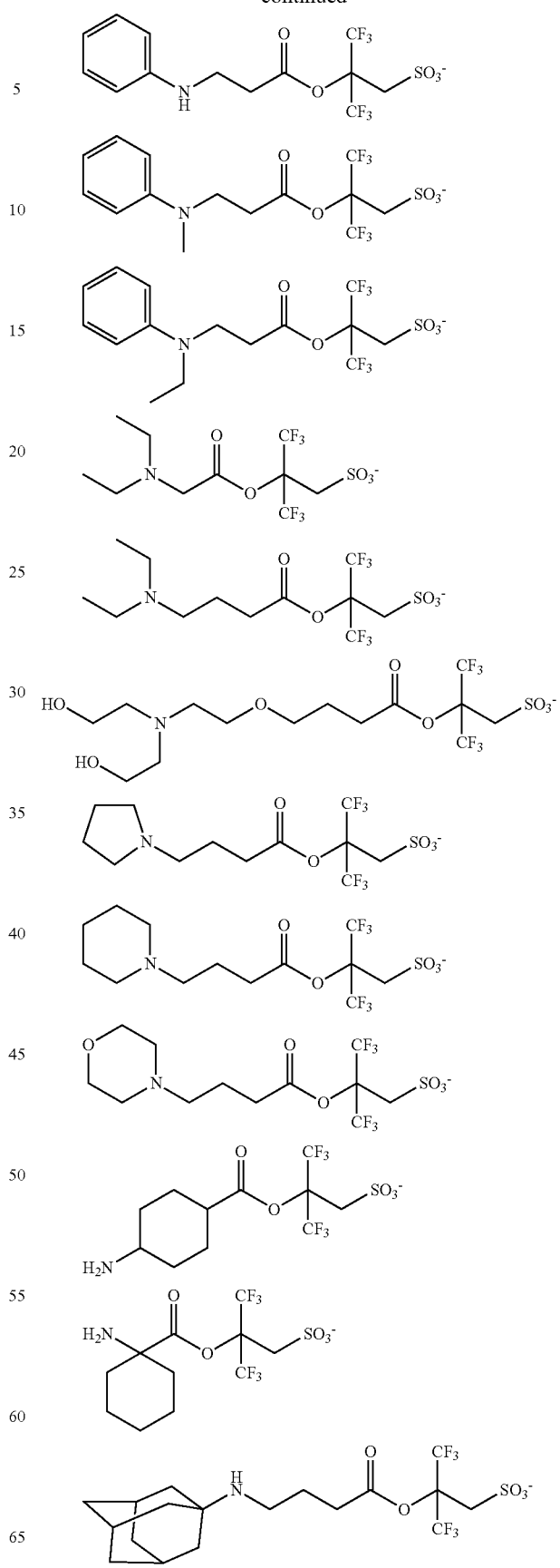

57
-continued
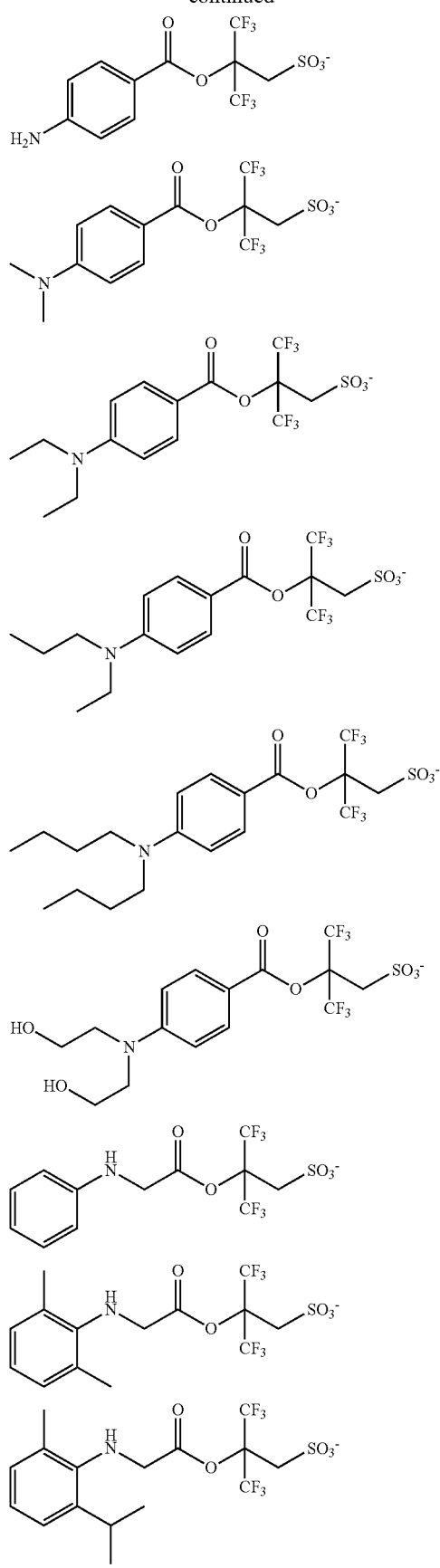
58
-continued
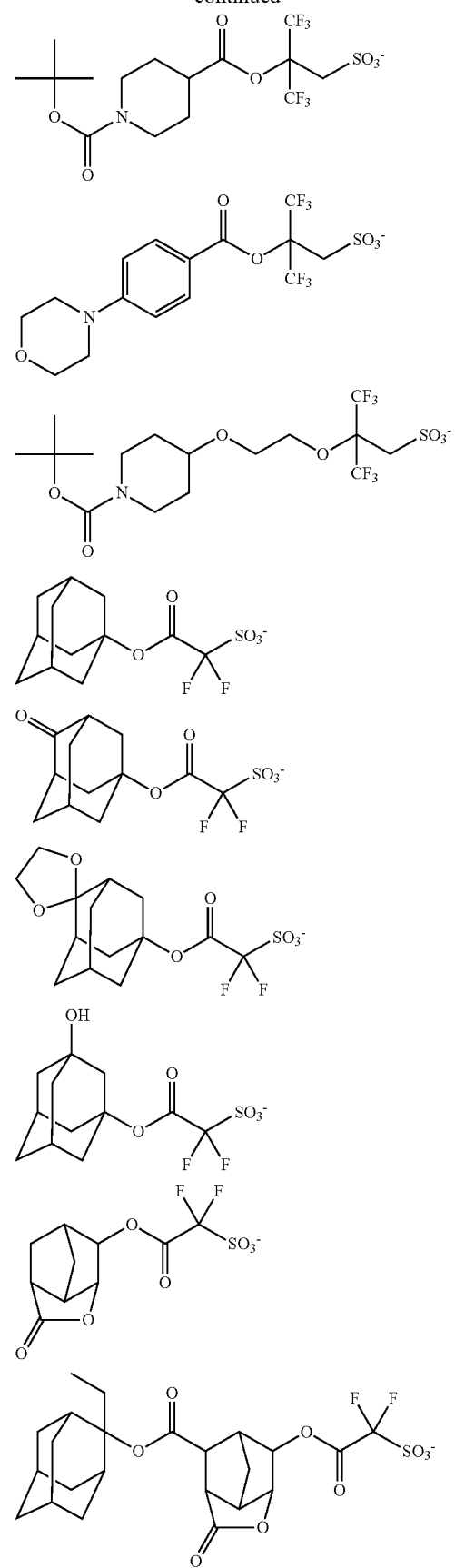

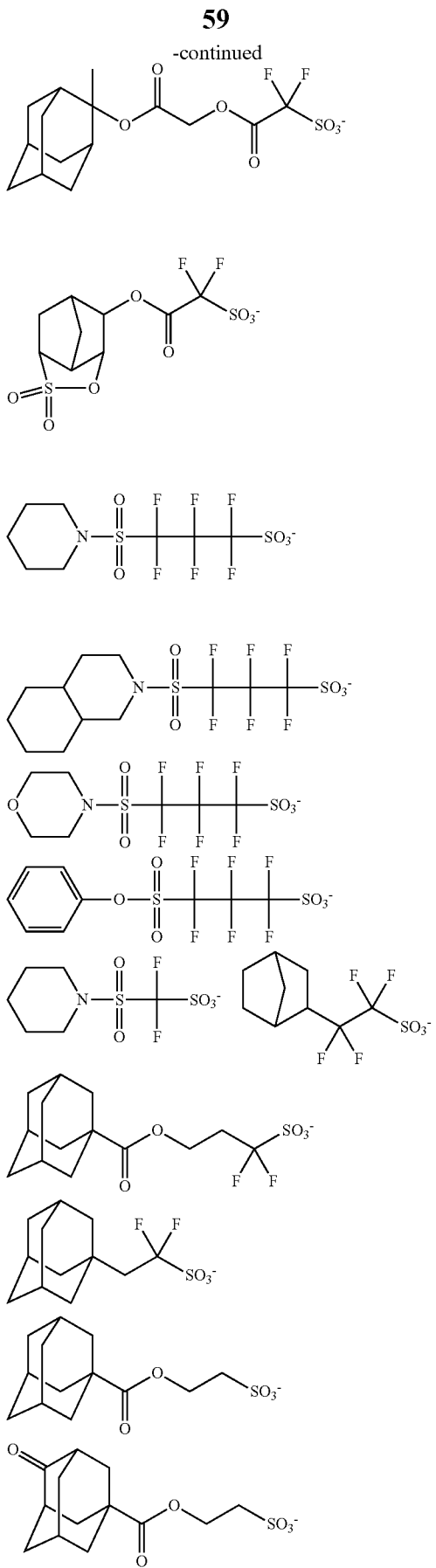

Illustrative example of the specific structure of the sulfonium salt of the present invention includes any combination of the cations and the anions, but the present invention is not restricted thereto.

The resist composition including the sulfonium salt of the present invention has few defects and is excellent in lithography performance such as MEF, EL, LWR, and CDU. The reason for such an effect is not known, but it can be attributed as follows.

Generation of low defects is attributed as follows. The sulfonium salt of the present invention is configured to include a structure for generating fluoroalcohol site (e.g., hexafluoroalcohol site), or a fluoroalcohol site through decomposition of an acid labile group by exposure. The fluoroalcohol unit includes a hydroxy group, and the electron-withdrawing effect by the α-position fluoroalkyl group raises the acidity, resulting in high solubility to an alkaline developer. The fluoroalcohol unit has a bulky substituent at α position, and a fluorine atom capable of improving the organic solvent solubility is introduced to provide high solubility to an organic solvent. Accordingly, it can readily reduce coating defects due to low solubility to a resist solvent (e.g., propylene glycol monomethylether acetate) and defects after development from low solubility to an alkaline developer (e.g., tetramethylammoniumhydroxide aqueous solution) or a developer for organic solvent (e.g., butyl acetate).

Improvement in CDU and LWR performance is attributed as follows. As described above, since the sulfonium salt of the present invention has high organic solvent solubility and is uniformly dispersed in a resist film without aggregation therein, CDU and LWR performance can probably be improved. Normally, due to subtle deviations such as dispersibility of solid contents, exposed amount, and PEB temperature, there are deviations of rate of dissolution into a developer even on the boundary surface of an exposed area and a non-exposed area. Advantageously, due to the compound of the present invention having high compatibility on the boundary surface, the rate of dissolution is made uniform to improve lithography performance such as CDU and LWR. The effect can be obtained by copolymerizing a structure unit having a fluoroalcohol site in a polymer. However, when such a structure unit is introduced into a polymer, the degree of freedom of a fluoroalcohol site declines, resulting unfavorable effects. By adding the unit as a monomer having high degree of freedom, the work load per molecule increases to obtain the effect with a small amount to be added.

Improvement in EL and MEF performance can be attributed as follows. The sulfonium salt of the present invention has a partial structure represented by the general formula (1), and as shown in the following formula (Q), a skeleton of a "-$A^{1a}$-$CR^aR^b$—$CR^{fa}R^{fb}$—O—" portion in the formula (1) (that is, $A^{1a}$, an oxygen atom, and two carbon atoms therebetween in the formula (1)) forms a five-membered ring conformation together with a proton (acid) for stabilization. When a proton (acid) is generated by exposure, the proton (acid) is coordinated to the "-$A^{1a}$-$CR^aR^b$—$CR^{fa}R^{fb}$—O—" portion in the formula (1) to form a stable conformation of a five-membered ring. A partial structure represented by the formula (1) has a high ability to control acid diffusion, resulting in improved MEF performance. Meanwhile, when 3 carbon atoms exist between an oxygen atom and $A^{1a}$ in the formula (1), the six-membered ring can be subjected to stable conformation. In this case, however, the resulting conformation is chair-type, instead of more stable conformation due to steric repulsion at axial position due to bulky fluoroalkyl group to reduce the effect of controlling acid diffusion,

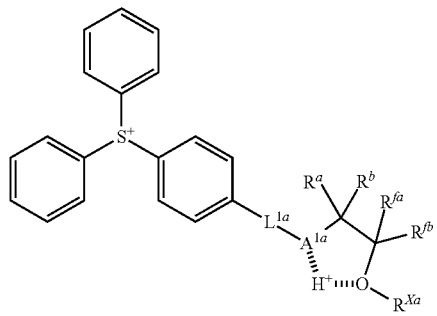

(Q)

wherein, $L^{1a}$, $A^{1a}$, $R^a$, $R^b$, $R^{fa}$, $R^{fb}$, and $R^{Xa}$ represent the same meanings as before.

In addition, when $R^{Xa}$ in the formula (1) represents an acid labile group, the dissolution contrast in an exposed area and a non-exposed area is improved, even using a photo acid generator, to improve various types of lithography performance such as MEF. In particular, when $R^{Xa}$ in the formula (1) represents an acetal-based protective group such as a methoxy methyl group (MOM group), as shown in the formula (R), a proton (acid) is trapped to control acid diffusion,

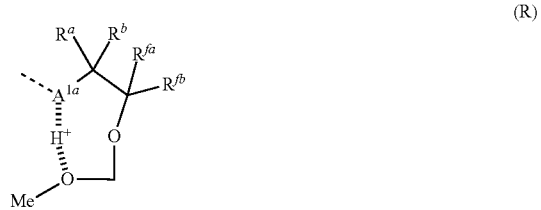

(R)

wherein, $A^{1a}$, $R^a$, $R^b$, $R^{fa}$, and $R^{fb}$ represent the same meanings as before.

Generally, higher molecular weight of a sulfonium salt can increasingly control acid diffusion. Accordingly, a sulfonium salt having a cation represented by the general formula (1') is provided with too small molecular weight, thereby providing insufficient ability to control acid diffusion.

Illustrative example of the method for synthesizing the sulfonium salt of the present invention is shown as follows, but the present invention is not restricted thereto. The sulfonium salt of the present invention can be synthesized according to the following reaction formula,

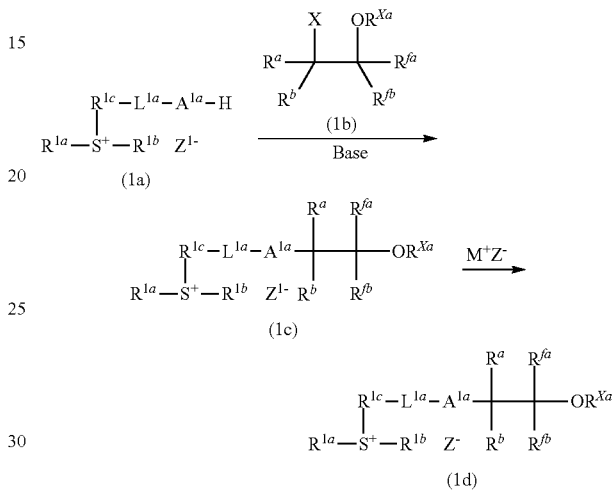

wherein, $L^{1a}$, $A^{1a}$, $R^a$, $R^b$, $R^{fa}$, $R^{fb}$, $R^{Xa}$, and $Z^-$ represent the same meanings as before; $R^{1a}$ and $R^{1b}$ represent a monovalent hydrocarbon group; $R^{1c}$ represents a divalent hydrocarbon group; X represents a leaving group; $Z^{1-}$ represents an anion; and $M^+$ represents a cation.

The reaction formula will be described in more detail. First, a compound (1b) is reacted with a compound (1a) as a nucleophile in the presence of a base to synthesize a compound (1c).

Illustrative example of the solvent in reaction includes a hydrocarbon such as toluene, xylene, hexane, and heptane; a chlorine-based solvent such as methylene chloride, chloroform, and dichloroethane; ether such as diethylether, tetrahydrofuran, and dibutylether; ketone such as acetone and 2-butanone; ester such as ethyl acetate and butyl acetate; nitrile such as acetonitrile; an aprotic polar solvent such as N,N-dimethyl formamide, N,N-dimethyl acetamide, and dimethyl sulfoxide; and water. These solvents can be used singularly or may be mixed in combination therewith as a mixture, or can be reacted in solventless state. Furthermore, a phase-transfer catalyst such as tetrabutyl ammonium hydrogen sulfate may be added as a catalyst.

Illustrative example of the base used in reaction includes metal amide such as sodium amide, potassium amide, lithium diisopropyl amide, potassium diisopropyl amide, lithium dicyclohexyl amide, potassium dicyclohexyl amide, lithium 2,2,6,6-tetramethyl piperidine, lithium bistrimethyl silylamide, sodium bistrimethyl silylamide, potassium bistrimethyl silylamide, lithium isopropylcyclohexyl amide, and bromomagnesium diisopropyl amide; alkoxide such as lithium tert-butoxide and potassium tert-butoxide; inorganic hydroxide such as sodium hydroxide, lithium hydroxide, potassium hydroxide, barium hydroxide, and tetra-n-butyl ammonium hydroxide; inorganic carbonate such as sodium carbonate, sodium hydrogen carbonate, lithium carbonate, and potassium carbonate; metal hydride such as sodium hydride, lithium hydride, potassium hydride, and calcium hydride; an alkyl metal compound such as trityl lithium, trityl sodium, trityl potassium, methyl lithium, phenyl lithium, sec-butyl lithium, tert-butyl lithium, and ethyl magnesium bromide; and amine such as ammonia, triethylamine, diisopropylethylamine, pyridine, lutidine, collidine, and N,N-dimethyl aniline.

The amount of a base to be used is preferably 0.5 to 1.0 mole relative to 1.0 mole of a nucleophile (1a), and more preferably 0.8 to 3.0 moles. When the amount is 0.5 moles or more, the reaction can fully be produced, and when the amount to be used is 1.0 mole or less, side reaction can be controlled, thereby controlling reduction in yield and purity and reducing costs.

The amount of a compound (1b) to be used is preferably 0.1 to 10 moles relative to 1.0 mole of a nucleophile (1a), and more preferably 0.5 to 2.0 moles. When the amount to be used is 0.1 moles or more, the resulting excessive residual nucleophile (1a) can make purification less difficult, and when the amount is 10 moles or less, side reaction can be controlled, thereby controlling reduction in yield and purity and reducing costs.

The reaction temperature is preferably from −70° C. to a boiling point of a solvent to be used, based on reaction conditions, normally from 0° C. to a boiling point of a solvent to be used. Since the side reaction can be promoted with higher reaction temperature, the reaction is essentially produced at the lowest temperature in the range that allows for a practical reaction speed to achieve high yield. The reaction time is preferably determined by following the progress of the reaction according to thin-layer chromatography, gas chromatography, ion chromatography, and liquid chromatography to improve the yield, but normally 30 minutes to 40 hours. The reaction mixture is subjected to normal aqueous work-up to obtain a sulfonium salt (1c), and as required, it can be purified according to a conventional method such as recrystallization and chromatography.

Furthermore, a target sulfonium salt (1d) can be synthesized by subjecting a sulfonium salt (1c) and a salt (M⁺Z⁻) having a desired anion (Z⁻) to ion exchange. The ion exchange can readily be conducted by a known method, e.g., a method disclosed in JP-A-2007-145797.

When a sulfonium salt (1d) whose $R^{Xa}$ represents an acid labile group is synthesized, the acid labile group in $R^{Xa}$ may already be introduced in a compound (1b), or introduced by modifying a sulfonium salt (1d) whose $R^{Xa}$ represents a hydrogen atom. As reaction conditions in modification, known conditions can be employed in a reaction of a usual modifier and a hydroxy group. In the reaction, an epoxide represented by the following general formula (1b') can be used as an alternative to a compound (1b),

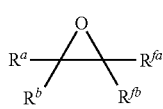

(1b')

In addition, the sulfonium salt of the present invention can be synthesized according to the following reaction formula, but the present invention is not restricted thereto,

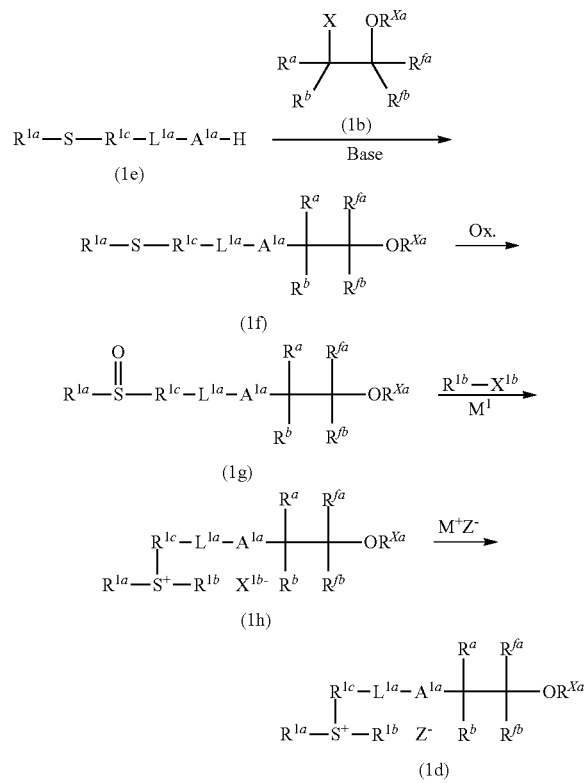

wherein, $L^{1a}$, $A^{1a}$, $R^a$, $R^b$, $R^{fa}$, $R^{fb}$, $R^{Xa}$, $R^{1a}$, $R^{1b}$, $R^{1c}$, X, M⁺, and Z⁻ represent the same meanings as before; $X^{1b}$ represents a halogen atom; and $M^1$ represents a metal.

The reaction formula will be described in more detail. As the compound (1c) is synthesized from the compounds (1a) and (1b), the sulfide (1e) reacts with the compound (1b) to obtain a sulfide (1f).

Then, the sulfide (1f) is oxidized by a known method to obtain a sulfoxide (1g). Illustrative example of the oxidant to be used includes hydrogen peroxide, performic acid, peracetic acid, and meta-chloroperbenzoic acid.

Subsequently, after a halogen compound ($R^{1b}$—$X^{1b}$) and a metallic reagent are reacted to prepare an organometallic reagent, the reagent acts on the sulfoxide (1g) for cationization to synthesize a sulfonium salt (1h).

Illustrative example of the organometallic reagent prepared by reaction of a halogen compound ($R^{1b}$—$X^{1b}$) and a metallic reagent includes a Grignard reagent, an organic lithium reagent, and an organic cupper reagent. These reagents can be prepared by using known methods, e.g., dropping a halogen compound into a mixed solution of a metal and a solvent under heating conditions and stirring the product under heating conditions. Illustrative example of the metal includes lithium, sodium, magnesium, aluminum, zinc, and potassium. Illustrative example of the solvent includes hydrocarbon such as pentane, hexane, heptane, benzene, toluene, and xylene; a chlorine-based solvent such as methylene chloride, chloroform, and dichloroethane; and ether such as diethylether, diisopropylether, tetrahydrofuran, tert-butylmethylether, and dibutylether. These solvents can be used singularly or mixed in combination with two or more solvents. The reaction temperature is preferably −10° C. to a boiling point of a solvent, and more preferably 40° C. to a boiling point of a solvent. The reaction time is normally 30 minutes to 40 hours.

Illustrative example of the solvent used in reaction of the organometallic reagent and the sulfoxide (1g) prepared includes hydrocarbon such as pentane, hexane, heptane, benzene, toluene, and xylene; a chlorine-based solvent such as methylene chloride, chloroform, and dichloroethane; and ether such as diethylether, diisopropylether, tetrahydrofuran, tert-butylmethylether, and dibutylether. The solvent can be used singularly or mixed in combination with two or more solvents. The reaction temperature is preferably from −70° C. to a boiling point of a solvent to be used based on reaction conditions, normally from 0° C. to a boiling point of a solvent to be used. Since the side reaction can be promoted with higher reaction temperature, the reaction is essentially produced at the lowest temperature in the range that allows for a practical reaction speed to achieve high yield. The reaction time is preferably determined by following the progress of the reaction according to thin-layer chromatography, gas chromatography, ion chromatography, and liquid chromatography to improve the yield, but normally 30 minutes to 40 hours.

The amount of an organometallic reagent to be used is preferably 0.8 to 10 moles relative to 1.0 mole of a sulfoxide (1g), and more preferably 1.0 to 5.5 moles. When the amount is 0.8 moles or more, the reaction can fully be produced, and when the amount to be used is 10 mole or less, side reaction can be controlled, thereby controlling reduction in yield and purity and reducing costs.

Furthermore, when a single use of the organometallic reagent fails to achieve a reaction, an activator can be added to improve the reactivity of the sulfoxide (1g). Illustrative example of the activator includes acid anhydride such as acetic anhydride, trifluoro acetic anhydride, and trifluoromethane sulfonate anhydride; acid chloride such as acetyl chloride, methanesulfonylchloride, P-toluenesulfonylchloride, and trifluoromethane sulfonylchloride; and chlorosilane such as trimethylsilyl chloride, and triethylsilyl chloride. When an esterifying agent that can react with an organometallic reagent is used as an activator, a sulfoxide (1g) and an activator are first reacted to preferably prepare a reactive intermediate and react with an organometallic reagent. The amount of an activator to be used is preferably 0 to 10 moles relative to 1.0 mole of a sulfoxide (1g), and more preferably 1.0 to 5.5 moles. The molar quantity is particularly preferably equal to the organometallic reagent. When the amount is 10 moles or less, side reaction can be controlled, thereby controlling reduction in yield and purity and reducing costs.

The reaction mixture is subjected to normal aqueous work-up to obtain a sulfonium salt (1h), and as required, it can be purified according to a conventional method such as recrystallization and chromatography. Furthermore, a target sulfonium salt (1d) can be synthesized by subjecting a sulfonium salt (1h) and a salt ($M^+Z^-$) having a desired anion ($Z^-$) to ion exchange. The ion exchange can readily be conducted by a known method as shown above.

When a sulfonium salt (1d) whose $R^{Xa}$ represents an acid labile group is synthesized, the acid labile group in $R^{Xa}$ may be introduced prior to cationization, or introduced by modifying a sulfonium salt (1h) whose $R^{Xa}$ represents a hydrogen atom. When a sulfonium salt (1d) whose $R^{Xa}$ represents a hydrogen atom is synthesized, this can be achieved after synthesizing a sulfonium salt (1h) whose $R^{Xa}$ represents an acid labile group to remove the acid labile group, or an excessive organometallic reagent may act on sulfoxide while $R^{Xa}$ represents a hydrogen atom for cationization. As reaction conditions in modification, known conditions can be employed in a reaction of a usual modifier and a hydroxy group.

Furthermore, another method for synthesizing the sulfonium salt of the present invention may be a method for synthesizing a target sulfonium salt by subjecting a sulfoxide (1g) to cationization under the action on an aromatic compound in a phosphorus pentaoxide/methane sulfonate solution and conducting ion exchange using a salt having a desired anion. Also, a target sulfonium salt can be synthesized by allowing an aromatic compound (e.g., phenol and naphthol) to act on the sulfoxide (1g) in a methanol solution together with hydrogen chloride gas for cationization and using a salt having a desired anion for ion exchange. These methods are known, as disclosed in JP-A-2012-041320.

Other known methods for synthesizing a cation include a method of cationization using a reaction of silyl enol ether and sulfoxide as disclosed in JP-A-2014-006491, a method of cationization using a reaction of sulfide and a compound having leaving group (e.g., alkane derivative halide) as disclosed in JP-B-3760952 and JP-B-4025039, and a method of cationization using a reaction of iodonium salt and sulfide as disclosed in JP-A-2014-166983.

The sulfonium salt of the present invention thus obtained can provide a chemically amplified resist composition having few defects in photolithography where a high energy beam such as KrF and ArF excimer laser lights, electron beam (EB) by using the sulfonium salt as a photo acid generator, and extreme ultraviolet rays (EUV) is used as a light source, and excellent in lithography performance such as MEF, EL, LWR, and CDU by controlling acid diffusion.

[Resist Composition]

The present invention provides a resist composition including the following components (A) to (C):

(A) the sulfonium salt of the present invention;

(B) base resin; and (C) organic solvent.

The resist composition of the present invention, as required, may include one or more selected from the following components (D) to (G):

(D) a photo acid generator other than the component (A);

(E) a quencher;

(F) a surfactant; and (G) other components.

(A) sulfonium salt

The sulfonium salt of the component (A) used in the resist composition of the present invention is added as a photo acid generator. The amount of the sulfonium salt of the component (A) is preferably 0.1 to 40 parts by mass relative to 100 parts by mass of (B) a base resin, and more preferably 0.5 to 20 parts by mass. When the amount to be blended is a lower limit or more, it fully functions as a photo acid generator, and shows the action of diffusion control, and when the amount is an upper limit or less, performance degradation such as mixture of foreign substances can, due to insufficient solubility, be controlled.

(B) Base Resin

The base resin of the component (B) used in the resist composition of the present invention is preferably a polymer including a repeating unit represented by the following general formula (6) and a repeating unit represented by the following general formula (7),

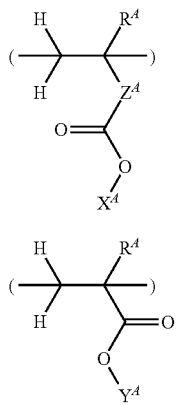

(6)

(7)

wherein, $R^A$ represents any of a hydrogen atom, a fluorine atom, a methyl group, or a trifluoromethyl group; $Z^A$ represents any of a single bond, a phenylene group, a naphthylene group, or a (main chain) —C(=O)—O—Z'—; Z' represents a linear, a branched, or a cyclic alkylene group having 1 to 10 carbon atoms optionally containing any of a hydroxy group, an ether bond, an ester bond, or a lactone ring, a phenylene group, or a naphthylene group; $X^A$ represents an acid labile group; and $Y^A$ represents a hydrogen atom, or a polar group having one or more structures selected from a hydroxy group, a cyano group, a carbonyl group, a carboxyl group, an ether bond, an ester bond, a sulfonic ester bond, a carbonate bond, a lactone ring, a sultone ring, and a carboxylic acid anhydride.

$X^A$ in the general formula (6) represents an acid labile group. The acid labile group is not particularly restricted, but illustrative example thereof includes a tertiary alkyl group having 4 to 20 carbon atoms, a trialkylsilyl group each having an alkyl group as an alkyl group having 1 to 6 carbon atoms, and an oxoalkyl group having 4 to 20 carbon atoms. The specific structures of these acid labile groups are described in detail in JP-A-2014-225005 paras. [0016] to [0035].

$Z^A$ in the general formula (6) represents any of a single bond, a phenylene group, a naphthylene group, or a (main chain) —C(=O)—O—Z'—, preferably a single bond. Illustrative example of the structure having an alternative to $Z^A$ in the general formula (6) includes a structure in JP-A-2014-225005 para [0015], preferably those shown as follows, but the present invention is not restricted thereto. $R^1$ in JP-A-2014-225005 corresponds to $R^A$ in the general formula (6),

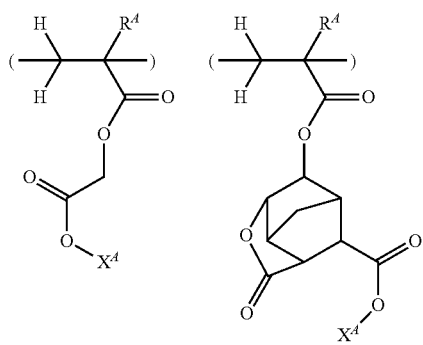

wherein, $R^A$ and $X^A$ represent the same meanings as before.

$Y^A$ in the general formula (7) represents a hydrogen atom, or a polar group having one or more structures selected from a hydroxy group, a cyano group, a carbonyl group, a carboxyl group, an ether bond, an ester bond, a sulfonic ester bond, a carbonate bond, a lactone ring, a sultone ring, and a carboxylic acid anhydride, and any of these structures is allowed.

Illustrative example of the repeating unit represented by the general formula (6) and the repeating unit represented by the general formula (7) includes those described in JP-A-2015-214634 paras. [0013] to [0023] and paras. [0066] to [0109], JP-A-2014-225005 paras. [0014] to [0054], and JP-A-2015-166833 paras. [0029] to [0094]. Particularly preferable structure is an alicyclic group-containing tertiary ester structure in the general formula (6), and hydroxy adamantane (meth)acrylate, a lactone ring, or a sultone ring-containing (meth)acrylate structure in the general formula (7).

Illustrative example of a preferable repeating unit represented by the general formula (6) includes the following structures, but the present invention is not restricted thereto. In the formula, $R^A$ represents the same meaning as before,

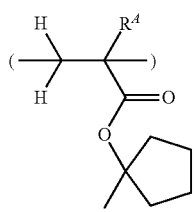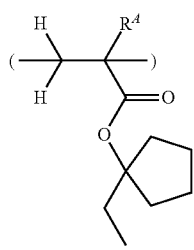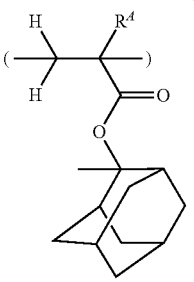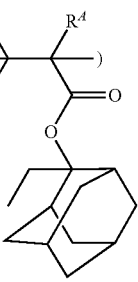
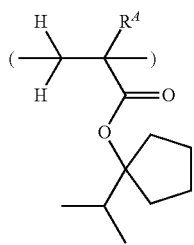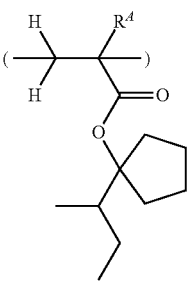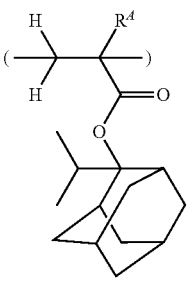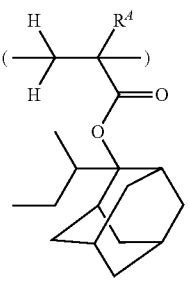
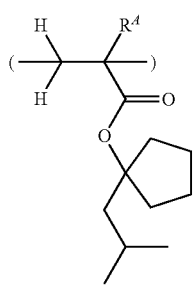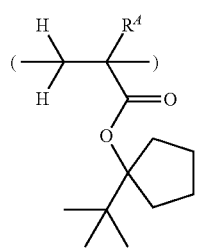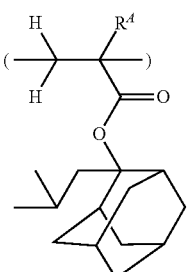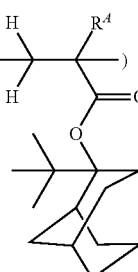
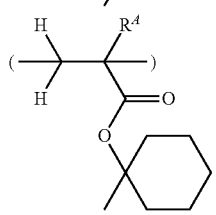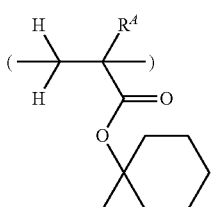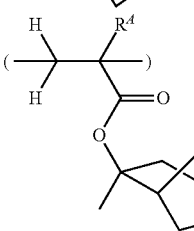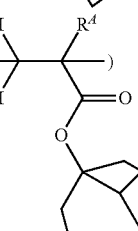
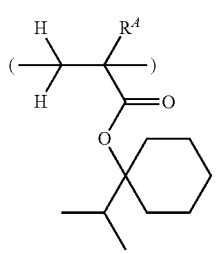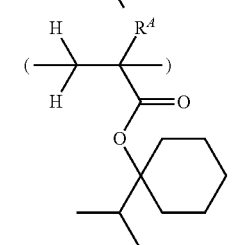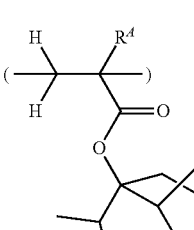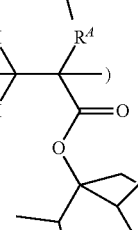
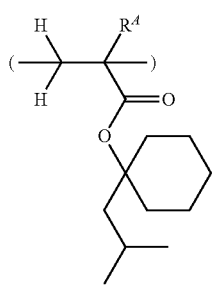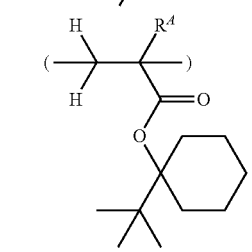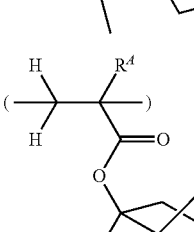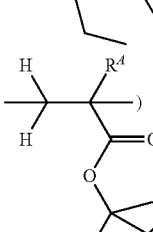
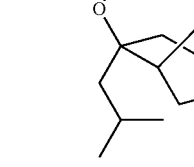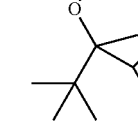

-continued
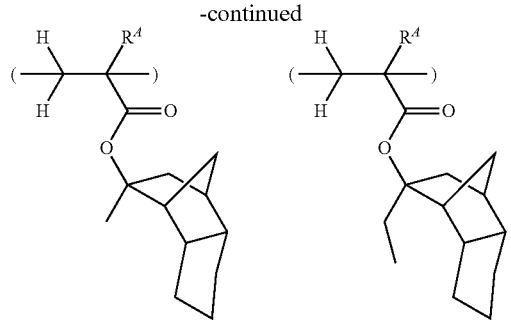 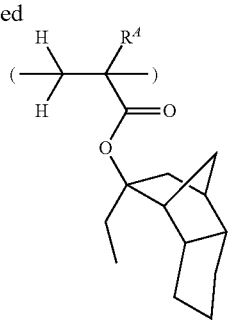
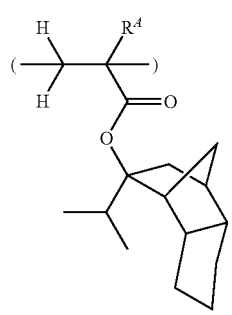 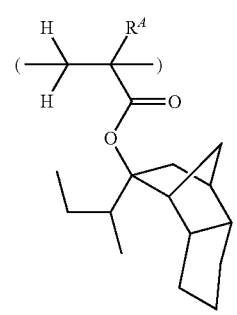
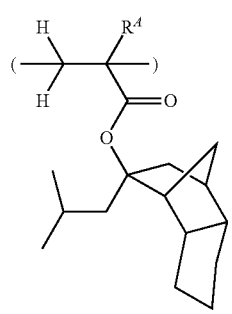 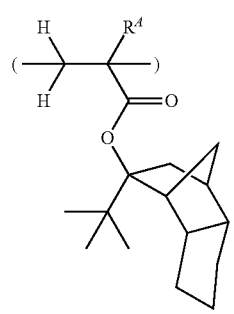
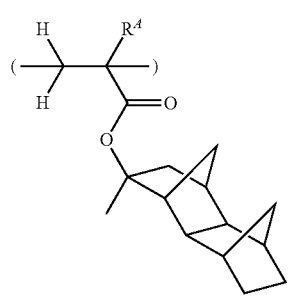
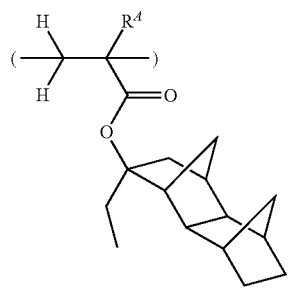
-continued
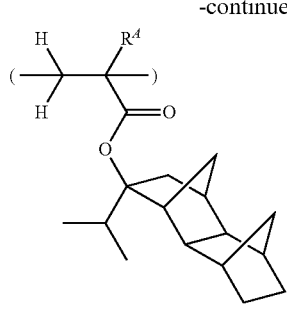
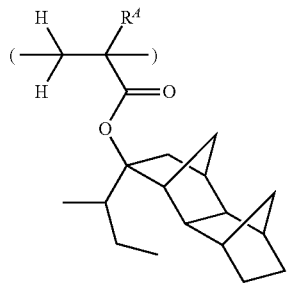
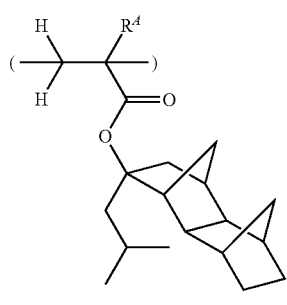
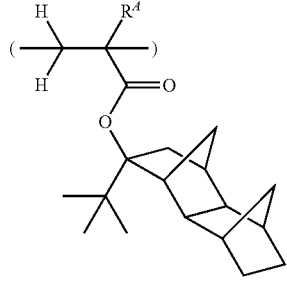
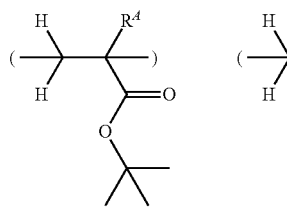 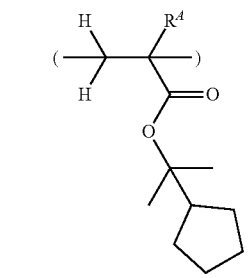
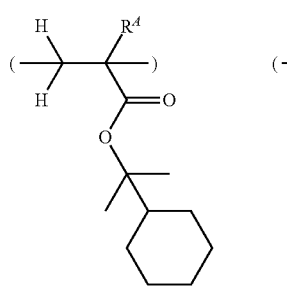 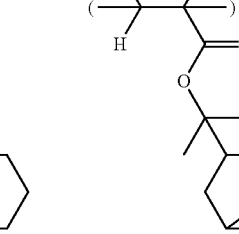

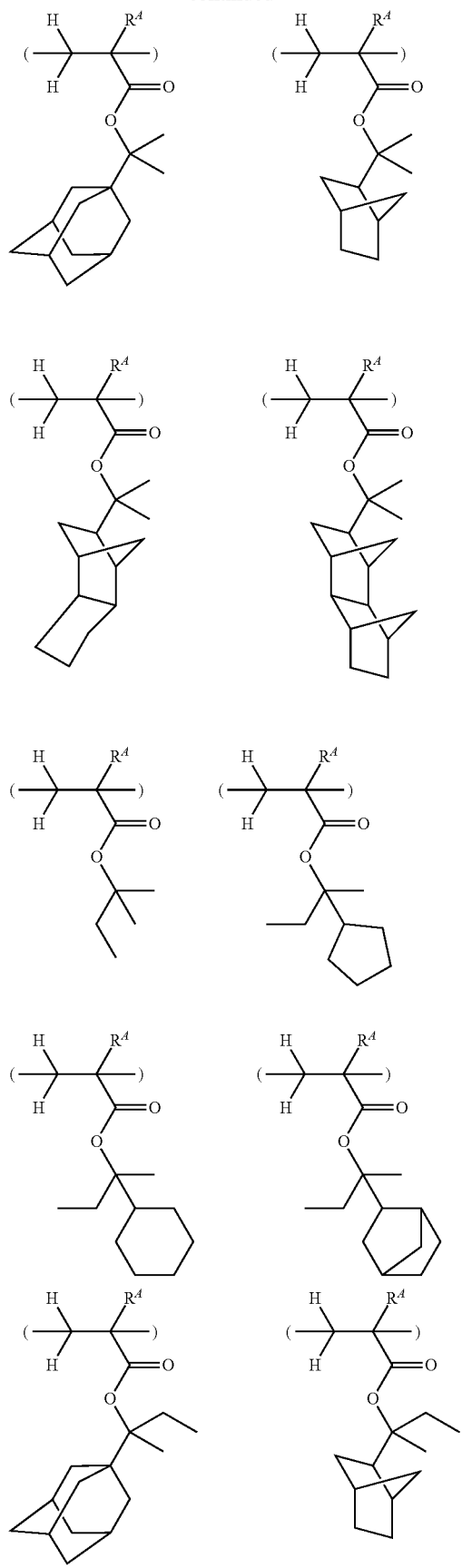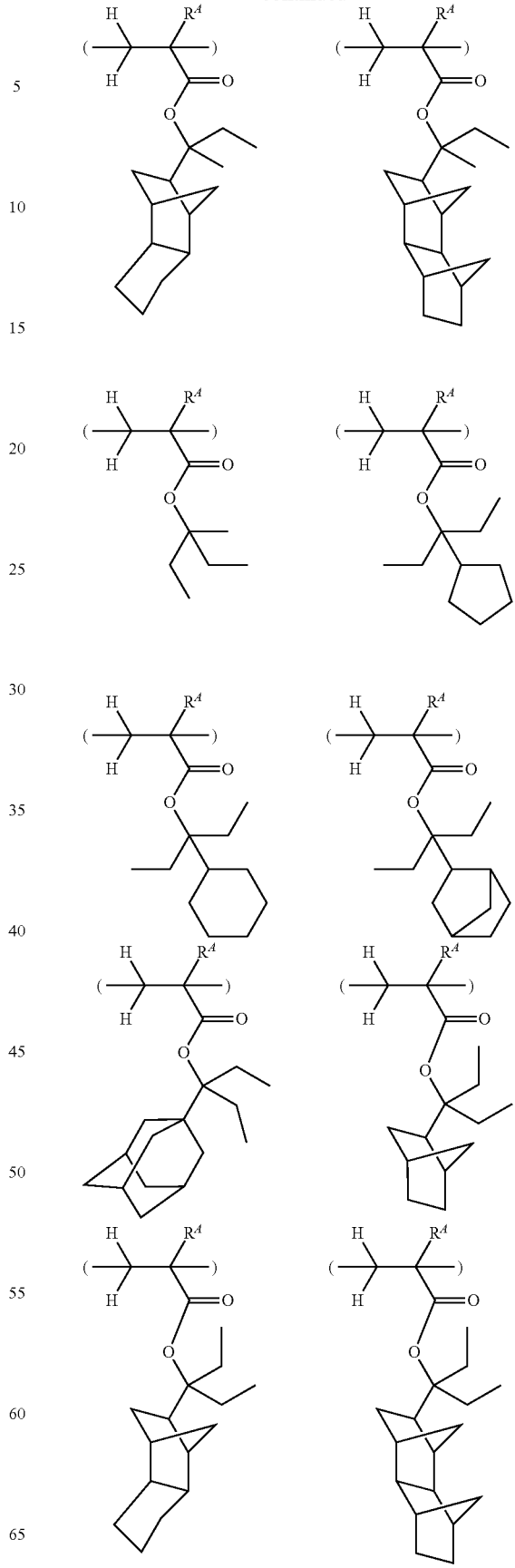

-continued

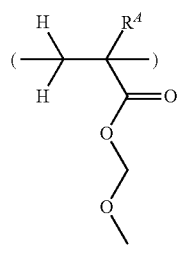 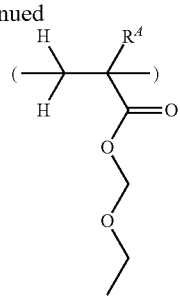

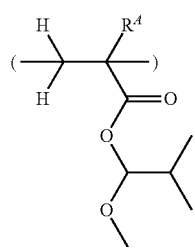 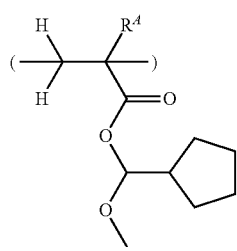

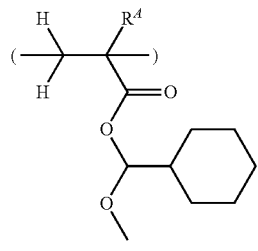 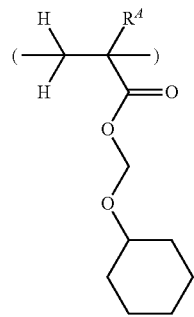

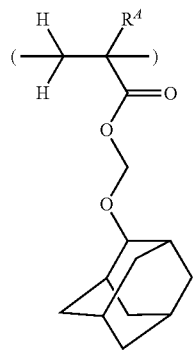 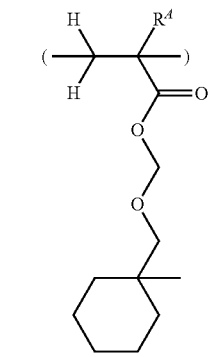

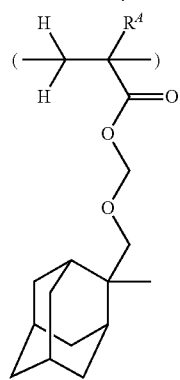 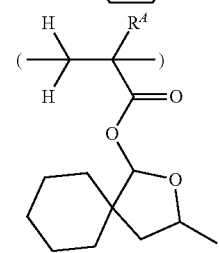

-continued

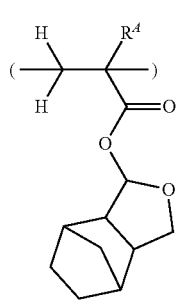 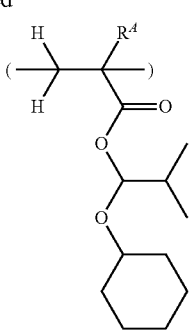

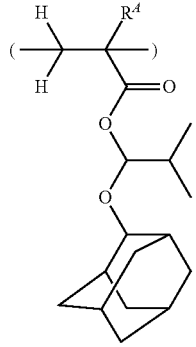 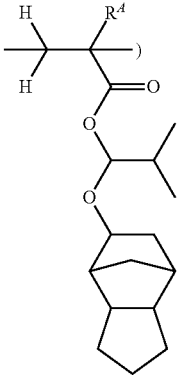

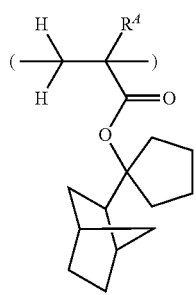 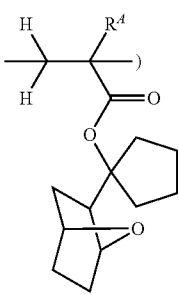

While $Z^A$ represents a single bond in the above example, it can be combined with similar acid labile groups even when $Z^A$ represents other bonds. Illustrative example of the repeating units having $Z^A$ other than a single bond is as shown above.

Among the above-shown acid labile groups ($X^A$), the structure represented by each of the following general formulae (6a), (6b), and (6c) are particularly preferable,

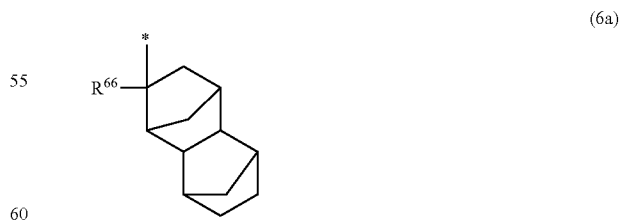

(6a)

(6b)

-continued (6c)

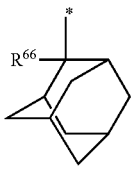

wherein, $R^{66}$ represents a linear, a branched, or a cyclic monovalent hydrocarbon group having 1 to 10 carbon atoms optionally containing a heteroatom; "q" represents 1 or 2; and "*" represents a bond with an ester site in the general formula (6).

When a tertiary alicyclic hydrocarbon group represented by each of the general formulae (6a), (6b), and (6c) is bonded to an ester site, steric repulsion makes higher ability to decompose acid than other tertiary alkyl groups such as a tert-butyl group and a tert-amyl group. Accordingly, when the tertiary alicyclic hydrocarbon group is used as a unit of change in polarity of a resist, the dissolution contrast between an exposed area and a non-exposed area increases. A resist composition, both using a unit of change in polarity represented by the general formula (6) having the partial structure as an acid labile group and the sulfonium salt of the present invention, provides significantly high contrast. In addition, the rate of dissolution on the boundary surface of an exposed area and a non-exposed area is made uniform by the effect of a partial structure represented by the general formula (1). The resulting patterns have few defects, are excellent in lithography performance such as LWR and rectangle property.

Illustrative preferable example of a repeating unit represented by the general formula (7) includes the following structures, but the present invention is not restricted thereto. In the formula, $R^4$ represents the same meaning as before,

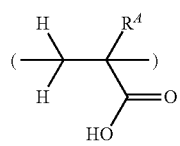 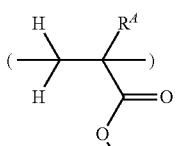

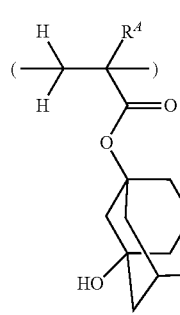 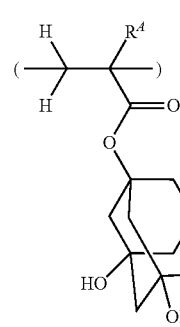

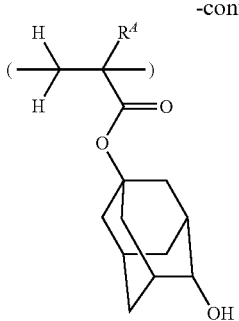 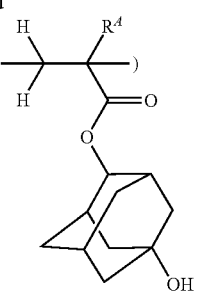

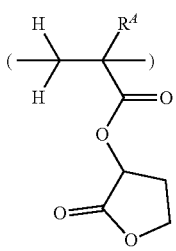 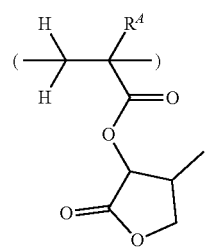

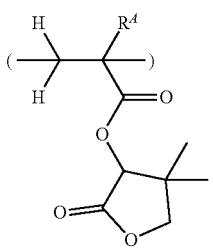 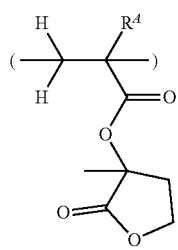

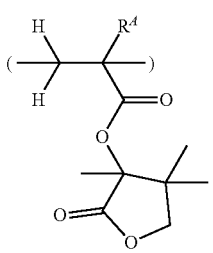 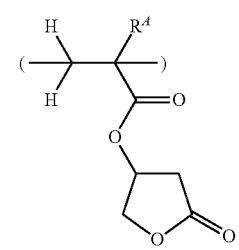

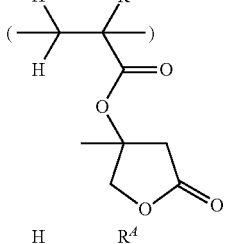 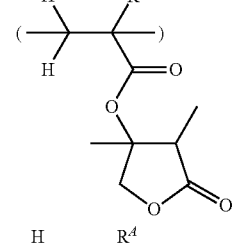

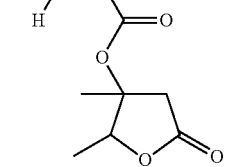 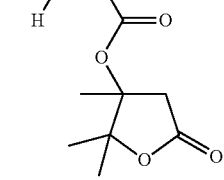

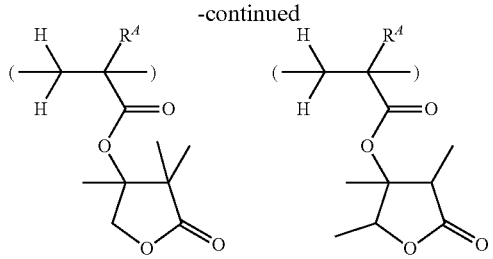
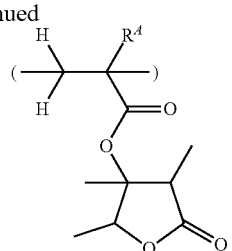
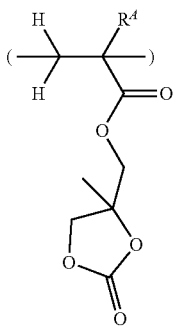
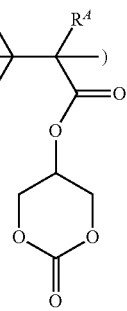
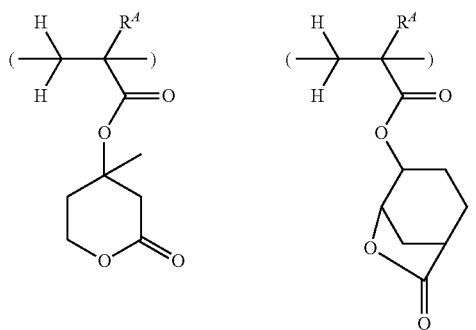
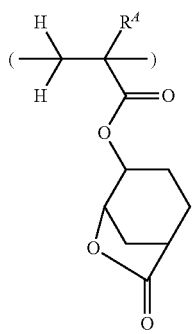
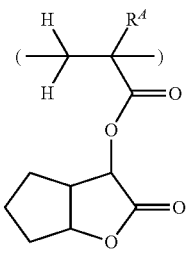
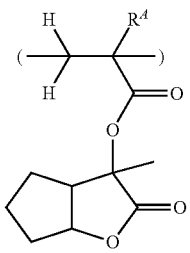
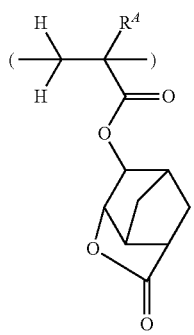
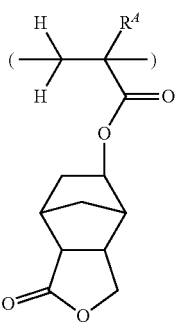
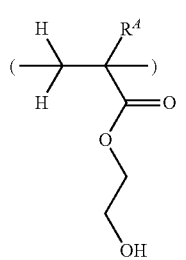
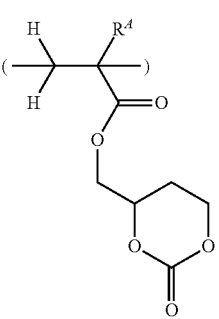
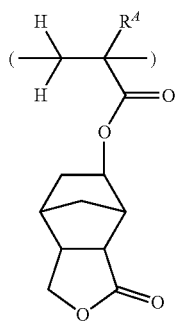
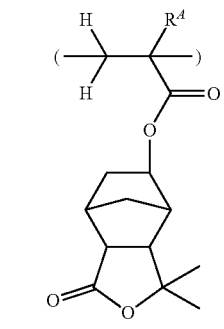
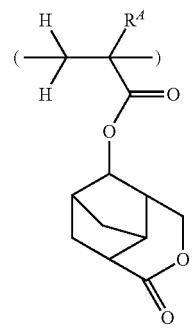
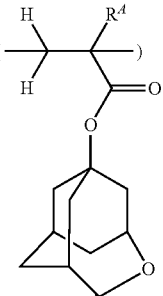
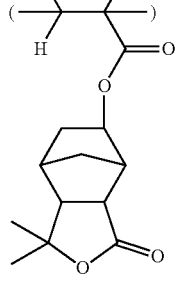
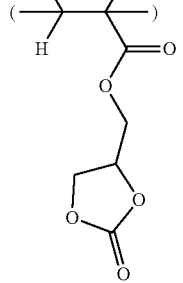
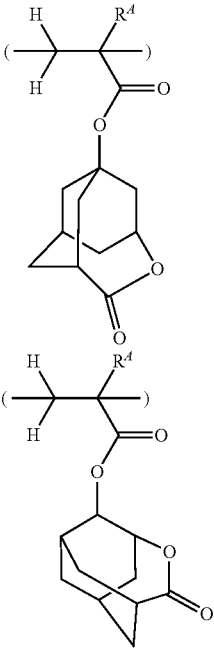

81
-continued
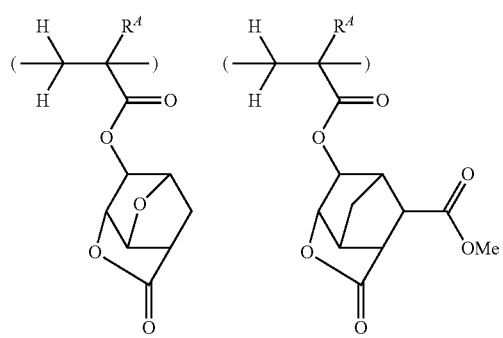
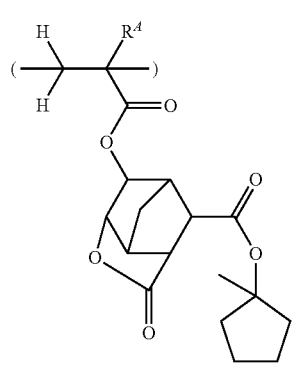
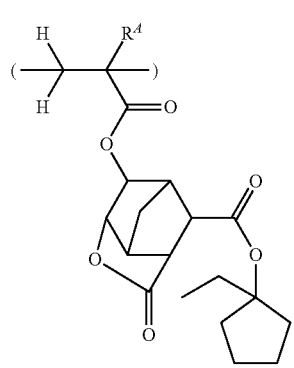
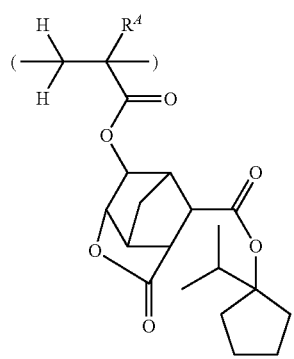
82
-continued
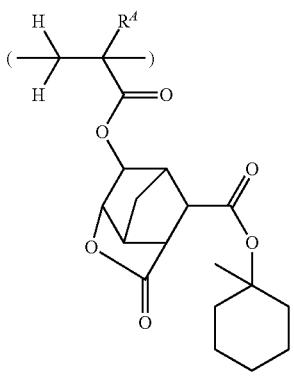
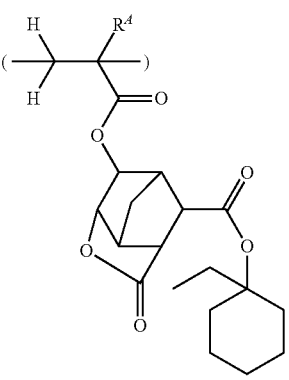
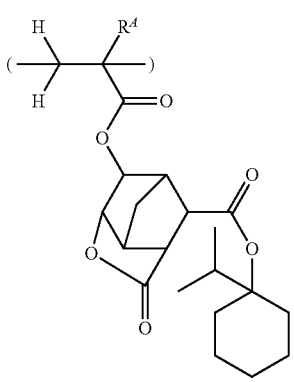
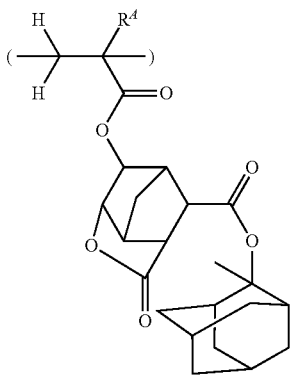

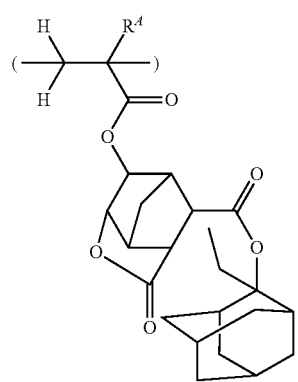
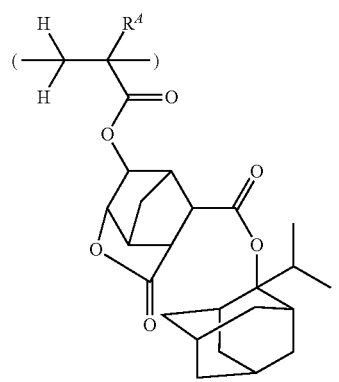
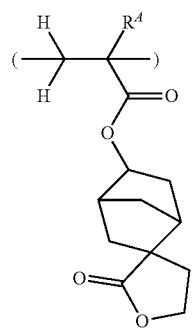
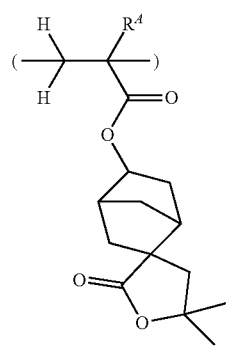
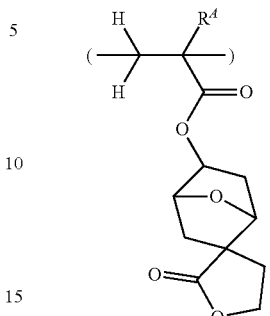
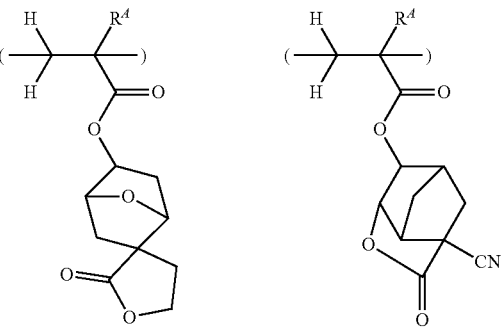
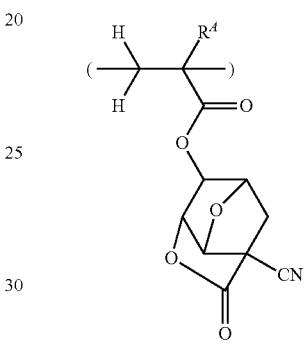
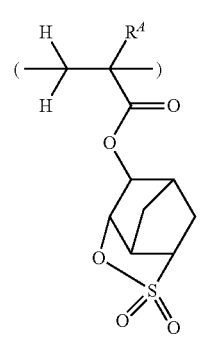
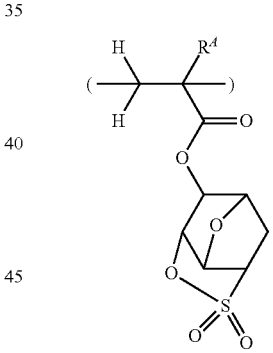
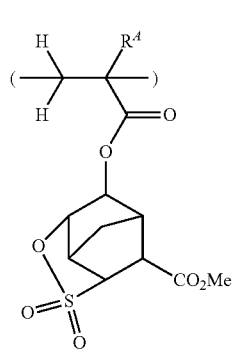
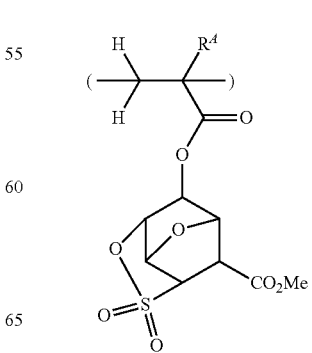
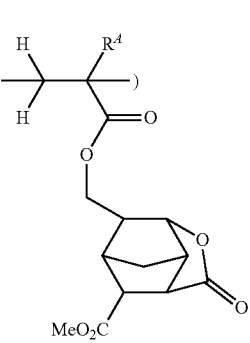

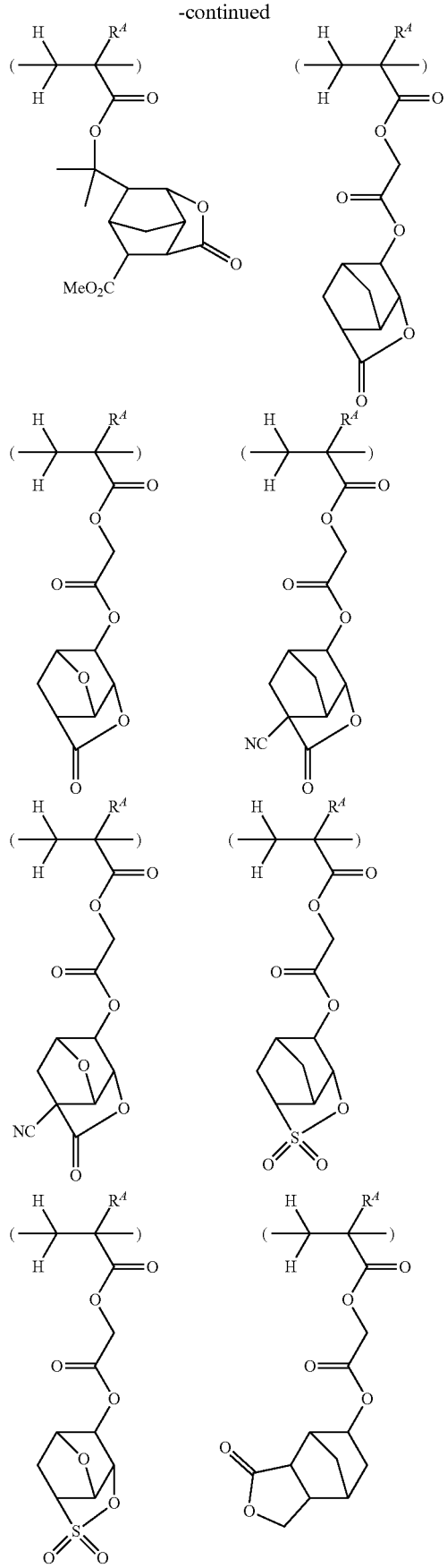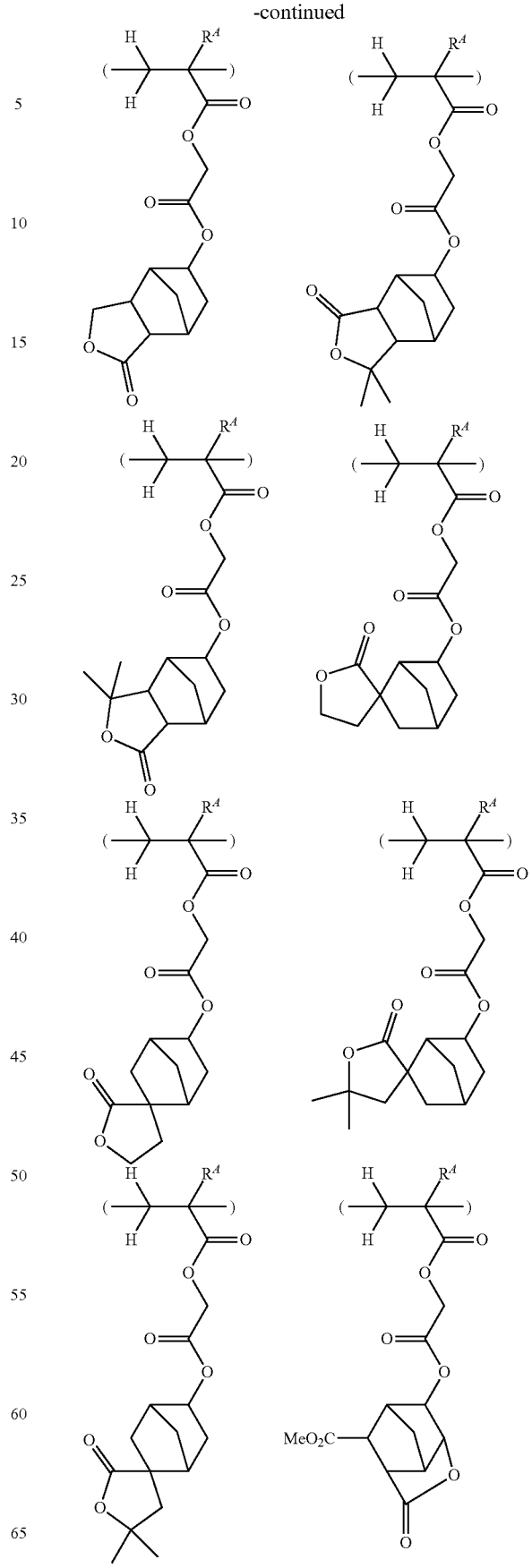

-continued

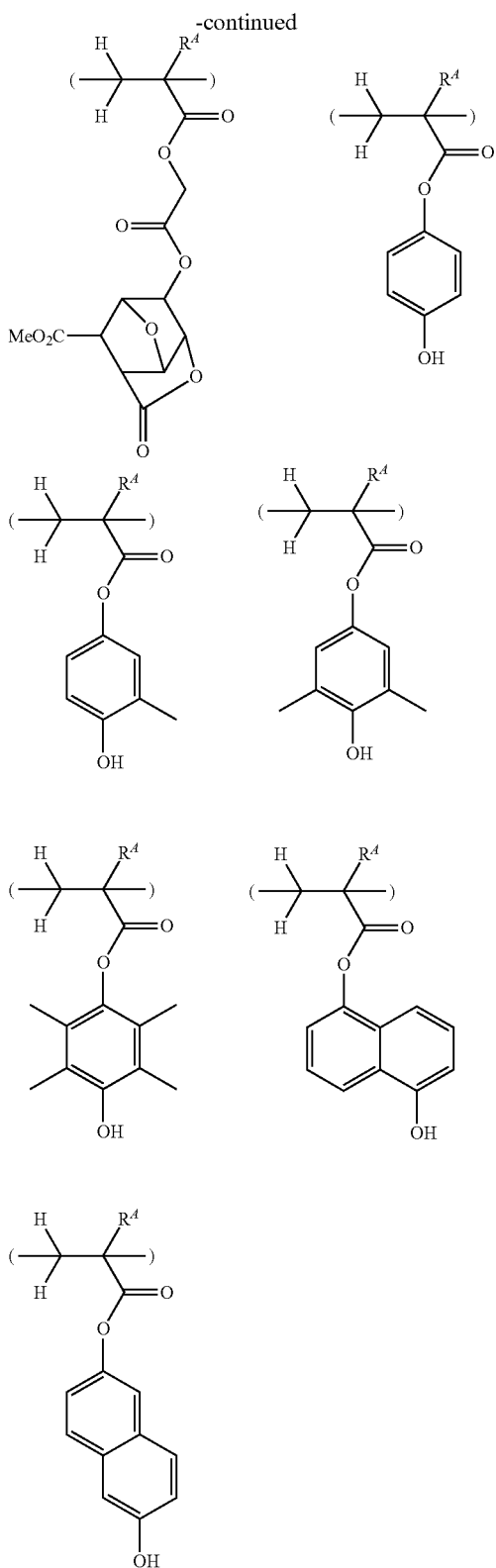

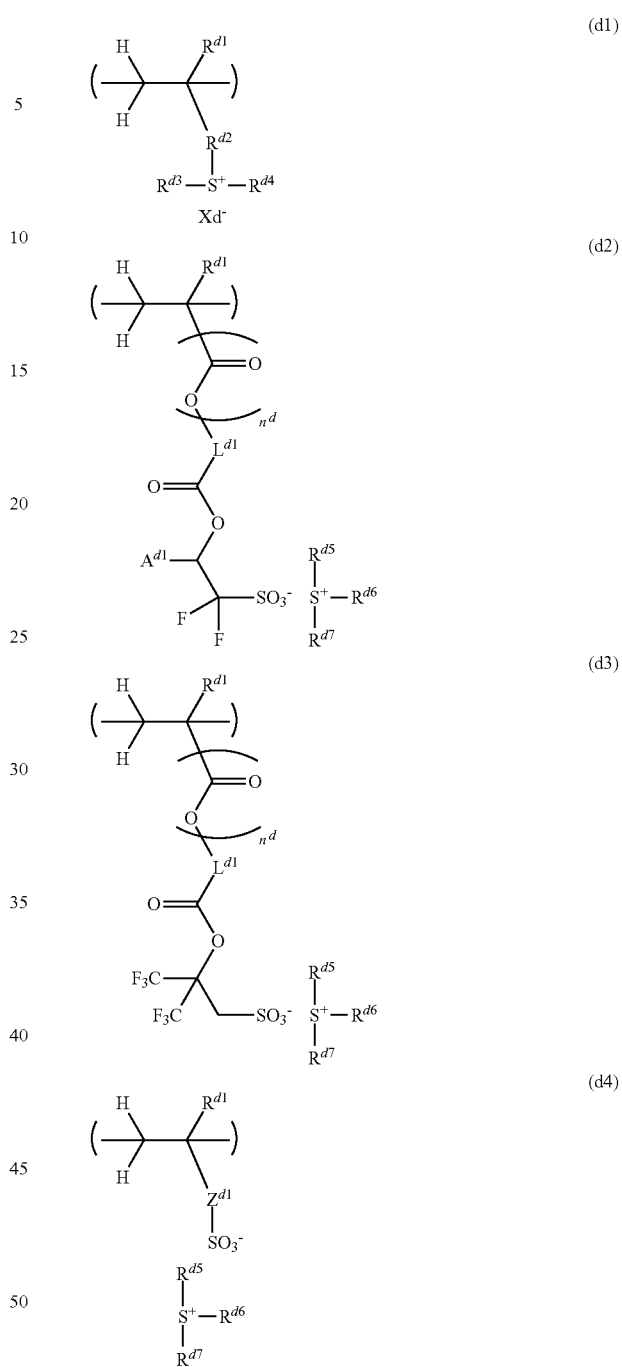

Preferably, the base resin of the component (B) includes a repeating unit represented by the general formula (6) and a repeating unit represented by the general formula (7), and may include a repeating unit represented by any of the following general formula (d1), (d2), (d3), or (d4) as other repeating unit, wherein, $R^{d1}$ represents a hydrogen atom, a fluorine atom, a methyl group, or a trifluoromethyl group; $R^{d2}$ represents a single bond, a phenylene group, $-O-R^{d10}-$ or $-C(=O)-Y^{d1}-R^{d10}-$; $Y^{d1}$ represents an oxygen atom or a $-NH-$ group; $R^{d10}$ represents a linear, a branched, or a cyclic alkylene group, an alkenylene group, or a phenylene group having 1 to 20 carbon atoms optionally containing a heteroatom; each of $R^{d3}$, $R^{d4}$, $R^{d5}$, $R^{d6}$, and $R^{d7}$ independently represents a linear, a branched, or a cyclic monovalent hydrocarbon group having 1 to 20 carbon atoms optionally containing a heteroatom; two or more of $R^{d2}$, $R^{d3}$, and $R^{d4}$ are bonded to form a ring together with a sulfur atom bonded thereto; two or more of $R^{d5}$, $R^{d6}$, and $R^{d7}$ are bonded to form a ring together with a sulfur atom bonded thereto; $Xd^-$ represents a non-nucleophilic counter ion; $A^{d1}$ represents a hydrogen atom or a trifluoromethyl group; $L^{d1}$ represents a single bond, or a linear, a branched, or a cyclic divalent hydrocarbon group having 1 to 20 carbon atoms optionally containing a heteroatom; $n^d$ represents 0 or 1, and when $L^{d1}$ represents a single bond, $n^d$ represents 0; $Z^{d1}$ represents a single bond, a methylene group, an ethylene group, a phenylene group, a fluorinated phenylene group, —O—$R^{d10}$—, or —C(=O)—$Y^{d1}$—$R^{d11}$—, wherein $Y^{d1}$ represents the same meaning as before; and $R^{d11}$ represents a phenylene group, which may be substituted.

Preferably, each of $R^{d2}$ to $R^{d7}$ in the general formulae (d1) to (d4) independently represents a structure including a phenyl group or a phenylene group, which preferably is bonded to in the formula.

$Xd^-$ in the general formula (d1) represents a non-nucleophilic counter ion, and illustrative example thereof includes a halide ion such as a chloride ion and a bromide ion; fluoroalkyl sulfonate such as triflate, 1,1,1-trifluoroethane sulfonate, and nonafluorobutane sulfonate; aryl sulfonate such as tosylate, benzene sulfonate, 4-fluorobenzene sulfonate, and 1,2,3,4,5-pentafluorobenzene sulfonate; alkyl sulfonate such as mesylate and butane sulfonate; imide acid such as bis(trifluoromethylsulfonyl)imide, bis(perfluoroethylsulfonyl)imide, and bis(perfluorobutylsulfonyl)imide; and methide acid such as tris(trifluoromethylsulfonyl)methide and tris(perfluoroethylsulfonyl)methide, preferably an anion represented by the following general formula (d5) or (d6),

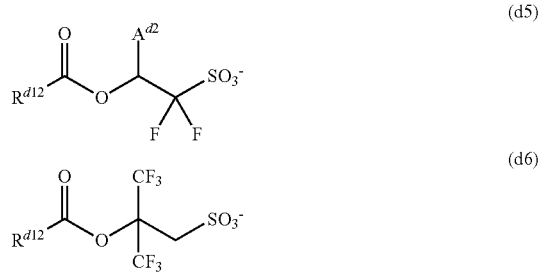

wherein, $R^{d12}$ represents a linear, a branched, or a cyclic monovalent hydrocarbon group having 1 to 40 carbon atoms optionally containing a heteroatom; and $A^{d2}$ represents a hydrogen atom or a trifluoromethyl group.

Illustrative example of the anion represented by the general formula (d5) includes an anion represented by the formula (4a) and an anion disclosed in JP-A-2014-177407 paras. [0100] to [0101]. Illustrative example of the anion represented by the general formula (d6) includes an anion represented by the formula (4b) and an anion disclosed in JP-A-2010-215608 paras. [0080] to [0081].

Illustrative example of the anion site in the general formula (d2) includes an anion site disclosed in JP-A-2014-177407 paras. [0021] to [0026]. When $A^{d1}$ represents a hydrogen atom, illustrative example of the anion site includes an anion site disclosed in JP-A-2010-116550 paras. [0021] to [0028], and when $A^{d1}$ represents a trifluoromethyl group, illustrative example of the anion site includes an anion site disclosed in JP-A-2010-077404 paras. [0021] to [0027]. The cation site in the general formula (d2) is described in detail in JP-A-2008-158339 para. [0223].

Illustrative example of the anion site in the general formula (d3) includes an anion site in which a —CH($A^{d1}$)$CF_2SO_3$— portion is substituted by —C($CF_3$)$_2CH_2SO_3$— in an anion site in the general formula (d2).

Illustrative example of the sulfonium cation in each of the general formulae (d2) to (d4) includes a cation disclosed in JP-A-2008-158339 paras. [0223] and [0102].

The base resin of the component (B) preferably includes a repeating unit represented by the general formula (6) and a repeating unit represented by the general formula (7), and as required, may include a repeating unit represented by any of the general formula (d1), (d2), (d3), or (d4), and as other units, may include a repeating unit having a structure whose hydroxyl group is protected with an acid labile group as another repeating unit. Illustrative example of the repeating unit having a structure whose hydroxyl group is protected with an acid labile group includes one or more structure whose hydroxyl group is protected, and they are not particularly restricted as long as a protective group is decomposed by acid action to produce a hydroxyl group, but includes those disclosed in JP-A-2014-225005 paras. [0055] to [0065] and JP-A-2015-214634 paras. [0110] to [0115].

Furthermore, other repeating units, such as a repeating unit having an oxirane ring or an oxetane ring, may be copolymerized with the base resin of the component (B). This copolymerization improves residual resist characteristics of an exposed area and etching resistance due to crosslinking of the exposed area. The base resin of the component (B) may contain a repeating unit from substituted acrylate ester such as methyl methacrylate, methyl crotonate, dimethyl maleate, and dimethyl itaconate; unsaturated carboxylic acid such as maleic acid, fumaric acid, and itaconic acid; cyclic olefin such as norbornene, norbornene derivative, and tetracyclo[6.2.1.1$^{3,6}$.0$^{2,7}$]dodecen derivative; unsaturated acid anhydride such as itaconic acid anhydride; a vinyl aromatic compound such as styrene, vinyl naphthalene, hydroxyl styrene, hydroxyvinyl naphthalene, and 4-tert-butoxy styrene; and other monomers. Illustrative example of a hydrogen additive of a ring-opening metathesis polymer may be disclosed in JP-A-2003-066612. Illustrative example of the repeating unit that may be copolymerized described above includes a repeating unit disclosed in JP-A-2015-214634 paras. [0120] to [0132], but the present invention is not restricted thereto.

The weight average molecular weight of the base resin of the component (B) is preferably 1,000 to 500,000, and more preferably 3,000 to 100,000. So long as the weight average molecular weight is within the range, significant reduction in etching resistance, or reduction in resolution due to no difference in rate of dissolution before and after exposure can be prevented. The method for measuring a molecular weight is gel permeation chromatography (GPC) in terms of polystyrene. The degree of dispersion (Mw/Mn) is preferably 1.20 to 2.50, particularly 1.30 to 1.80.

Illustrative example of the method for synthesizing a base resin (polymer) of the component (B) includes a method for subjecting one or more desired monomers out of monomers that provide each repeating unit to heat polymerization by adding an initiator of radical polymerization in an organic solvent to obtain a copolymer. Such a polymerization method is disclosed in detail in JP-A-2015-214634 paras. [0134] to [0137]. The acid labile group may be the one introduced into a monomer, protected or partially protected after polymerization.

In the base resin of component (B), a preferable ratio of each repeating unit obtained from each monomer can be in the following range (mole %), but the present invention is not restricted thereto.

(I) The ratio of one or more structural units represented by the general formula (6) is 1 to 80 mole %, preferably 5 to 70 mole %, and more preferably 10 to 60 mole %,
(II) the ratio of one or more structural units represented by the general formula (7) is 20 to 99 mole %, preferably 30 to 95 mole %, and more preferably 40 to 90 mole %, and as required,
(III) the ratio of one or more structural units represented by any one of the general formulae (d1) to (d4) is 0 to 30 mole %, preferably 0 to 20 mole %, and more preferably 0 to 15 mole %, and as required, and
(IV) the ratio of one or more structural units based on other monomers is 0 to 80 mole %, preferably 0 to 70 mole %, and more preferably 0 to 60 mole %.

(C) Organic Solvent

The components (A) and (B) can be dissolved into the organic solvent of the component (C) used in the resist composition of the present invention, preferably the later-described components (D) to (G) can be dissolved into the organic solvent. Illustrative example of the organic solvent is disclosed, for example, in JP-A-2008-111103 paras. [0144] to [0145], and includes ketone such as cyclohexanone and methyl-2-n-amyl ketone; alcohol such as 3-methoxy butanol, 3-methyl-3-methoxy butanol, 1-methoxy-2-propanol, 1-ethoxy-2-propanol, and diacetone alcohol; ether such as propylene glycol monomethylether, ethylene glycol monomethylether, propylene glycol monoethylether, ethylene glycol monoethylether, propylene glycol dimethylether, and diethylene glycol dimethylether; ester such as propylene glycol monomethylether acetate, propylene glycol monoethylether acetate, ethyl lactate, ethyl pyruvate, butyl acetate, 3-methoxy methyl propionate, 3-ethoxy ethyl propionate, tert-butyl acetate, tert-butyl propionate, and propylene glycol monotert-butylether acetate; and lactone such as γ-butyrolactone; and a mixed solvent thereof. When an acetal-based acid labile group is used, an alcohol-based solvent of a high boiling point, such as diethylene glycol, propylene glycol, glycerine-1,4-butanediol, and 1,3-butanediol, can be added to accelerate acetal deprotection reaction.

In the present invention, among these organic solvents, 1-ethoxy-2-propanol, propylene glycol monomethylether acetate, cyclohexanone, γ-butyrolactone, and a mixed solvent thereof, which are particularly excellent in solubility of a photo acid generator in a resist component, are preferably used.

Preferably, the amount of the organic solvent of the component (C) is 100 to 8,000 parts by mass, relative to 100 parts by mass of a base resin of the component (B), particularly 400 to 5,000 parts by mass.

(D) Photo Acid Generator

The resist composition of the present invention may include, as a component (D), a photo acid generator other than the component (A) (that is, a photo acid generator other than a sulfonium salt having a partial structure represented by the formula (1)). Any photo acid generator can be used so long as it is a compound that can generate acid by high energy beam irradiation. Illustrative desirable example of the photo acid generator includes a sulfonium salt, an iodonium salt, sulfonyldiazo methane, N-sulfonyl oxydicarboxy imide, O-arylsulfonyl oxime, and O-alkylsulfonyl oxime, and these can be used singularly or mixed in combination with two or more components. Specifically, they include a compound disclosed in JP-A-2007-145797 paras. [0102] to [0113], a compound disclosed in JP-A-2008-111103 pares. [0122] to [0142], a compound disclosed in JP-A-2014-001259 paras. [0081] to [0092], a compound disclosed in JP-A-2012-041320, a compound disclosed in JP-A-2012-153644, a compound disclosed in JP-A-2012-106986, and a compound disclosed in JP-A-2016-018007. The partial fluorinated sulfonate-generating photo acid generator disclosed in the patent documents, particularly in ArF lithography, has an appropriate strength or diffusion length of a generated acid, and can preferably be used. When it is used with an iodonium salt, the cation may preferably be a diphenyliodonium cation or a di-tert-butylphenyliodonium cation.

Illustrative preferable example of the photo acid generator of the component (D) includes a photo acid generator represented by the following general formula (8) or (9),

(8)

wherein, each of $R^{100}$, $R^{200}$, and $R^{300}$ independently represents a linear, a branched, or a cyclic monovalent hydrocarbon group having 1 to 20 carbon atoms optionally containing a heteroatom, and any two or more of $R^{100}$, $R^{200}$, and $R^{300}$ may be bonded to form a ring together with a sulfur atom in the formula; and $X^{a-}$ represents an anion represented by any of the following general formula (8A), (8B), (8C), or (8D),

(8A)

(8B)

(8C)

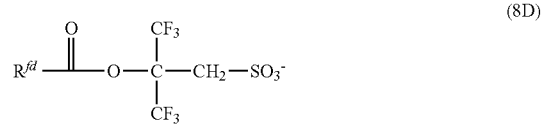

(8D)

wherein, each of $R^{fa1}$, $R^{fb1}$, $R^{fb2}$, $R^{fc1}$, $R^{fc2}$, and $R^{fc3}$ independently represents a fluorine atom, or a linear, a branched, or a cyclic monovalent hydrocarbon group having 1 to 40 carbon atoms optionally containing a heteroatom, and $R^{fb1}$ and $R^{fb2}$, and $R^{fc1}$ and $R^{fc2}$ may be bonded to form a ring together with a carbon atom bonded thereto and an atom therebetween; $R^{fd}$ represents a linear, a branched, or a cyclic monovalent hydrocarbon group having 1 to 40 carbon atoms optionally containing a heteroatom,

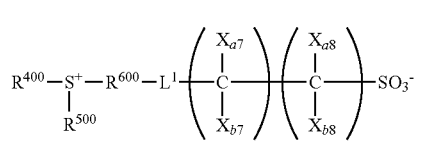

(9)

wherein, each of $R^{400}$ and $R^{500}$ independently represents a linear, a branched, or a cyclic monovalent hydrocarbon group having 1 to 30 carbon atoms optionally containing a heteroatom; $R^{600}$ represents a linear, a branched, or a cyclic divalent hydrocarbon group having 1 to 30 carbon atoms optionally containing a heteroatom, and any two or more of Rim, $R^{500}$, and $R^{600}$ may be bonded to form a ring together with a sulfur atom in the formula; $L^1$ represents a single bond, an ether bond, or a linear, a branched, or a cyclic divalent hydrocarbon group having 1 to 20 carbon atoms optionally containing a heteroatom; each of $X_{a7}$, $X_{b7}$, $X_{a8}$, and $X_{b8}$ independently represents any of a hydrogen atom, a fluorine atom, or a trifluoromethyl group, and one or more of $X_{a7}$, $X_{b7}$, $X_{a8}$, and $X_{b8}$ represent a fluorine atom or a trifluoromethyl group.

Each of $R^{100}$, $R^{200}$, and $R^{300}$ in the general formula (8) independently represents a linear, a branched, or a cyclic monovalent hydrocarbon group having 1 to 20 carbon atoms optionally containing a heteroatom, and any two or more of $R^{100}$, $R^{200}$, and $R^{300}$ may be bonded to form a ring together with a sulfur atom in the formula, and at least one of $R^{100}$, $R^{200}$, and $R^{300}$ preferably includes an aromatic ring. These sulfonium cations are described in detail in JP-A-2014-001259 paras. [0082] to [0085]. Illustrative example thereof includes a cation disclosed in JP-A-2007-145797 paras. [0027] to [0033], a cation disclosed in JP-A-2010-113209 para. [0059], a cation disclosed in JP-A-2012-041320, a cation disclosed in JP-A-2012-153644, and a cation disclosed in JP-A-2012-106986.

The following cations are preferably illustrated, but the present invention is not restricted thereto,

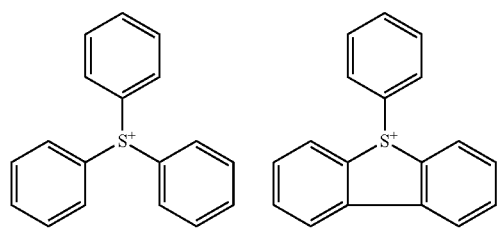

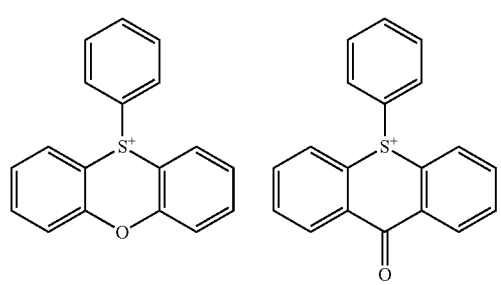

-continued

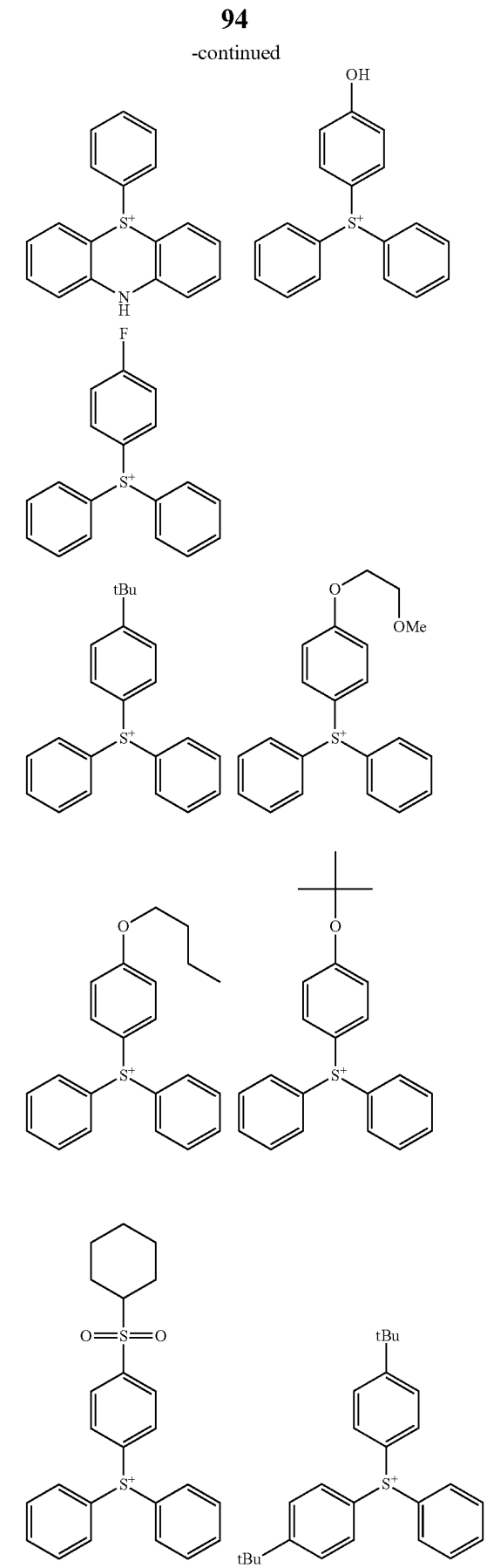

-continued

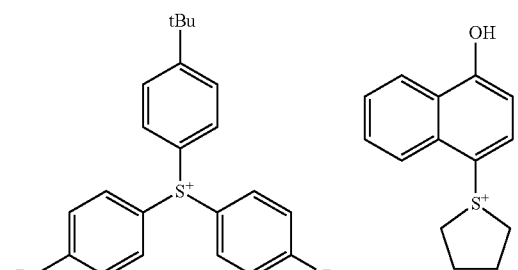

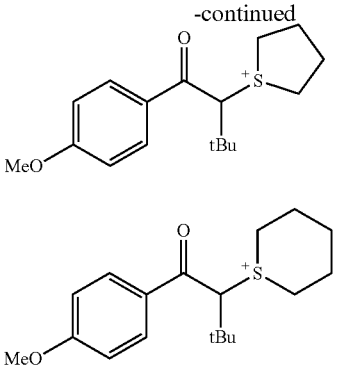

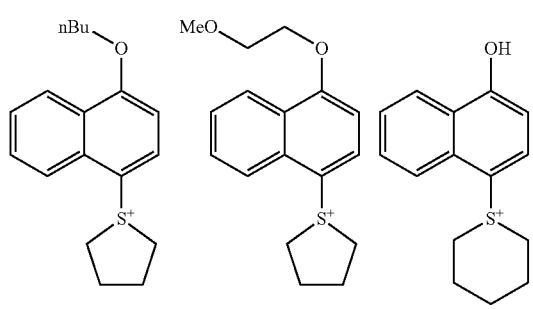

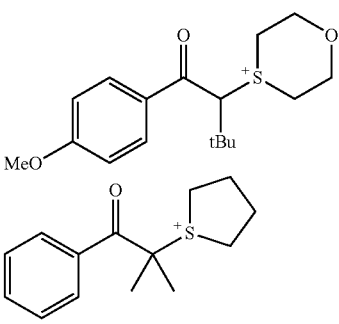

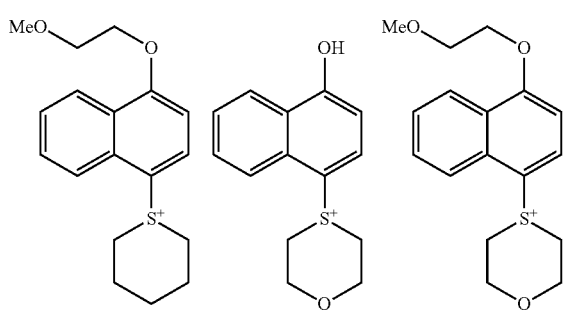

$R^{fa1}$ in the general formula (8A) represents a fluorine atom, or a linear, a branched, or a cyclic monovalent hydrocarbon group having 1 to 40 carbon atoms optionally containing a heteroatom. A preferable structure in the general formula (8A) is the following general formula (8A'),

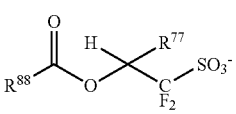

(8A')

wherein, $R^{77}$ represents a hydrogen atom or a trifluoromethyl group; $R^{88}$ represents a linear, a branched, or a cyclic monovalent hydrocarbon group having 1 to 35 carbon atoms, which may substituted by a heteroatom.

$R^{77}$ in the general formula (8A') represents a hydrogen atom or a trifluoromethyl group, and more preferably a trifluoromethyl group. These anions are described in detail in JP-A-2007-145797, JP-A-2008-106045, JP-A-2009-007327, JP-A-2009-258695, and JP-A-2012-181306. Illustrative example thereof includes the anions in these patent documents and an anion represented by the formula (4a).

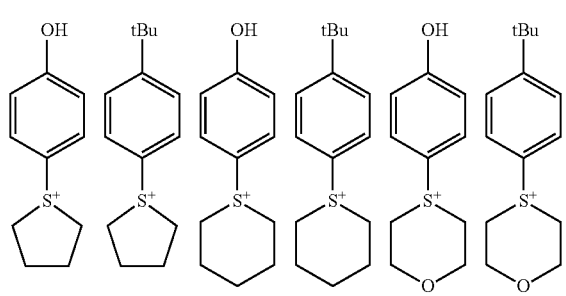

Each of $R^{fb1}$ and $R^{fb2}$ in the general formula (8B) independently represents a fluorine atom, or a linear, a branched, or a cyclic monovalent hydrocarbon group having 1 to 40 carbon atoms optionally containing a heteroatom, preferably a fluorine atom or a linear fluorinated alkyl group having 1 to 4 carbon atoms. $R^{fb1}$ and $R^{fb2}$ are bonded to form a ring together with a carbon atom bonded thereto and an atom (—$CF_2$—$SO_2$—$N^-$—$SO_2$—$CF_2$—) therebetween, and may form a ring structure by a fluorinated ethylene group or a fluorinated propylene group.

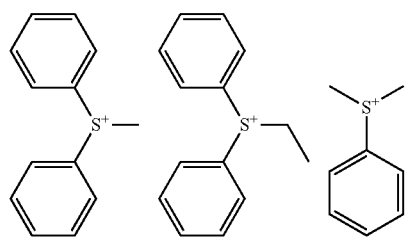

Each of $R^{fc1}$, $R^{fc2}$, and $R^{fc3}$ in the general formula (8C) independently represents a fluorine atom, or a linear, a branched, or a cyclic monovalent hydrocarbon group having 1 to 40 carbon atoms optionally containing a heteroatom, preferably a fluorine atom or a linear fluorinated alkyl group having 1 to 4 carbon atoms. $R^{fc1}$ and $R^{fc2}$ may be bonded to form a ring together with a carbon atom bonded thereto and an atom ($-CF_2-SO_2-C^--SO_2-CF_2-$), and preferably forms a ring structure by a fluorinated ethylene group or a fluorinated propylene group.

$R^{fd}$ in the general formula (8D) represents a linear, a branched, or a cyclic monovalent hydrocarbon group having 1 to 40 carbon atoms optionally containing a heteroatom. These anions are described in detail in JP-A-2010-215608 and JP-A-2014-133723. Illustrative example thereof includes the anions in these patent documents and an anion represented by the formula (4b). The photo acid generator having an anion represented by the general formula (8D) has no fluorine atom at α position of a sulfo group, but has two trifluoromethyl groups at β position. Consequently, it has an acidity strong enough to cut an acid labile group in a resist polymer, which can thus be used as a photo acid generator.

Illustrative example of the anion represented by any of the general formula (8A), (8B), (8C), or (8D) includes the following anions, but the present invention is not restricted thereto. $A^1$ represents a hydrogen atom or a trifluoromethyl group,

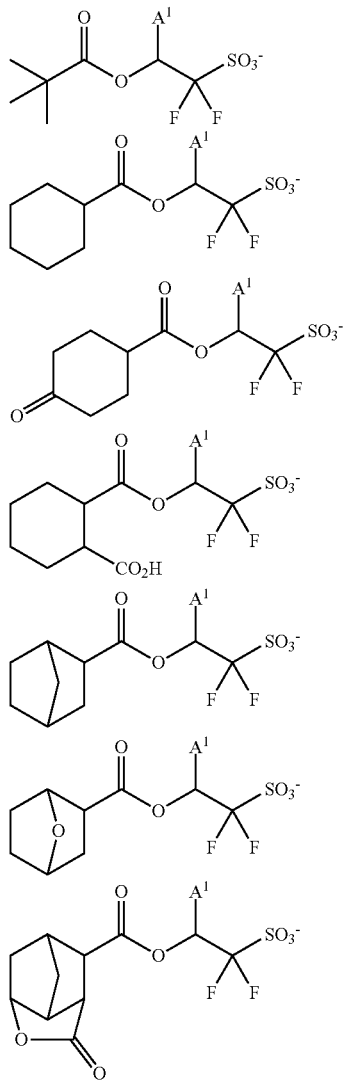

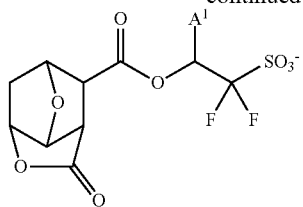

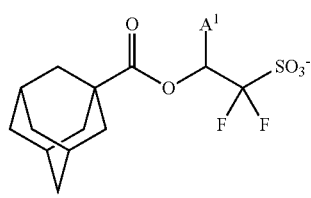

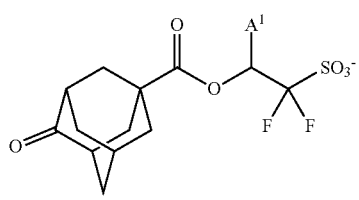

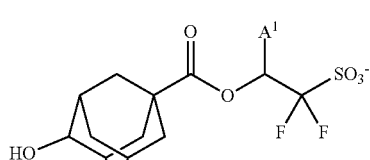

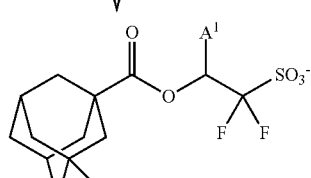

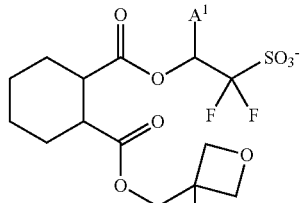

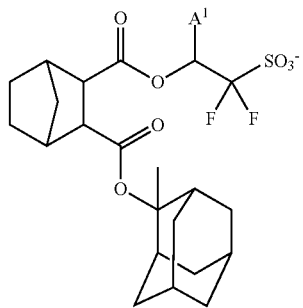

99
-continued
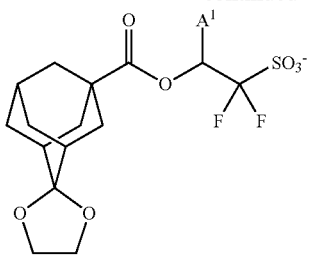
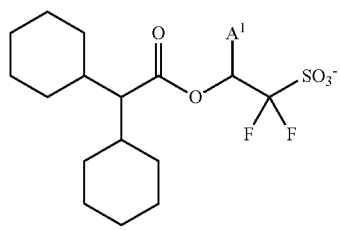
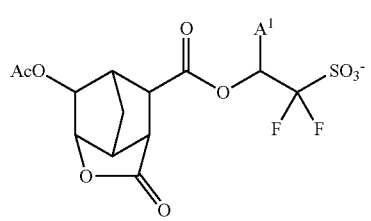
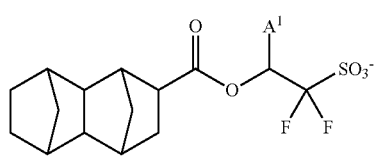
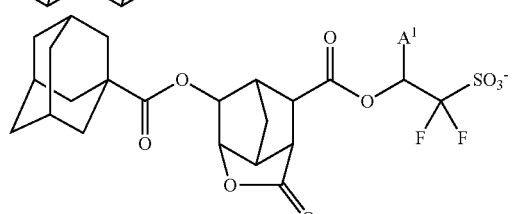
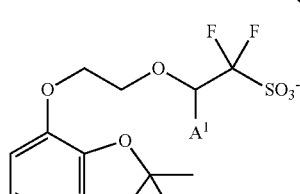
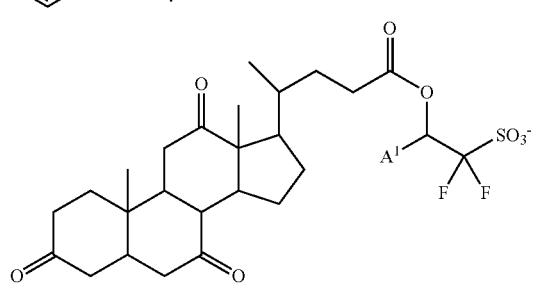
100
-continued
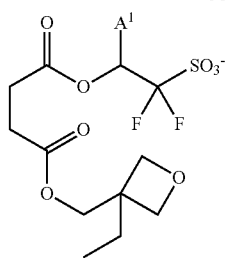
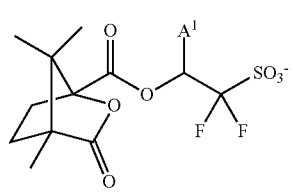
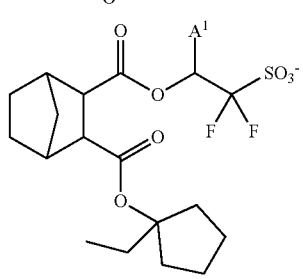
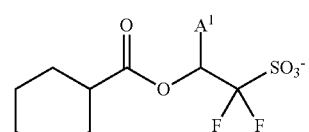
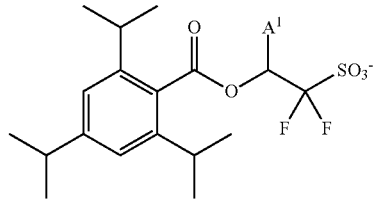
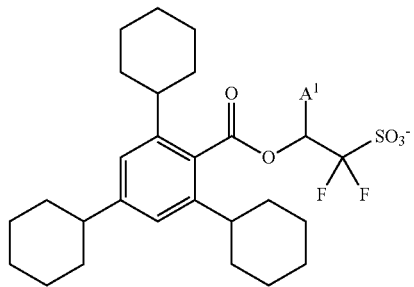
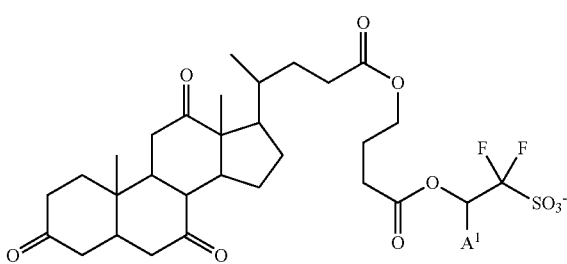

-continued
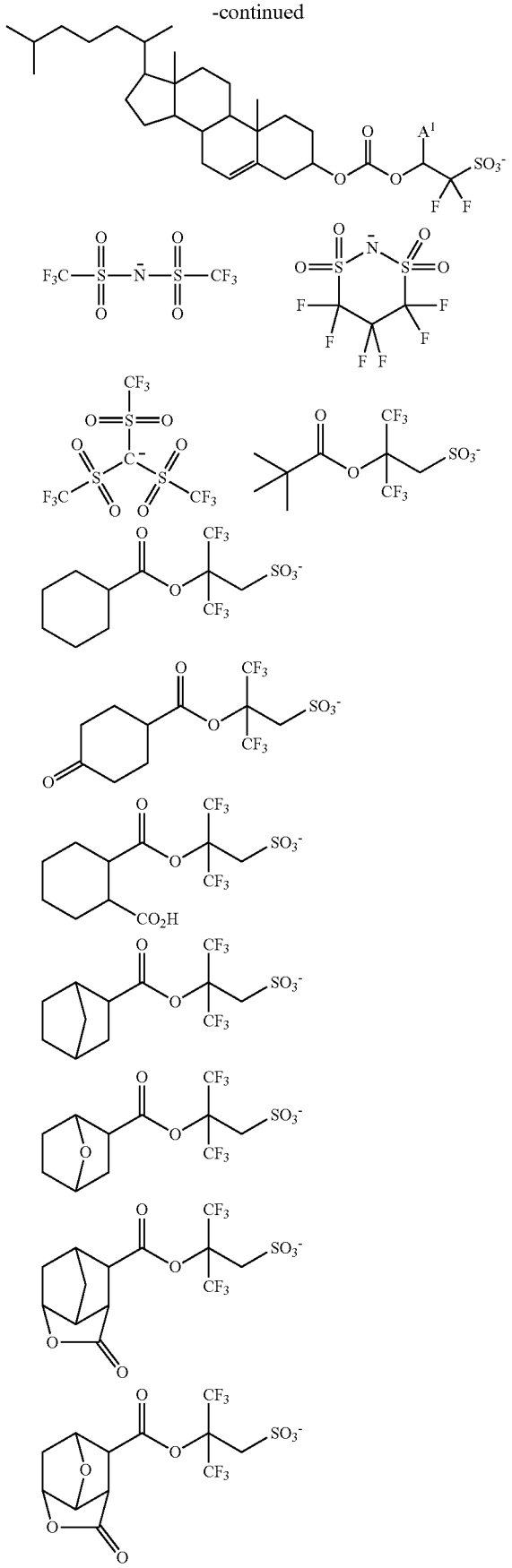
-continued
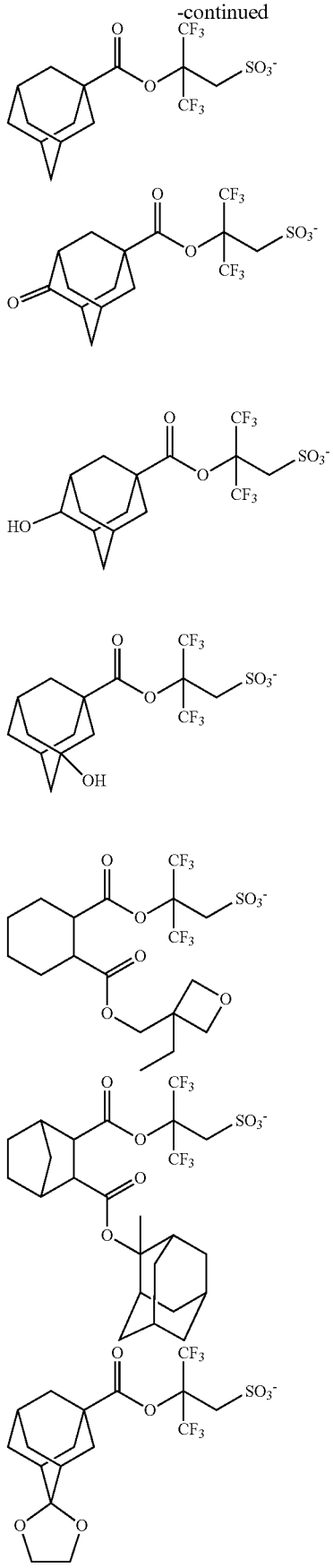

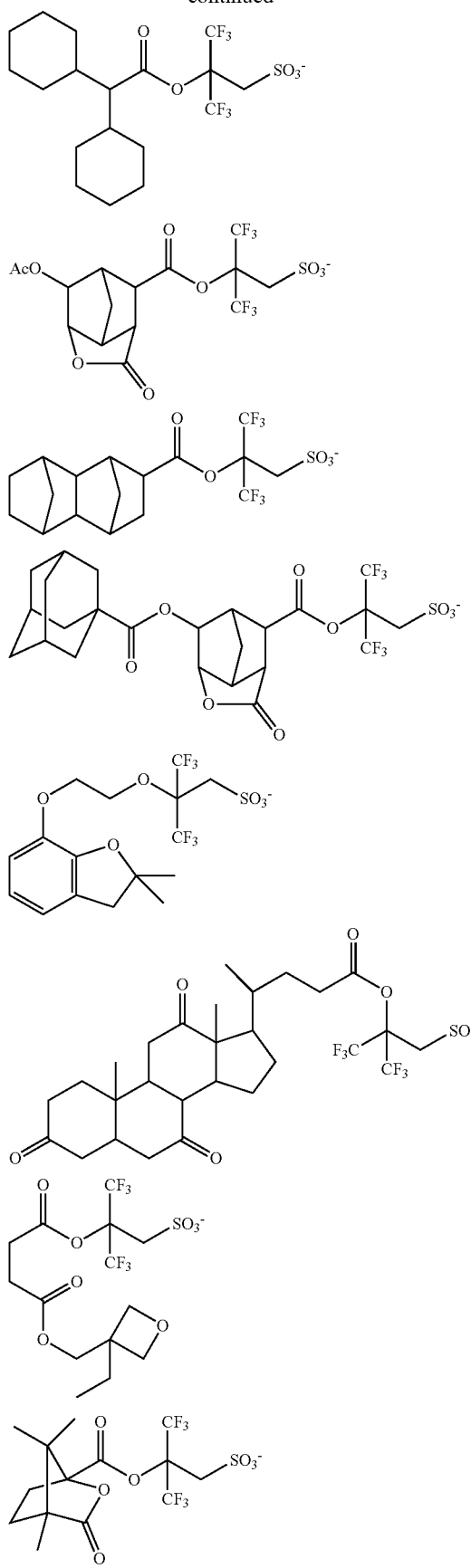
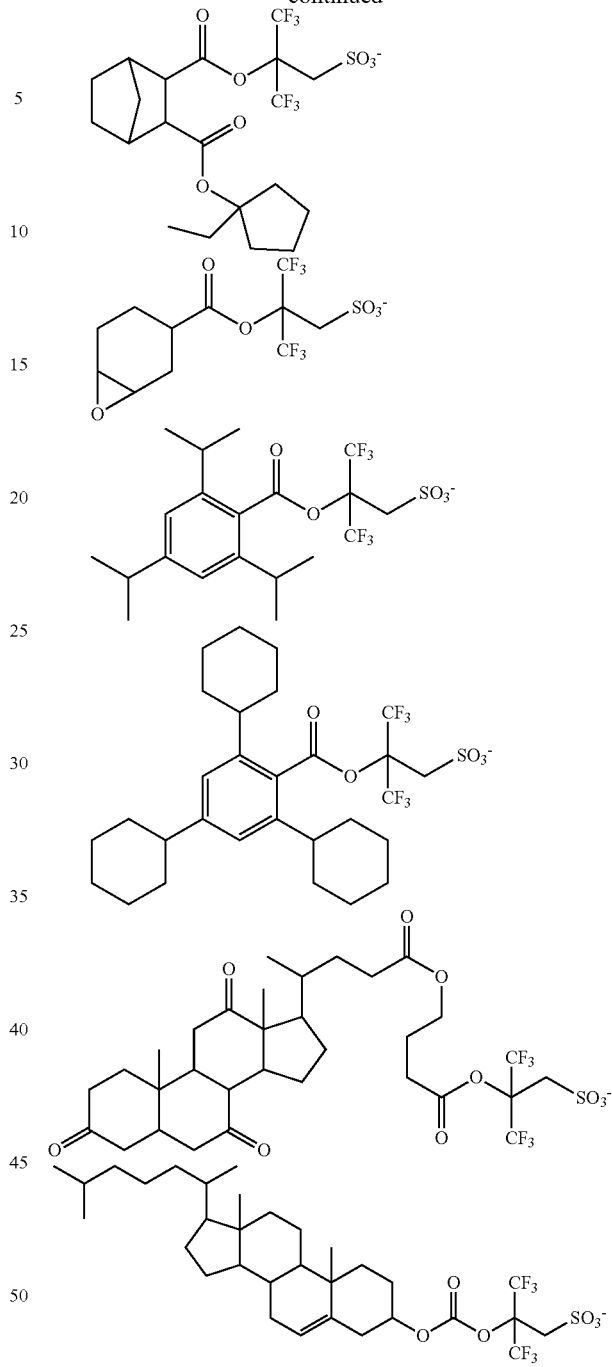

Illustrative example of the onium salt represented by the general formula (8) includes any combination of the anion and the cation, but the present invention is not restricted thereto.

Each of $R^{400}$ and $R^{500}$ in the general formula (9) independently represents a linear, a branched, or a cyclic monovalent hydrocarbon group having 1 to 30 carbon atoms optionally containing a heteroatom; $R^{600}$ represents a linear, a branched, or a cyclic divalent hydrocarbon group having 1 to 30 carbon atoms optionally containing a heteroatom, and any two or more of $R^{400}$, $R^{500}$, and $R^{600}$ may be bonded to form a ring together with a sulfur atom in the formula; $L^1$ represents a single bond or an ether bond, or a linear, a branched, or a cyclic divalent hydrocarbon group having 1 to 20 carbon atoms optionally containing a heteroatom (substituted by a heteroatom, or mediated by a heteroatom); each of $X_{a7}$, $X_{b7}$, $X_{a8}$, and $X_{b8}$ independently represents any of a hydrogen atom, a fluorine atom, or a trifluoromethyl group, and one or more of $X_{a7}$, $X_{b7}$, $X_{a8}$, and $X_{b8}$ represent a fluorine atom or a trifluoromethyl group.

Illustrative example of the compound represented by the general formula (9) includes the one represented by the following general formula (9') in particular, (9')

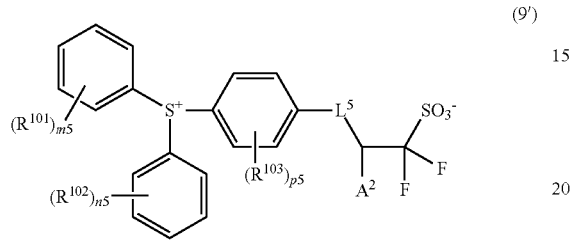

wherein, $A^2$ represents a hydrogen atom or a trifluoromethyl group; each of $R^{101}$, $R^{102}$, and $R^{103}$ independently represents a hydrogen atom, or a linear, a branched, or a cyclic monovalent hydrocarbon group having 1 to 20 carbon atoms, which may be substituted by a heteroatom; each of "m5" and "n5" represents an integer of 0 to 5; "p5" represents an integer of 0 to 4; $L^5$ represents a single bond or an ether bond, or a linear, a branched, or a cyclic divalent hydrocarbon group having 1 to 20 carbon atoms, which may be substituted by a heteroatom.

$L^5$ in the general formula (9') represents a single bond or an ether bond, or a linear, a branched, or a cyclic divalent hydrocarbon group having 1 to 20 carbon atoms, which may be substituted by a heteroatom, preferably an ether bond or $Q_X$-O-$L^{5'}$-O-$Q_Y$; $Q_X$ represents a bond with a benzene ring; $Q_Y$ represents a bond with —CH($A^2$)-$CF_2$—$SO_3$—; $L^{5'}$ represents a linear, a branched, or a cyclic divalent hydrocarbon group having 1 to 10 carbon atoms, which may be substituted by a heteroatom.

$A^2$ in the general formula (9') represents a hydrogen atom or a trifluoromethyl group, preferably a trifluoromethyl group.

A photo acid generator represented by the general formula (9) or (9') is described in detail in JP-A-2011-016746. Illustrative example thereof includes the sulfonium disclosed in the patent document, and the sulfonium disclosed in JP-A-2015-214634 paras. [0149] to [0150].

Illustrative example of the sulfonium represented by the general formula (9) includes the following sulfoniums, but the present invention is not restricted thereto. $A^2$ represents the same meaning as before,

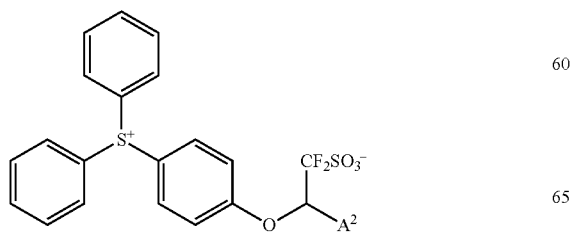

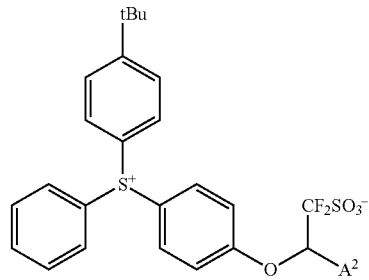

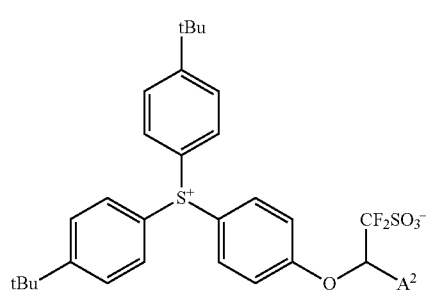

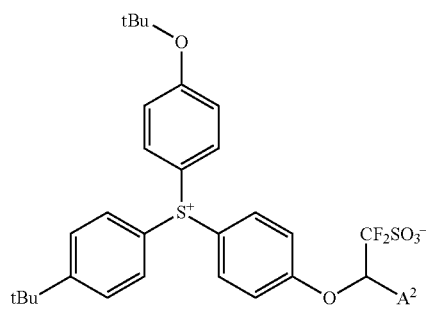

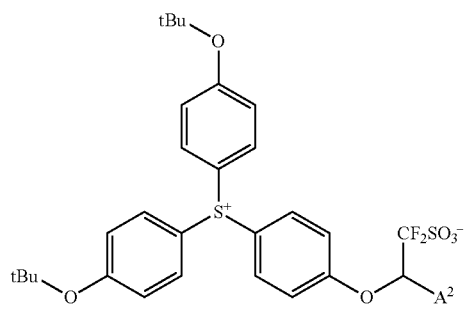

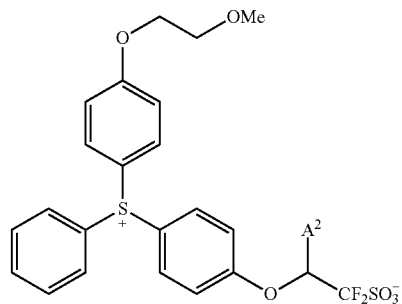

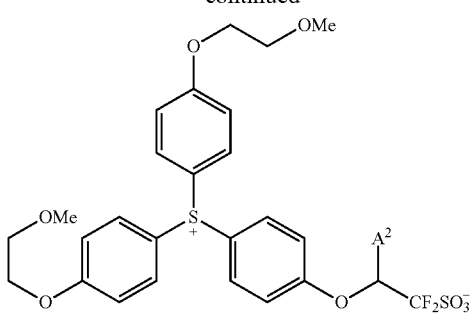
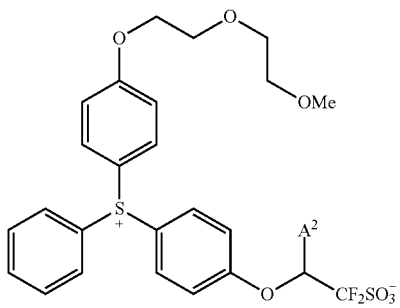
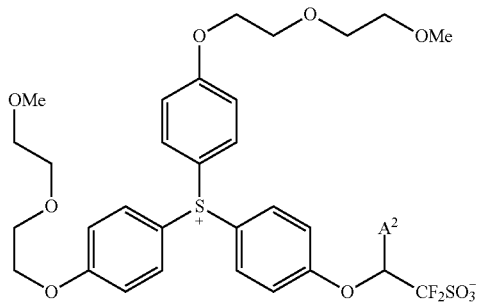
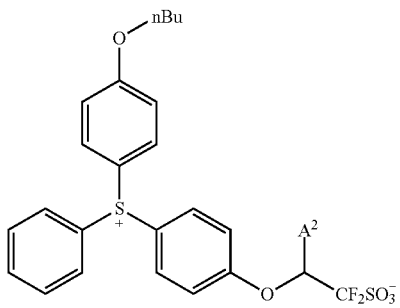
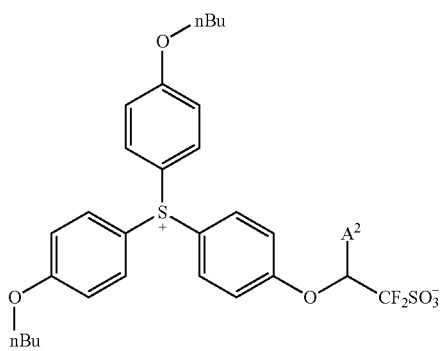
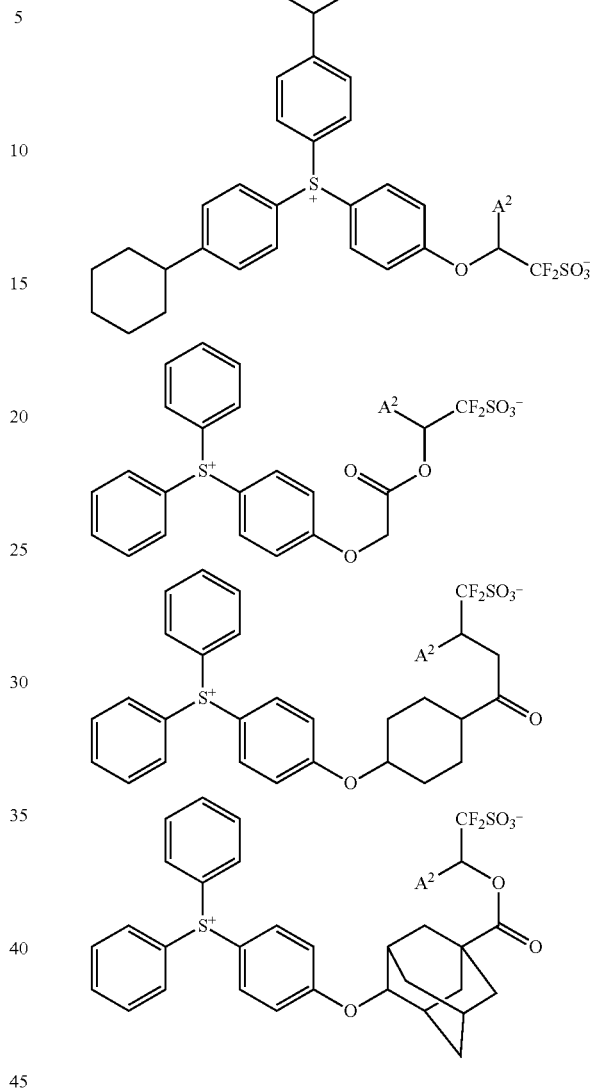

The photo acid generators having a structure represented by the general formula (8A') or (8D) are particularly preferable in that they have small acid diffusion and are excellent in solubility to resist solvent. The photo acid generators having a structure represented by the general formula (9') are particularly preferable in that they have extremely small acid diffusion.

The amount of the photo acid generator of the component (D) is preferably 0 to 40 parts by mass relative to 100 parts by mass of a base resin of the component (B), 0.5 to 30 parts by mass, and more preferably 0.5 to 20 parts by mass. So long as the amount is within the range, resolution degradation or mixture of foreign substances after resist development or upon peeling can be prevented.

(E) Quencher

The quencher of the component (E), as required, can be added to the resist composition of the present invention. Herein, the quencher refers to a compound capable of controlling the diffusion rate when an acid generated by a photo acid generator diffuses in a resist film.

Illustrative example of the quencher of the component (E) includes an amine compound, primary, secondary, and tertiary amine compounds disclosed in JP-A-2008-111103 paras. [0146] to [0164], particularly an amine compound having any of a hydroxy group, an ether bond, an ester bond, a lactone ring, a cyano group, or a sulfonic ester bond, as well as a compound in which a primary or secondary amine is protected as a carbamate group, such as a compound disclosed in JP-B-3790649. Such a protected amine compound is effective when a component that is unstable to a base in a resist composition is included.

In the present invention, as a quencher of the component (E), a compound (onium salt of sulfonate or carboxylic acid where α position is not fluorinated) represented by the following general formula (10) or (11) can also be used,

(10)

(11)

wherein, $R^{q1}$ represents a hydrogen atom, or a linear, a branched, or a cyclic monovalent hydrocarbon group having 1 to 40 carbon atoms optionally containing a heteroatom except for a hydrogen atom on a carbon atom at α-position of a sulfo group substituted by a fluorine atom or a fluoroalkyl group when $R^{q1}$ represents a monovalent hydrocarbon group; $R^{q2}$ represents a hydrogen atom, or a linear, a branched, or a cyclic monovalent hydrocarbon group having 1 to 40 carbon atoms optionally containing a heteroatom; and $Mq^+$ represents an onium cation.

$Mg^+$ in the general formula (10) and (11) is preferably an onium cation represented by any of the following general formula (c1), (c2), or (c3),

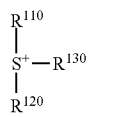

(c1)

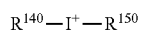

(c2)

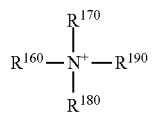

(c3)

wherein, each of $R^{110}$, $R^{120}$, $R^{130}$, $R^{140}$, $R^{150}$, $R^{160}$, $R^{170}$, $R^{180}$, and $R^{190}$ independently represents a linear, a branched, or a cyclic monovalent hydrocarbon group having 1 to 40 carbon atoms, which may be substituted by a heteroatom, and $R^{110}$ and $R^{120}$, or $R^{160}$ and $R^{170}$ may be bonded to form a ring together with a sulfur atom or a nitrogen atom bonded thereto.

Illustrative example of the $R^{q1}$ in the general formula (10) includes those as shown in the examples of the $R^1$ to $R^3$.

Illustrative example of the $R^{q2}$ in the general formula (11) includes those as shown in the examples of the $R^1$ to $R^3$. Illustrative additional example thereof includes a fluorine-containing alkyl group such as a trifluoromethyl group, a trifluoroethyl group, a 2,2,2-trifluoro-1-methyl-1-hydroxyethyl group, and a 2,2,2-trifluoro-1-(trifluoromethyl)-1-hydroxyethyl group; an aryl group such as a phenyl group, a tolyl group, a xylyl group, a 4-tert-butylphenyl group, and a naphthyl group; and a fluorine-containing aryl group such as a pentafluorophenyl group and a 4-trifluoromethylphenyl group.

As a quencher of the component (E) to be used, a sulfonate onium salt represented by the general formula (10), and a carboxylic acid onium salt represented by the general formula (11) are described in detail in JP-A-2008-158339 and JP-A-2010-155824. Illustrative example of the structure includes the structures disclosed in these patent documents.

Moreover, illustrative example of the preferable structure of the anion portions in the general formulae (10) and (11) includes the following anions, but the present invention is not restricted thereto,

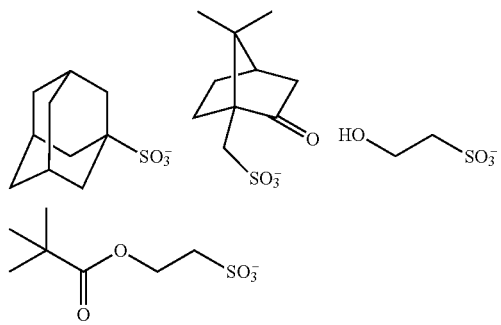

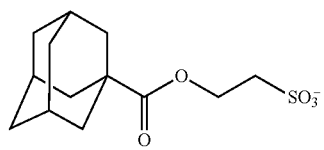

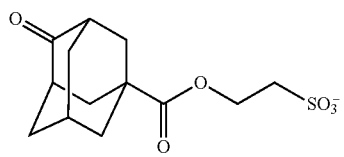

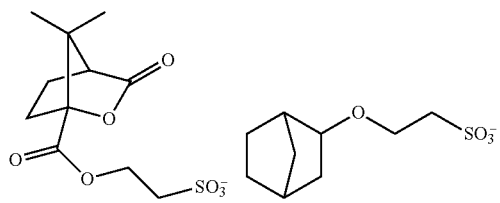

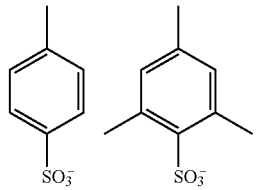

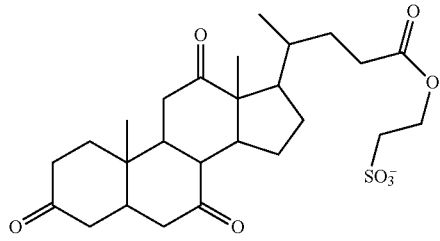

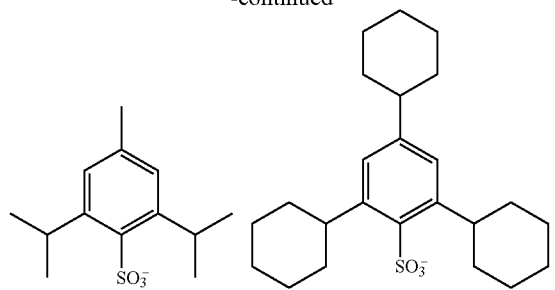
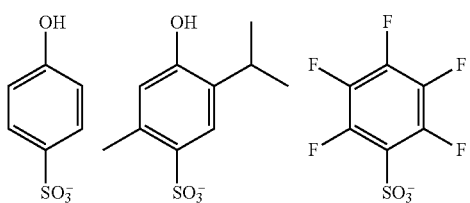
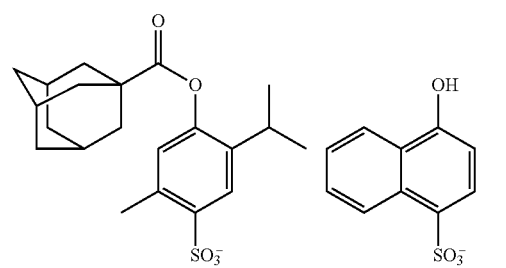
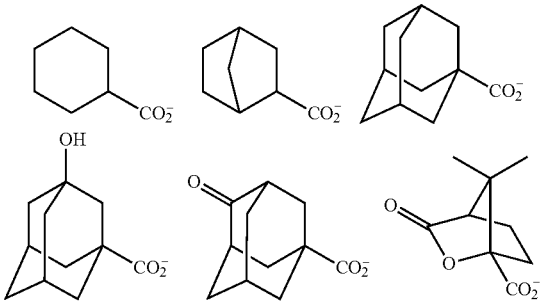
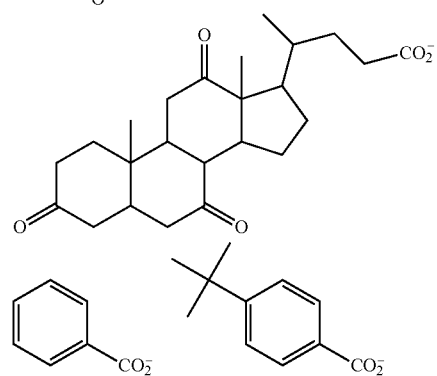
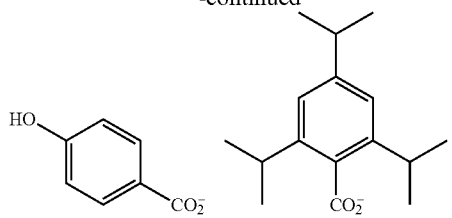
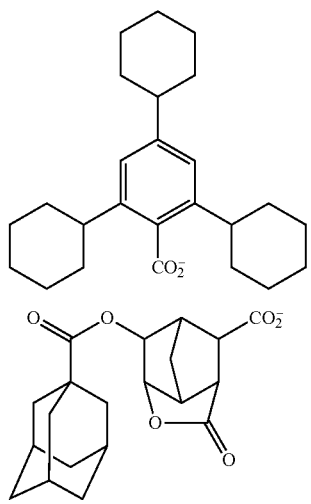
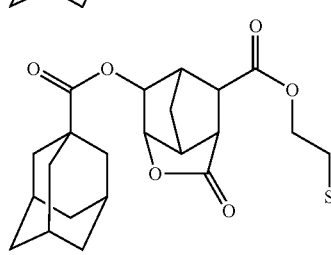
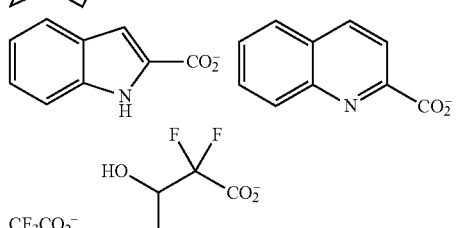
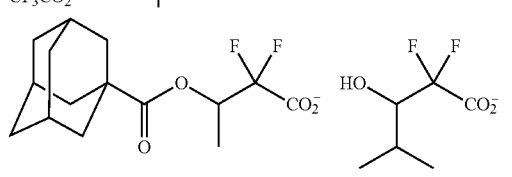
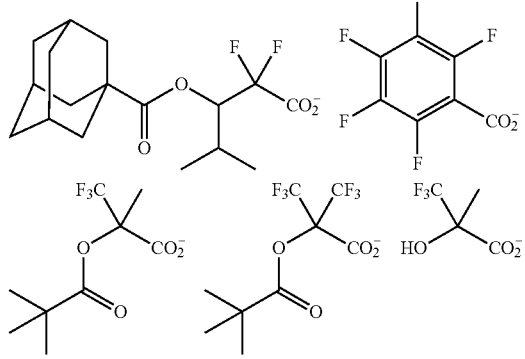

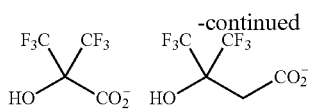

Furthermore, illustrative example of the preferable structure of the cation portions (Mq$^+$) in the general formulae (10) and (11) includes the one of the cation in the general formula (8) and the following structures, but the present invention is not restricted thereto,

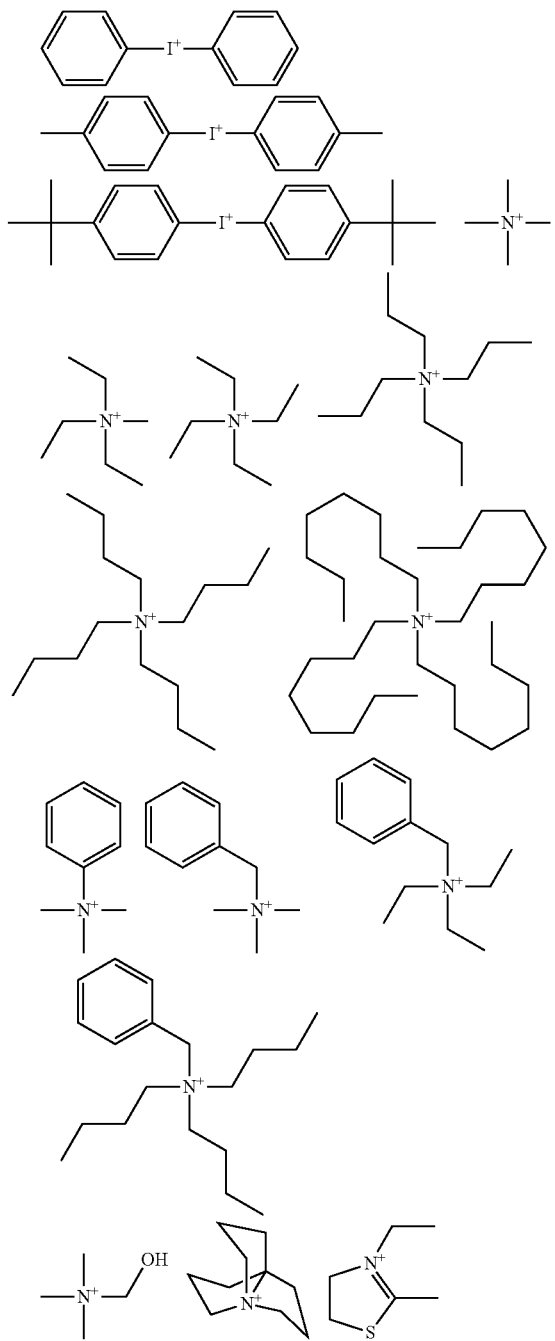

Illustrative example of the compound represented by the general formula (10) or (11) includes any combination of the anion and the cation. Such onium salts can readily be prepared by ion exchange reaction using known organic chemical methods. The ion exchange reaction can be found in JP-A-2007-145797.

The onium salt compound represented by the general formula (10) or (11) acts on the resist composition of the present invention as an acid diffusion controlling agent (quencher) of the component (5). This is attributed to the action of each counter anion of the onium salt compound as a conjugated base of weak acid. The weak acid refers to acidity that fails to deprotect the acid labile group of an acid labile group-containing unit used in a base resin. The onium salt represented by the general formula (10) or (11) functions as a quencher in combination with an onium salt-type photo acid generator having a conjugated base of strong acid as a counter anion such as sulfonate where α position is fluorinated. Consider the case where an onium salt for generating strong acid such as sulfonate where α position is fluorinated and an onium salt for generating weak acid such as non-fluorine-substituted sulfonate and carboxylic acid are mixed. A strong acid generated from a photo acid generator by high energy beam irradiation collides with an onium salt having an unreacted weak acid anion to release weak acid by salt exchange and generate an onium salt having a strong acid anion. Since this process allows for exchange of strong acid for weak acid having lower catalytic activity, an acid is seemingly inactivated to control the acid diffusion.

Particularly, in the onium salt compound represented by the general formula (10) or (11), an onium salt where Mq$^+$ represents a sulfonium cation represented by the general formula (c1), or where Mq$^+$ represents an iodonium cation represented by the general formula (c2) is photodegradable. Accordingly, the quenching ability of a portion having high light intensity is reduced and the concentration of a strong acid derived from a photo acid generator increases. As a result, patterns having favorable dimensional control that are provided with improved contrast of exposed area and further improved depth of focus (DOF) can be formed.

Herein, when a photo acid generator for generating a strong acid is an onium salt, as shown above, a strong acid generated by high energy beam irradiation can be exchanged for a weak acid. However, the weak acid generated by high energy beam irradiation is less likely to collide with an onium salt for generating an unreacted strong acid to conduct salt exchange. This is attributed to the ability of an onium cation to readily form an ion pair with an anion of stronger acid.

When the acid labile group is an acetal that is particularly sensitive to an acid, the acid for desorbing a protective group is not necessarily sulfonic acid, imide acid, or methide acid, which is fluorinated at α position. Even in sulfonic acid which is not fluorinated at α position, a deprotection reaction may proceed. Such a quencher may preferably be an onium salt of carboxylic acid as represented by the general formula (11).

A quencher of the component (E), in addition to the onium-type salt quencher, may be a betaine-type salt quencher such as a known compound, diphenyl iodonium-2-carbohydrate.

Also, a photodegradable onium salt having a nitrogen-containing substituent, as required, can be used in the resist composition of the present invention. Such a compound functions as a quencher in a non-exposed area, and functions as a photodegradable base that loses the ability of quenching by neutralization with an acid generated from itself in an exposed area. The use of the photodegradable base allows for sharper contrast between an exposed area and a non-exposed area. Illustrative example of the photodegradable base may include those in JP-A-2009-109595, JP-A-2012-046501, and JP-A-2013-209360.

The quencher of the component (E) can be used singularly or in combination with two or more quenchers, and the amount to be blended is 0 to 40 parts by mass relative to 100 parts by mass of a base resin of the component (B), preferably 0.1 to 40 parts by mass, and particularly 0.1 to 20 parts by mass. The amount of 40 parts by mass or less can prevent resolution degradation or mixture of foreign substances after resist development or upon peeling. So long as the amount is within the range, a quencher is blended to readily adjust the resist sensitivity. Also, this blending can control the acid diffusion rate in a resist film to improve the resolution, control changes in sensitivity after exposure, reduce the dependence on substrates and environment, and improve exposure margin and pattern profile. A quencher can be added to improve substrate adhesiveness.

(F) Surfactant

The resist composition of the present invention, other than the above components, may contain a surfactant conventionally used in improving the coating property as a component (F). The amount of any component to be added can be a normal amount, specifically with reference to a component (S) disclosed in JP-A-2010-215608 and JP-A-2011-016746.

The surfactant of the component (F) is preferably a surfactant that is insoluble or poorly soluble in water and soluble in an alkaline developer, or a surfactant (hydrophobic resin) that is insoluble or poorly soluble in water and an alkaline developer.

Illustrative example of the surfactant that is insoluble or poorly soluble in water and an alkaline developer includes FC-4430, Surflon S-381, Surfynol E1004, KH-20, and KH-30 out of the surfactants disclosed in the above patent documents, and an oxetane ring-opened polymer represented by the following structural formula (surf-1). These can be used singularly or in combination with two or more surfactants,

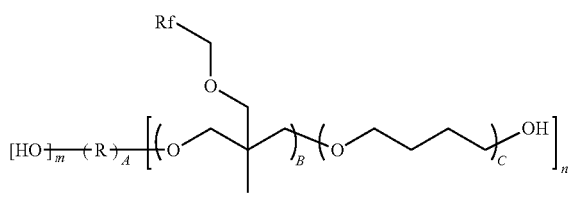

(surf-1)

wherein, "R", Rf, "A", "B", "C", "m", and "n" are essentially employed only in the structural formula (surf-1); "R" represents a divalent, a trivalent or a tetravalent aliphatic group having 2 to 5 carbon atoms, and specifically a divalent aliphatic group may be an ethylene group, a 1,4-butylene group, a 1,2-propylene group, a 2,2-dimethyl-1,3-propylene group, and a 1,5-pentylene group, and a trivalent or a tetravalent aliphatic group may be the following ones, preferably a 1,4-butylene group or a 2,2-dimethyl-1,3-propylene group,

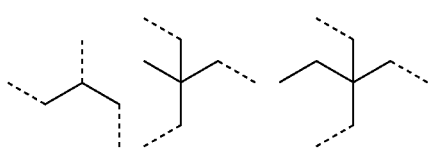

-continued

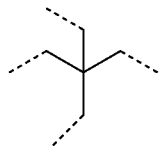

wherein, broken line represents a bond, and the partial structures are derived from glycerol, trimethylol ethane, trimethylol propane, and pentaerythritol.

Rf represents a trifluoromethyl group or a pentafluoroethyl group, preferably a trifluoromethyl group. "m" represents an integer of 0 to 3, and "n" represents an integer of 1 to 4, and the sum of "n" and "m" represents the valence of "R", and an integer of 2 to 4. "A" represents 1, "B" represents an integer of 2 to 25, preferably an integer of 4 to 20, and "C" represents an integer of 0 to 10, preferably 0 or 1. Each structural unit of the above structures is not specifically stipulated in arrangement, and may be bonded in block or random manner. The method for producing a partially fluorinated oxetane ring-opened polymer surfactant is described in detail in U.S. Pat. No. 5,650,483.

Advantageously, the surfactant that is insoluble or poorly soluble in water and soluble in an alkaline developer can reduce water immersion or leaching by being put on the resist surface after spin coating when a resist top coat is not used in ArF liquid immersion exposure. In addition, the elution of water-soluble components from a resist film is reduced to lower damage to an exposure apparatus. After exposure, the surfactant is also soluble during alkaline development after post-exposure baking to control generation of foreign substances leading to defects. The surfactant is insoluble or poorly soluble in water and soluble in an alkaline developer, known as "hydrophobic resin," particularly preferably water-repellent to improve water-sliding property. Illustrative example of the polymer surfactant includes those represented by the following formulae,

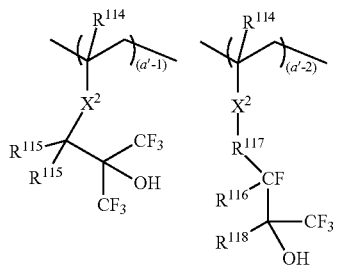

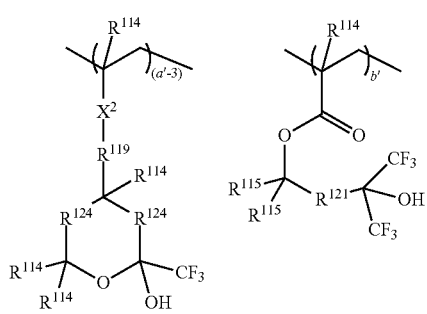

-continued

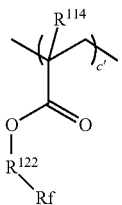

wherein, each of the $R^{114}$s independently represents a hydrogen atom, a fluorine atom, a methyl group, or a trifluoromethyl group; each of $R^{115}$s independently represents a hydrogen atom, or a linear, branched, or a cyclic alkyl group or a fluorinated alkyl group having 1 to 20 carbon atoms, and $R^{115}$s within the same monomer may be bonded to form a ring together with a carbon atom bonded thereto, and in this case, they represent a linear, a branched, or a cyclic alkylene group or a fluorinated alkylene group having 2 to 20 carbon atoms on total; $R^{116}$ represents a fluorine atom or a hydrogen atom, or may be bonded to $R^{117}$ to form a non-aromatic ring having 3 to 10 carbon atoms in total together with a carbon atom bonded thereto; $R^{117}$ represents a linear, a branched, or a cyclic alkylene group having 1 to 6 carbon atoms, and one or more hydrogen atoms may be substituted by a fluorine atom; $R^{118}$ represents a linear or a branched alkyl group having 1 to 10 carbon atoms where one or more hydrogen atoms is substituted by a fluorine atom, $R^{117}$ and $R^{118}$ may be bonded to form a non-aromatic ring together with a carbon atom bonded thereto, and in this case, the alkyl group represents a trivalent organic group having 3 to 12 carbon atoms totaled by those in $R^{117}$ and $R^{118}$, and carbon atoms bonded thereto; $R^{119}$ represents a single bond or an alkylene group having 1 to 4 carbon atoms; each of $R^{124}$s independently represents a single bond, —O—, or —$CR^{114}R^{114}$—; $R^{121}$ represents a linear or a branched alkylene group having 1 to 4 carbon atoms, and may be bonded to $R^{115}$ within the same monomer together with a carbon atom bonded thereto to form a non-aromatic ring having 3 to 6 carbon atoms; $R^{122}$ represents an alkylene group having 1 to 10 carbon atoms optionally containing a heteroatom, preferably a methylene group, a 1,2-ethylene group, a 1,3-propylene group, or a 1,4-butylene group; Rf represents a linear perfluoroalkyl group having 3 to 6 carbon atoms, a 3H-perfluoropropyl group, a 4H-perfluorobutyl group, a 5H-perfluoropentyl group, or a 6H-perfluorohexyl group; each of $X^2$s may be the same or different, and —C(=O)—O—, —O—, or —C(=O)—$R^{123}$—C(=O)—O—; $R^{123}$ represents a linear, a branched, or a cyclic alkylene group having 1 to 10 carbon atoms; and $0 \le (a'-1) < 1$, $0 \le (a'-2) < 1$, $0 \le (a'-3) < 1$, $0 < (a'-1) + (a'-2) + (a'-3) < 1$, $0 \le b' < 1$, $0 \le c' < 1$, and $0 < (a'-1) + (a'-2) + (a'-3) + b' + c' \le 1$.

A surfactant that is insoluble or poorly soluble in water or soluble in an alkaline developer can be referred to in JP-A-2007-297590, JP-A-2008-088343, JP-A-2008-111103, JP-A-2008-122932, JP-21-2010-134012, JP-A-2010-107695, JP-21-2009-276363, JP-21-2009-192784, JP-A-2009-191151, JP-A-2009-098638, JP-A-2010-250105, and JP-A-2011-042789.

The amount of the polymer surfactant to be added is preferably 0.001 to 20 parts by mass relative to 100 parts by mass of a base resin of the component (B), and more preferably 0.01 to 10 parts by mass. This data is described in detail in JP-A-2007-297590.

(G) Other Components

The resist composition of the present invention may include, in addition to the various additives, other components (G), including a compound for generating an acid by acid decomposition (acid growth compound), an organic acid derivative, a fluorine-substituted alcohol, a crosslinking agent, a compound having a weight average molecular weight of 3,000 or less that changes the solubility to a developer by acid action (dissolution inhibitor), and an acetylene alcohol. Specifically, the acid growth compound is described in detail in JP-A-2009-269953 and JP-A-2010-215608, and the amount thereof to be blended is preferably 0 to 5 parts by mass relative to 100 parts by mass of a base resin of the component (3), and more preferably 0 to 3 parts by mass. The amount of 3 parts by mass or less can encourage diffusion control, and is less likely to cause resolution degradation or pattern shape degradation. Other additives are described in detail in JP-A-2008-122932 paras. [0155] to [0182], JP-A-2009-269953, and JP-A-2010-215608.

The resist composition of the present invention thus obtained, as a photo acid generator, includes the sulfonium salt of the present invention to provide a chemically amplified resist composition having few defects in photolithography where a high energy beam such as KrF and ArF excimer laser lights, electron beam (EB), and extreme ultraviolet rays (EUV) is used as a light source, and excellent in lithography performance such as MEF, EL, LWR, and CDU by controlling acid diffusion.

[Patterning Process]

The present invention further provides a patterning process using the resist composition of the present invention. Using the resist composition of the present invention, the patterning process can be achieved by known lithography technology. More specifically, the patterning process of the present invention includes: applying the resist composition of the present invention to a substrate; exposing the composition with any of a high energy beam with a wavelength of 140 to 250 nm, an electron beam, or EUV via a photo mask after heating the composition before exposure; and developing the composition with a developer after heating the composition after exposure. The present invention is not restricted thereto, and as required, and additional steps may be added.

Figure 1B:
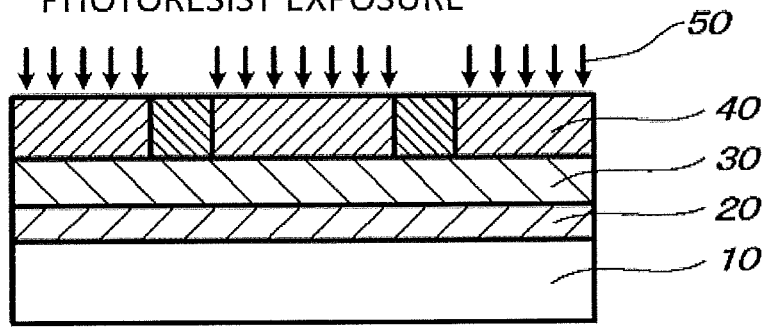
FIG. 1(B) is a cross-sectional view illustrating the exposure on the photoresist film.
Figure 1C:
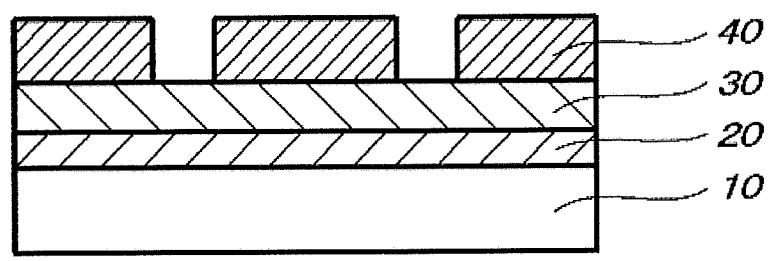
FIG. 1(C) is a cross-sectional view showing the development using an organic solvent.

One example of the patterning process of the present invention will be described below. In this patterning process, a substrate 10 having a layer to be processed 20 is prepared to form an intermediate interposed layer 30 on the layer to be processed 20, on which the resist composition of the present invention is applied, and a resist film 40 is formed by heating treatment before exposure (FIG. 1(A)). Formation of the intermediate interposed layer 30 may be optional. Then, the photoresist film 40 is irradiated with a light 50 via a photo mask for exposure (FIG. 1(B)). After heating treatment after exposure, the photoresist film 40 is developed using a developer of an organic solvent to dissolve a non-exposed area and obtain a negative pattern with an exposed area not dissolved (FIG. 1(C)). Likewise, the photoresist film 40 is developed using a developer of an alkaline aqueous solution to dissolve an exposed area and obtain a positive pattern with a non-exposed area not dissolved.

The substrate may be a substrate for producing an integrated circuit, such as Si, $SiO_2$, SiN, SiON, TiN, WSi, BPSG, SOG, and an organic antireflected film, or a substrate for producing a mask circuit, such as Cr, CrO, CrON, and MoSi.

A resist film can be formed by applying a resist composition on a substrate and prebaking on a hot plate at 60 to 180° C. for 10 to 600 seconds, preferably at 70 to 150° C. for 15 to 300 seconds, using a method such as spin coating so that the film thickness is preferably 10 to 2000 nm, and more preferably 20 to 500 nm.

A resist film can be irradiated for exposure by e.g., holding a mask for forming a target pattern over the above resist film, with high energy beam with a wavelength of 140 to 250 nm (preferably, KrF excimer laser and ArF excimer laser), EUV with a wavelength of 13.5 nm, or high energy beam such as electron beam (EB), preferably with an exposure dose of 1 to 200 mJ/cm$^2$, and more preferably an exposure dose of 10 to 100 mJ/cm$^2$. The exposure method may be a normal exposure method or, if necessary, immersion method (liquid immersion exposure) based on immersion between a mask and a resist film. In this case, a top coat that is insoluble in water can be used. In a liquid immersion exposure, a liquid with a refractive index of 1.0 or more is preferably mediated between an applied resist film and a projection lens.

The heating treatment after exposure (post-exposure baking; PEB) can be conducted on a hot plate at 60 to 150° C. for 1 to 5 minutes, preferably at 80 to 140° C. for 1 to 3 minutes.

In the development, e.g., 0.1 to 5% by mass of a developer of an alkaline aqueous solution such as tetramethylammoniumhydroxide (TMAH), preferably 2 to 3% by mass is preferable, or a conventional method such as dip method, puddle method, and spray method can be used with a developer for organic solvent, for 0.1 to 3 minutes, preferably for 0.5 to 2 minutes.

The method for forming a positive pattern using an alkaline aqueous solution as a developer is described in detail in JP-A-2011-231312 paras. [0138] to [0146], and the method for forming a negative pattern using an organic solvent as a developer is described in detail in JP-A-2015-214634 paras. [0173] to [0183].

The above top coat that is insoluble in water is used to prevent eluate from coming out of a resist film to improve the water-sliding property of the film surface, and roughly classified into two types. One is organic solvent peeling-type top coat where peeling is required before alkaline developing by an organic solvent in which a resist film is not dissolved, and the other is alkaline soluble-type top coat that is soluble in an alkaline developer to remove the top coat as well as a resist film soluble portion. The latter is preferably a composition in which a base of a polymer compound especially containing a 1,1,1,3,3,3-hexafluoro-2-propanol residue, which is insoluble in water and soluble in an alkaline developer, is dissolved in an alcohol solvent having 4 or more carbon atoms, an ether solvent having 8 to 12 carbon atoms, or a mixed solvent thereof. Also, the above surfactant that is insoluble in water and soluble in an alkaline developer can be used as an alcohol-based solvent having 4 or more carbon atoms, an ether-based solvent having 8 to 12 carbon atoms, or a material that dissolves in a mixture of these solvents.

The means of the patterning process is, after forming a photoresist film, may rinse an extract of an acid generator from a film surface using pure water rinse (post soak), rinse particles, or rinse (post soak) residue water on a film after exposure.

Furthermore, the life-extension technology of ArF lithography may be double patterning method. The double patterning method includes a trench method, in which an underlay is processed into a 1:3 trench pattern by first exposure and etching, and after shifting the position, a 1:3 trench pattern is formed by second exposure to form a 1:1 pattern; and a line method, in which a first underlay is processed into a 1:3 isolated pattern to be left by first exposure and etching, and after shifting the position, a second underlay formed under the first underlay is processed into a 1:3 isolated pattern to be left by second exposure to form a 1:1 pattern having a half pitch.

When hole patterns are formed by a negative tone development using an organic solvent-containing developer, two line patterns are exposed in X and Y directions using dipole illumination to provide light having highest contrast. Two line patterns are exposed in X and Y directions, using dipole illumination and s polarized illumination, to further increase the contrast. These patterning processes are described in detail in JP-A-2011-221513.

Hole patterns or trench patterns after development can be shrunk by thermal flow, resolution enhancement lithography assisted by chemical shrink (RELACS) technology, and directed self-assembly (DSA) technology. Specifically, after a shrink agent is applied to a hole pattern, the shrink agent generates crosslinking on the resist surface by diffusion of an acid catalyst from a resist layer during baking, and the shrink agent is attached to the side wall of the hole pattern. The bake temperature is preferably 70 to 180° C., and more preferably 80 to 170° C., and the bake time is 10 to 300 sec. This process removes an excess of the shrink agent and shrinks the hole pattern.

As for the developer of the patterning process of the present invention, illustrative example of the developer of alkaline aqueous solution includes the TMAH and an alkaline aqueous solution disclosed in JP-A-2015-180748 para. [0148] to [0149], preferably 2 to 3% by mass of tetramethyl ammonium hydroxide (TMAH). As the developer, illustrative example of the organic solvent includes 2-octanone, 2-nonanone, 2-heptanone, 3-heptanone, 4-heptanone, 2-hexanone, 3-hexanone, disobutyl ketone, methyl cyclohexanone, acetophenone, methylacetophenone, propyl acetate, butyl acetate, isobutyl acetate, amyl acetate, butenyl acetate, isoamyl acetate, propyl formate, butyl formate, isobutyl formate, amyl formate, isoamyl formate, methyl valerate, methyl pentenoate, methyl crotonate, ethyl crotonate, methyl propionate, ethyl propionate, ethyl 3-ethoxy propionate, methyl lactate, ethyl lactate, propyl lactate, butyl lactate, isobuthyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, 2-phenylethyl acetate, and a mixed solution of two or more thereof.

The patterning process of the present invention, using the resist composition of the present invention including the sulfonium salt of the present invention, can readily form excellently rectangle micropatterns having few defects.

EXAMPLE

The present invention will be described in detail with reference to the Synthesis Examples, Examples, and Comparative Examples, but the present invention is not restricted to the following Examples. In the following Examples, the molecular weight was confirmed by gel permeation chromatography of a tetrahydrofuran (THF) solution. The molecular weight refers to the average molecular weight in terms of polystyrene weight by GPC.

[Synthesis Example 1] Synthesis of Photo Acid Generator (PAG)

The photo acid generators used in Examples and Comparative Examples were synthesized according to the following prescriptions.

[Synthesis Example 1-1] Synthesis of PAG-1

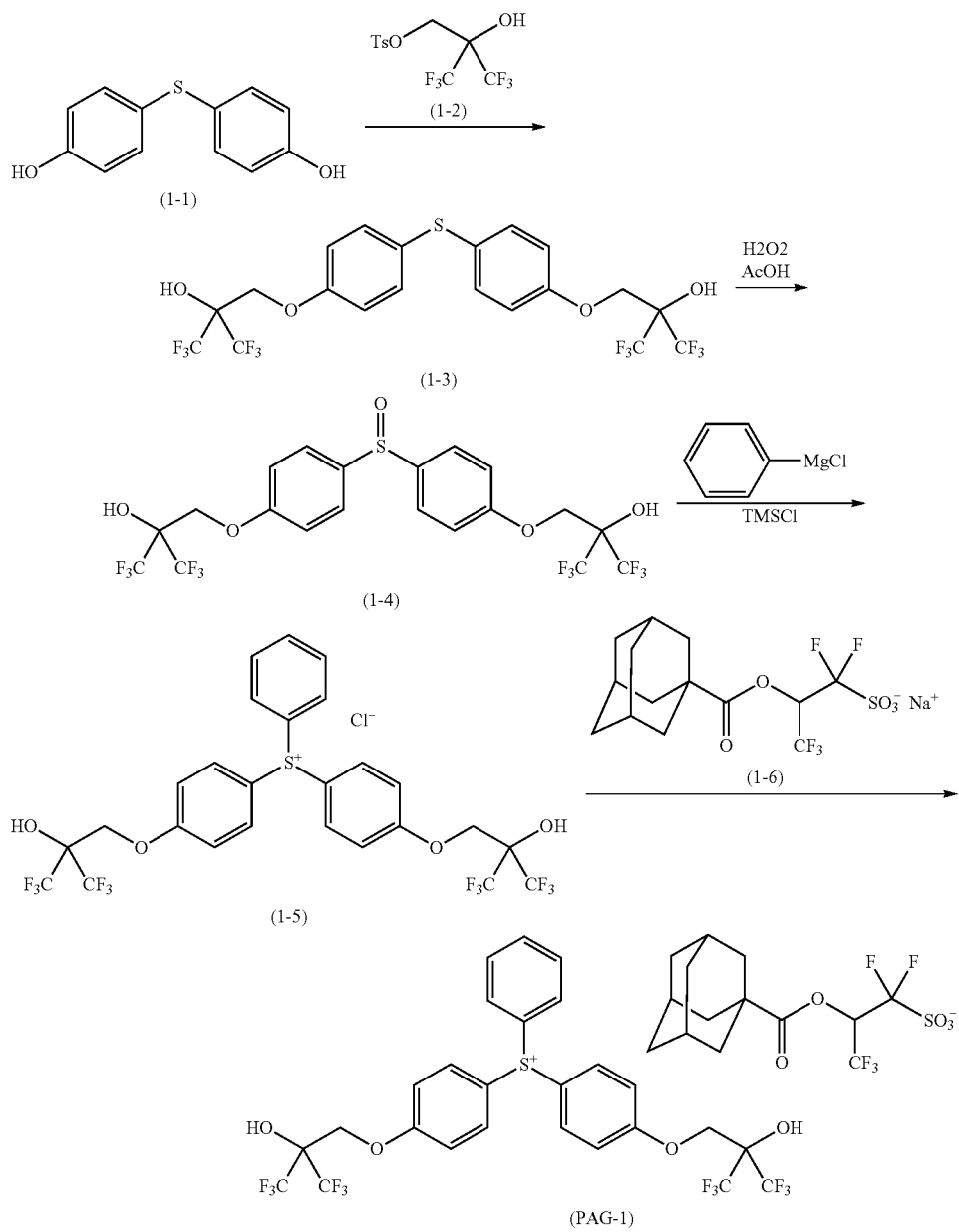

(Synthesis of Sulfide (1-3))

A 25% aqueous sodium hydroxide solution (120 g) was dropped into a mixed solution of bis(4-hydroxyphenyl) sulfide (1-1) (57.3 g), tetrahydrofuran (THF) (250 g), and pure water (60 g) at room temperature. After the product was stirred for 15 minutes, a mixed solution of tosylate (1-2) and THF (250 g) was maintained at 35° C. and dropped. After the product was stirred at room temperature for 18 hours, the reaction solution was cooled and a 5% aqueous hydrochloric acid solution (365 g) was added thereto to halt the reaction. Hexane (600 g) and toluene (600 g) were added and stirred to dispense an organic layer. The organic layer was cleaned with pure water (600 g) 3 times, a 0.25% aqueous sodium hydroxide solution (500 g) 6 times, 2.5% hydrochloric acid (500 g) once, and pure water (500 g) 3 times. Thereafter, the product was concentrated under reduced pressure to synthesize target sulfide (1-3) (109.2 g) as an oily substance.

(Synthesis of Sulfoxide (1-4))

A 35% hydrogen peroxide water ($H_2O_2$) was dropped into a mixed solution of the sulfide (1-3) above synthesized (109.2 g) and acetic acid (AcOH) (765.5 g) under ice-cooling. After dropping, ice bath was removed and the product was stirred at room temperature for 13.5 hours and at 40° C. for 5.5 hours. After cooling down to room temperature, a 10% sodium thiosulfate pentahydrate aqueous solution (44.4 g) was added thereto and stirred for one hour. The reaction solution was concentrated under reduced pressure and acetic acid was removed by evaporation, and ethyl acetate (1,000 g), toluene (500 g), and pure water (500 g) were added thereto and stirred, and a 25% aqueous sodium hydroxide solution was further added thereto and stirred until the pH of the aqueous layer reached 5 or so to dispense an organic layer. The obtained organic layer was cleaned with a 0.5% aqueous sodium hydroxide solution (500 g) twice, a 0.25% aqueous sodium hydroxide solution once, 2.5% hydrochloric acid (500 g) once, and pure water (500 g) 3 times, and concentrated under reduced pressure by removing a solvent by evaporation to deposit solids. After adding hexane (600 g) thereto, dispersing and stirring the solids, the product was filtered and cleaned with hexane. The solids obtained were dried under reduced pressure to synthesize a target sulfoxide (1-4) (104.7 g) (yield through 2 steps: 70%).

(Synthesis of Sulfonium Salt (1-5))

A 735.8 g/mol phenylmagnesiumchloride THF solution (340.5 g) was dropped into a mixed solution of a sulfoxide (1-4) (50 g) and THF (260 g) under ice-cooling. After stirring for 10 minutes under ice-cooling, trimethylsilyl chloride (TMSCl) (50.3 g) was dropped thereinto and further stirred under ice-cooling for 3 hours and at room temperature for 18 hours. After adding 3.2% hydrochloric acid (385.1 g) thereto to halt the reaction, the product was stirred at 40° C. for 10 hours. The mixed solution was extracted with methylene chloride (200 g) 3 times, and the obtained organic layer was cleaned with a 5% methanol aqueous solution (200 g) 3 times. After the obtained organic layer was concentrated under reduced pressure, the product was subjected to decantation using diisopropylether (300 g). Afterwards, a residue was concentrated under reduced pressure to synthesize a target sulfonium salt (1-5) (44.4 g) as an amorphous solid (yield: 76%).

(Synthesis of Photo Acid Generator (PAG-1))

A mixed solution of a sulfonium salt (1-5) (4.2 g), a 3,248 g/mol fluoro sulfonate sodium salt (1-6) (29.2 g), methylisobutylketone (40 g), and pure water 20 g was stirred for 10 minutes to dispense an organic layer. The obtained organic layer was cleaned with pure water (20 g) 3 times, and then concentrated under reduced pressure to remove a solvent by evaporation and subjected to decantation using a mixed solution of diisopropylether (15 g) and hexane (15 g). Afterwards, a residue was concentrated under reduced pressure to synthesize a target photo acid generator (PAG-1) (3.0 g) as an amorphous solid (yield: 45%).

<PAG-1>

$^1$H-NMR (500 MHz, in DMSO-$d_6$): δ=1.60-1.70 (6H, m), 1.83 (6H, d), 1.94-1.97 (3H, m), 4.55 (4H, s), 5.93 (1H, m), 7.40 (4H, m), 7.72-7.84 (9H, m), 8.54 (2H, s) ppm $^{19}$F-NMR (500 MHz, in DMSO-$d_6$): δ=−119.5 (1F, m), −113.5 (1F, m), −76.1 (12F, s), −72.5 (3F, m) ppm Time-of-flight mass spectrometry (TOFMS; MALDI) POSITIVE M$^+$655 (equivalent to $C_{26}H_{19}F_{12}O_4S^+$) NEGATIVE M$^-$391 (equivalent to $C_{14}H_{16}F_5O_5S^-$)

[Synthesis Example 1-2] Synthesis of PAG-2

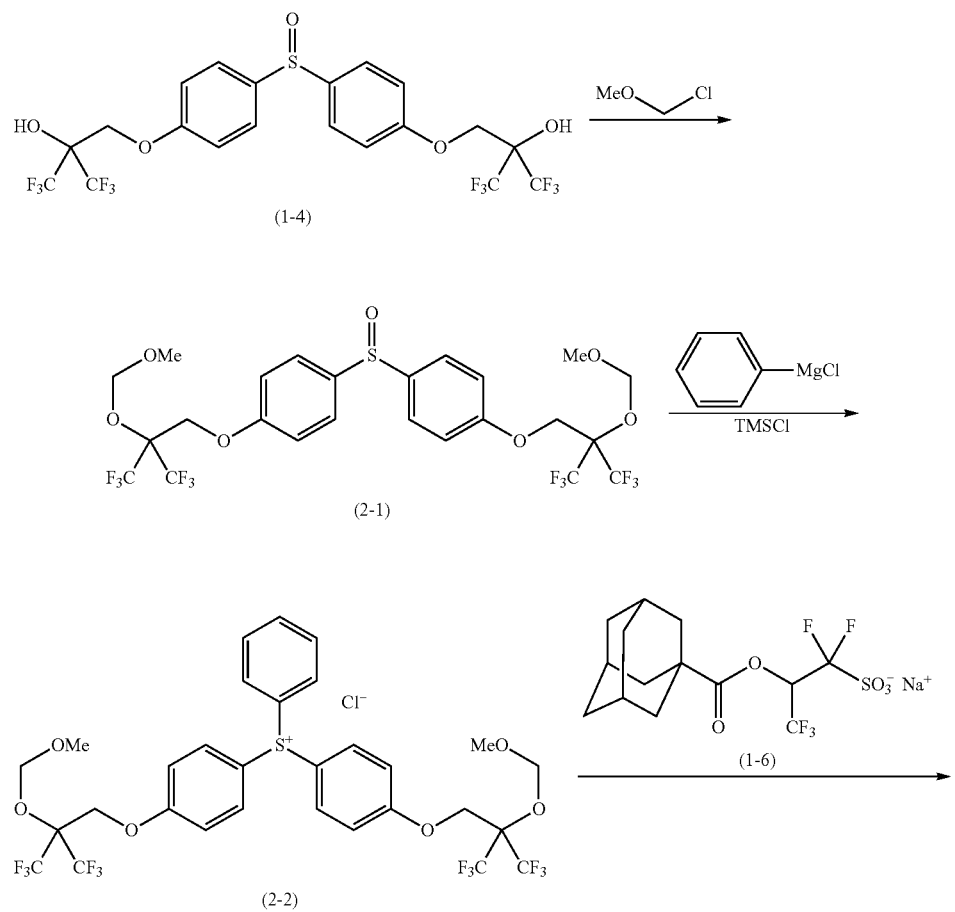

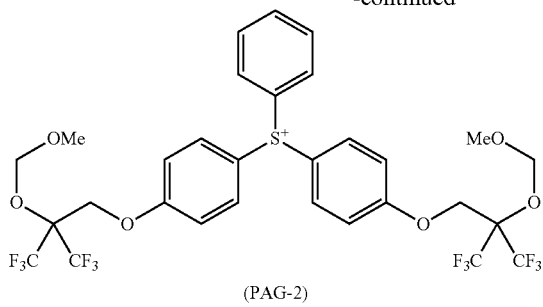

(PAG-2)

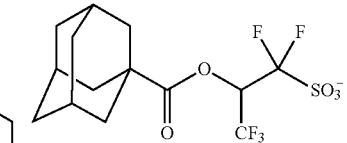

(Synthesis of Sulfoxide (2-1))

Chloromethylmethylether (4.2 g) was dropped into a mixed solution of a sulfoxide (1-4) (13.0 g), diisopropylethylamine (7.9 g), and acetonitrile (60 g) under ice-cooling. After the temperature was raised up to room temperature, the product was stirred for 19 hours. Furthermore, diisopropylethylamine (2.3 g) and chloromethylmethylether (1.1 g) were added thereto, stirred at room temperature for 40 hours, and pure water (100 g) was added thereto to halt the reaction. After toluene (100 g) was added thereto and stirred, an organic layer was dispensed, and cleaned with pure water (60 g), 1% ammonia solution (60 g), pure water (60 g) twice, 1% hydrochloric acid (60 g) 4 times, and pure water (60 g) 4 times. The obtained organic layer was concentrated under reduced pressure to synthesize a target sulfoxide (2-1) (14.4 g) as an oily substance.

(Synthesis of Sulfonium Salt (2-2))

A 683.5 g/mol phenylmagnesiumchloride THF solution (41.8 g) was dropped into a mixed solution of a sulfoxide (2-1) (14.4 g) and THF (57.4 g) under ice-cooling. After stirring for 10 minutes under ice-cooling, trimethylsilyl chloride (TMSCl) (6.7 g) was dropped thereinto, further stirred under ice-cooling for 3 hours and at room temperature for 17.5 hours. After ammonium chloride (3.27 g) and pure water (50 g) were added thereto to halt the reaction, methylisobutylketone (100 g) and pure water (50 g) were added thereto and stirred to disperse an organic layer. The obtained organic layer was cleaned with a saturated ammonium chloride aqueous solution (50 g) 4 times and pure water (50 g) 3 times. The obtained organic layer was concentrated under reduced pressure and subjected to decantation twice using hexane (150 g). Furthermore, hexane (150 g) was added to a residue and stirred, deposited solids were filtered and dried under reduced pressure to synthesize a target sulfonium salt (2-2) (11.0 g) as a solid (yield: 68%).

(Synthesis of Photo Acid Generator (PAG-2))

The ingredient was a sulfonium salt (2-2), instead of a sulfonium salt (1-5), and other conditions were the same as the synthesis of the photo acid generator (PAG-1) to synthesize a target photo acid generator (PAG-2) (3.5 g) (yield: 46%).

<PAG-2>

$^{1}$H-NMR (500 MHz, in DMSO-$d_6$): δ=1.60-1.70 (6H, m), 1.83 (6H, d), 1.94-1.97 (3H, m), 3.36 (6H, s), 4.90 (4H, s), 5.11 (4H, s), 5.93 (1H, m), 7.46 (4H, m), 7.73-7.86 (9H, m) ppm $^{19}$F-NMR (500 MHz, in DMSO-$d_6$): δ=−119.5 (1F, m), −113.5 (1F, m), −74.1 (12F, s), −72.5 (3F, m) ppm Time-of-flight mass spectrometry (TOFMS; MARDI)
POSITIVE M$^+$743 (equivalent to $C_{30}H_{27}F_{12}O_6S^+$)
NEGATIVE M$^-$391 (equivalent to $C_{14}H_{16}F_5O_5S^-$)

[Synthesis Example 1-3] Synthesis of PAG-3 for Comparison

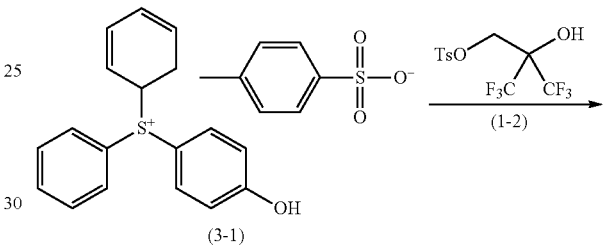

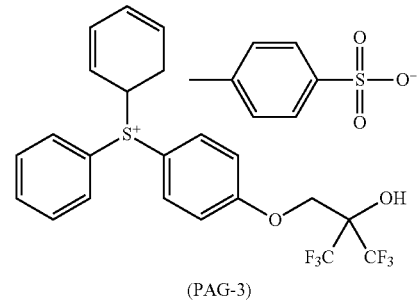

(PAG-3)

A 25% aqueous sodium hydroxide solution (4.8 g) was added to a mixed solution of a sulfonium salt (3-1) (13.5 g), THF (40 g), and pure water (8 g), and stirred at room temperature for 10 minutes. Furthermore, a mixed solution of tosylate (1-2) (7.1 g) and THF (20 g) was dropped thereinto and stirred at room temperature for 24 hours. After 5% hydrochloric acid (14.6 g) was added thereto to halt the reaction, methylisobutylketone (80 g) and pure water (80 g) were added thereto and stirred to disperse an organic layer. The obtained organic layer was cleaned with pure water (80 g) 6 times, concentrated under reduced pressure to remove a solvent by evaporation, and subjected to decantation 3 times using hexane. The obtained residue was concentrated under reduced pressure to synthesize a target photo acid generator (PAG-3) (10.7 g) as an amorphous solid. The PAG-3 is a sulfonium salt having a cation represented by the general formula (1'), not the sulfonium salt of the present invention.

<PAG-3>

IR (D-ATR): ν=3453, 3064, 1591, 1496, 1477, 1447, 1310, 1286, 1260, 1218, 1162, 1122, 1101, 1059, 1034, 1011, 835, 818, 750, 729, 682, 644, 656 cm$^{-1}$ $^1$H-NMR (500 MHz, in DMSO-d$_6$): δ-2.27 (3H, s), 4.56 (2H, s), 7.09 (2H, d), 7.41 (2H, m), 7.47 (2H, m), 7.74-7.86 (12H, m), 8.57 (1H, s) ppm $^{19}$F-NMR (500 MHz, in DMSO-d$_6$): δ=−76.1 (6F, s) ppm Time-of-flight mass spectrometry (TOFMS; MARDI)
POSITIVE M$^+$459 (equivalent to $C_{22}H_{17}F_6O_2S^+$)
NEGATIVE M$^-$171 (equivalent to $C_7H_7O_3S^-$)

[Synthesis Example 1-4] Synthesis of PAG-4

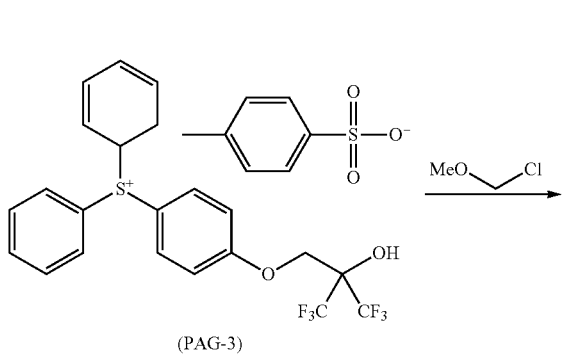

Chloromethylmethylether (3.3 g) was dropped into a mixed solution of a photo acid generator (PAG-3) (26.0 g), diisopropylethylamine (6.3 g) and acetonitrile (100 g) under ice-cooling. After stirring for one hour at room temperature, diisopropylethylamine (6.3 g) and chloromethylmethylether (3.3 g) were added thereto and stirred at room temperature for 14 hours. After pure water (200 g) was added thereto to halt the reaction, methylisobutylketone (150 g) was added thereto and stirred to dispense an organic layer. The obtained organic layer was cleaned with a 0.25% aqueous sodium hydroxide solution (70 g), pure water (70 g), 1% hydrochloric acid (70 g), and pure water (70 g) 3 times. The organic layer was concentrated under reduced pressure, and subjected to decantation twice using hexane, and the residue was concentrated under reduced pressure to synthesize a target photo acid generator (PAG-4) (10.2 g) as an oily substance (yield: 36%).

<PAG-4>

$^1$H-NMR (500 MHz, in DMSO-d$_6$): δ=2.27 (3H, s), 3.36 (3H, s), 4.91 (2H, s), 5.11 (2H, s), 7.09 (2H, m), 7.45-7.48 (4H, m), 7.74-7.81 (8H, m), 7.82-7.88 (4H, m) ppm $^{19}$F-NMR (500 MHz, in DMSO-d$_6$): δ=−74.2 (6F, m) ppm Time-of-flight mass spectrometry (TOFMS; MALDI)
POSITIVE M$^+$503 (equivalent to $C_{24}H_{21}F_6O_3S^+$)
NEGATIVE M$^-$171 (equivalent to $C_7H_7O_3S^-$)

[Synthesis Example 1-5] Synthesis of PAG-5

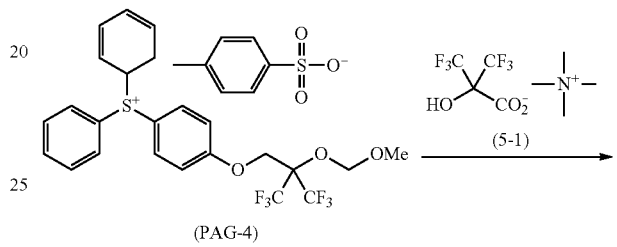

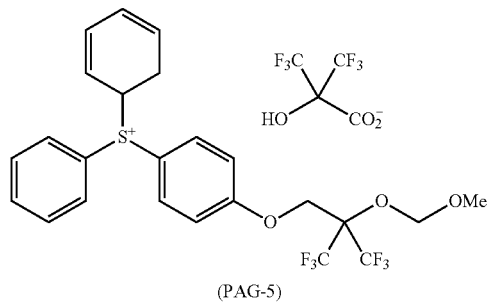

A mixed solution of a photo acid generator (PAG-4) (4.0 g), an aqueous solution (6.6 g) of a 611 g/mol ammonium salt (5-1), methylisobutylketone (40 g) and pure water (20 g) was stirred for 10 minutes to dispense an organic layer. The obtained organic layer was cleaned with pure water (20 g) 3 times and concentrated under reduced pressure to remove a solvent by evaporation, and subjected to decantation twice using hexane (50 g). The obtained residue was concentrated under reduced pressure to synthesize a target photo acid generator (PAG-5) (4.0 g) as an oily substance (yield: 93%).

<PAG-5>

IR (D-ATR): ν=3065, 1691, 1591, 1497, 1478, 1448, 1417, 1312, 1287, 1254, 1213, 1145, 1106, 1080, 998, 978, 836, 789, 749, 739, 684, 647 cm$^{-1}$ $^1$H-NMR (500 MHz, in DMSO-d$_6$): δ=3.36 (3H, s), 4.91 (2H, s), 5.11 (2H, s), 6.38 (1H, s), 7.47 (2H, m), 7.74-7.88 (12H, m) ppm $^{19}$F-NMR (500 MHz, in DMSO-d$_6$): δ=−74.6 (6F, s), −74.2 (6F, s) ppm Time-of-flight mass spectrometry (TOFMS; MALDI)
POSITIVE M$^+$503 (equivalent to $C_{24}H_{21}F_6O_3S^+$)
NEGATIVE M$^-$211 (equivalent to $C_4HF_6O_3^-$)

[Synthesis Example 1-6] Synthesis of PAG-6

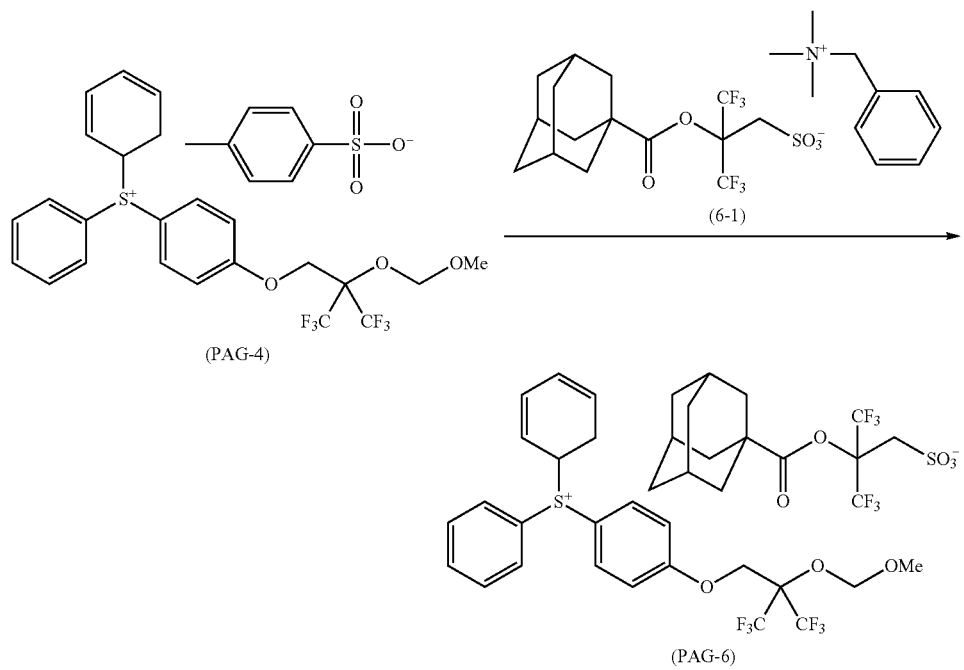

A mixed solution of a photo acid generator (PAG-4) (4.5 g), a sulfonate salt (6-1) (4.8 g), methylisobutylketone (40 g), and pure water (20 g) was stirred for 10 minutes to dispense an organic layer. The obtained organic layer was cleaned with pure water (20 g) 4 times and concentrated under reduced pressure to remove a solvent by evaporation. By silica gel column chromatography and purification, a target photo acid generator (PAG-6) (4.6 g) was synthesized as an amorphous solid (yield: 77%).
<PAG-6>
$^1$H-NMR (500 MHz, in DMSO-$d_6$): δ=1.64 (6H, m), 1.83 (6H, d), 1.95 (3H, s), 3.36 (3H, s), 3.54 (2H, s), 4.90 (2H, s), 5.11 (2H, s), 7.46 (2H, m), 7.74-7.80 (8H, m), 7.82-7.88 (4H, m) ppm
$^{19}$F-NMR (500 MHz, in DMSO-$d_6$): δ=−74.2 (6F, s), −72.3 (6F, s) ppm
Time-of-flight mass spectrometry (TOFMS; MALDI)
POSITIVE M$^+$503 (equivalent to $C_{24}H_{21}F_6O_3S^+$)
NEGATIVE M$^-$423 (equivalent to $C_{15}H_{17}F_6O_5S^-$)

[Synthesis Example 1-7] Synthesis of PAG-7

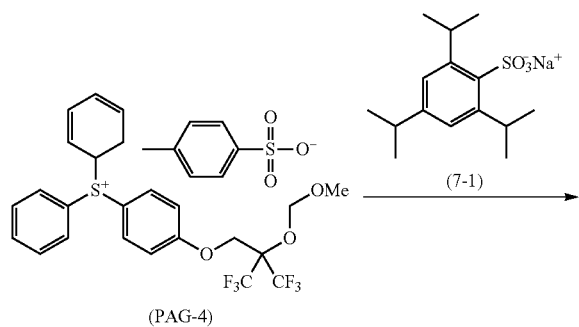

-continued (PAG-7)

A mixed solution of a photo acid generator (PAG-4) (3.8 g), a sulfonate salt (7-1) (1.9 g), methylisobutylketone (20 g), and pure water (15 g) was stirred for 30 minutes to dispense an organic layer. The obtained organic layer was cleaned with pure water (30 g) once, a 5% by mass sulfonate salt (7-1) aqueous solution (30 g) twice, and pure water (30 g) 4 times, and concentrated under reduced pressure to remove a solvent by evaporation. After methylene chloride (8 g) was added thereto to be dissolved, the product was dropped into diisopropylether (120 g) and stirred at 0° C. for 30 minutes to deposit solids. The solids deposited were filtered and dried under reduced pressure to synthesize a target photo acid generator (PAG-7) (3.4 g) as a solid (yield: 85%).
<PAG-7>
$^1$H-NMR (500 MHz, in DMSO-$d_6$): δ=1.08 (12H, d), 1.15 (6H, d), 2.78 (1H, m), 3.36 (3H, s), 4.57 (2H, m), 4.90 (2H, s), 5.11 (2H, s), 6.93 (2H, s), 7.45 (2H, m), 7.74-7.80 (8H, m), 7.82-7.88 (4H, m) ppm
$^{19}$F-NMR (500 MHz, in DMSO-$d_6$): δ=−74.2 (6F, s) ppm

[Synthesis Example 1-8] Synthesis of PAG-8

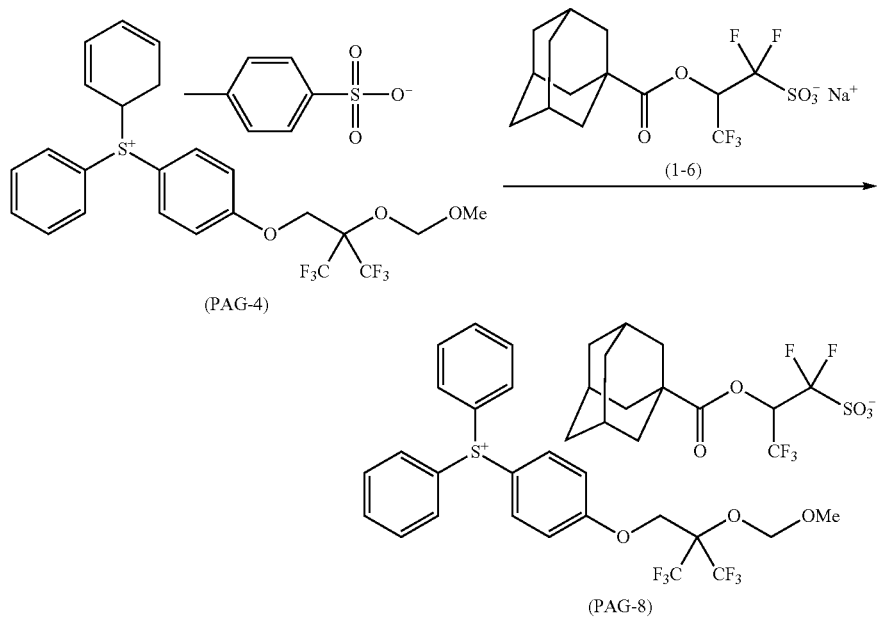

A mixed solution of a photo acid generator (PAG-4) (6.7 g), a 3,248 g/mol fluoro sulfonate sodium salt (1-6) (39.0 g), methylisobutylketone (50 g), and pure water (30 g) was stirred for 10 minutes to dispense an organic layer. The obtained organic layer was cleaned with pure water (20 g) 3 times and concentrated under reduced pressure to remove a solvent by evaporation, and subjected to decantation using diisopropylether (30 g). Afterwards, the residue was concentrated under reduced pressure to synthesize a target photo acid generator (PAG-8) (7.0 g) as an oily substance (yield: 75%).

<PAG-8>

$^1$H-NMR (500 MHz, in DMSO-d$_6$): δ=1.59-1.70 (6H, m), 1.83 (6H, d), 1.95 (3H, s), 3.36 (3H, s), 4.91 (2H, s), 5.11 (2H, s), 5.94 (1H, m), 7.47 (2H, m), 7.74-7.88 (12H, m) ppm $^{19}$F-NMR (500 MHz, in DMSO-d$_6$): δ=−119.5 (1F, m), −113.5 (1F, m), −74.2 (6F, s), −72.5 (3S, m) ppm

[Synthesis Example 1-9] Synthesis of PAG-9 for Comparison

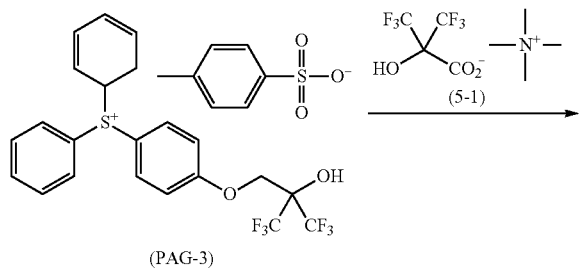

-continued

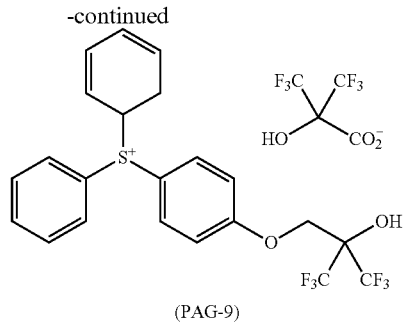

A mixed solution of a photo acid generator (PAG-3) (6.3 g), an aqueous solution (9.8 g) of a 611 g/mol ammonium salt (5-1), methylisobutylketone (60 g) and pure water (30 g) was stirred for 10 minutes to dispense an organic layer. The obtained organic layer was cleaned with pure water (30 g) 5 times, and concentrated under reduced pressure to remove a solvent by evaporation, and methylisobutylketone was added thereto to prepare a 50 wt % methylisobutylketone solution. After subjecting to decantation by adding hexane (80 g) thereto, the product was dissolved into methylisobutylketone (40 g), and an activated carbon (0.5 g) was added thereto and stirred for 18 hours. After the activated carbon was filtered for removal, a filtrate was concentrated under reduced pressure to synthesize a target photo acid generator (PAG-9) (6.8 g) as an oily substance (yield: 94%). The PAG-9 is a sulfonium salt having a cation represented by the general formula (1'), not the sulfonium salt of the present invention.

<PAG-9>

IR (D-ATR): ν=3066, 2962, 1688, 1592, 1467, 1477, 1448, 1415, 1311, 1257, 1212, 1162, 1149, 1103, 1060, 980, 834, 791, 748, 683, 646 cm$^{-1}$ $^1$H-NMR (500 MHz, in DMSO-d$_6$): δ=4.56 (2H, s), 6.38 (1H, s), 7.41 (2H, m), 7.74-7.79 (8H, m), 7.82-7.86 (4H, m), 8.60 (1H, br) ppm $^{19}$F-NMR (500 MHz, in DMSO-d$_6$): δ=−76.1 (6F, m), −74.5 (6F, m) ppm Time-of-flight mass spectrometry (TOFMS; MALDI)
POSITIVE M$^+$459 (equivalent to C$_{22}$H$_{17}$F$_6$O$_2$S$^+$)
NEGATIVE M$^-$211 (equivalent to C$_4$HF$_6$O$_3^-$)

[Synthesis Example 1-10] Synthesis of PAG-10 for Comparison

A mixed solution of a photo acid generator (PAG-3) (7.8 g), a sulfonate salt (6-1) (8.6 g), methylisobutylketone (50 g), and pure water (30 g) was stirred for 10 minutes to dispense an organic layer. The obtained organic layer was cleaned with pure water (40 g) 4 times, and concentrated under reduced pressure to remove a solvent by evaporation. By silica gel column chromatography and purification, a target photo acid generator (PAG-10) (9.5 g) was synthesized as an amorphous solid (yield: 87%). The PAG-10 is a sulfonium salt having a cation represented by the general formula (1'), not the sulfonium salt of the present invention.

<PAG-10>

$^1$H-NMR (500 MHz, in DMSO-d$_6$): δ=1.64 (6H, m), 1.83 (6H, d), 1.95 (3H, s), 3.54 (2H, s), 4.55 (2H, s), 7.41 (2H, m), 7.74-7.79 (8H, m), 7.81-7.86 (4H, m), 8.56 (1H, s) ppm $^{19}$F-NMR (500 MHz, in DMSO-d$_6$): δ=−76.1 (6F, s), −72.3 (6F, s) ppm

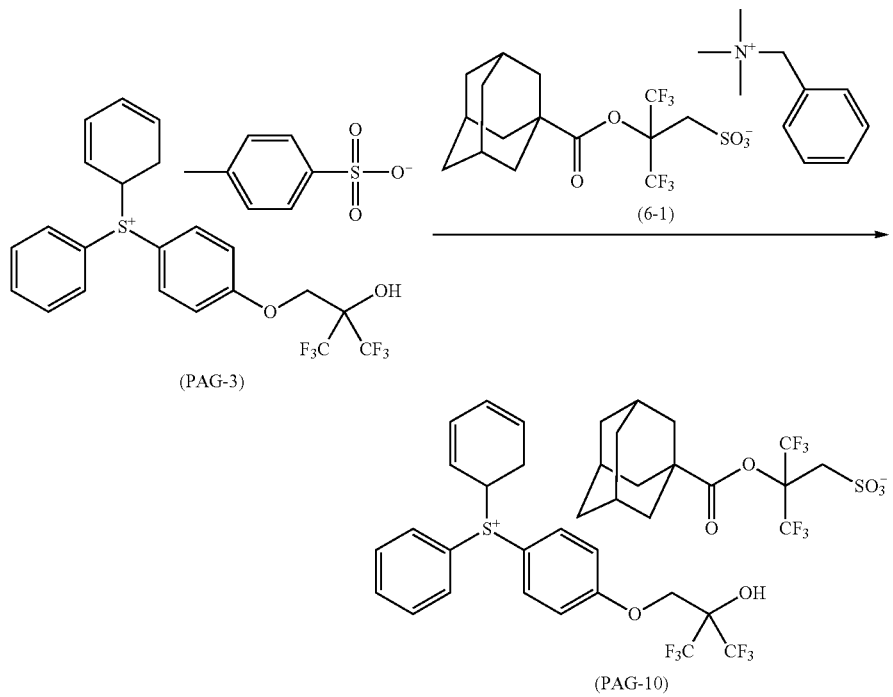

Time-of-flight mass spectrometry (TOFMS; MALDI)
POSITIVE M$^+$459 (equivalent to C$_{22}$H$_{17}$F$_6$O$_2$S$^+$)
NEGATIVE M$^-$423 (equivalent to C$_{15}$H$_{17}$F$_6$O$_5$S$^-$)

[Synthesis Example 1-11] Synthesis of PAG-11 for Comparison

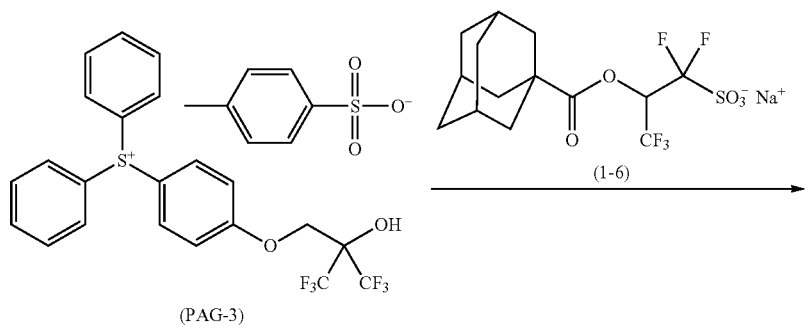

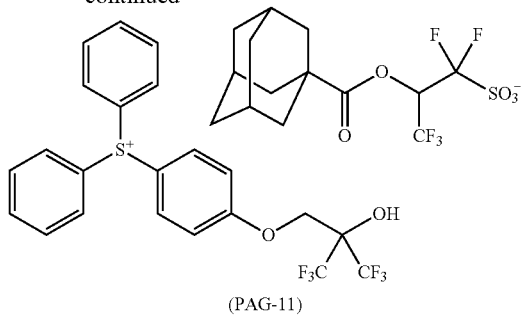

(PAG-11)

A mixed solution of a photo acid generator (PAG-3) (6.3 g), a 3,248 g/mol fluoro sulfonate sodium salt (1-6) (40.2 g), methylisobutylketone (50 g), and pure water (30 g) was stirred for 10 minutes to dispense an organic layer. The obtained organic layer was cleaned with pure water (20 g) 3 times, and concentrated under reduced pressure to remove a solvent by evaporation, and subjected to decantation using diisopropylether (30 g). The residue was concentrated under reduced pressure to synthesize a target photo acid generator (PAG-11) (7.3 g) as an oily substance (yield: 80%). The PAG-11 is a sulfonium salt having a cation represented by the general formula (1'), not the sulfonium salt of the present invention.
<PAG-11>
$^1$H-NMR (500 MHz, in DMSO-$d_6$): δ=1.59-1.70 (6H, m), 1.83 (6H, D), 1.95 (3H, s), 4.56 (2H, s), 5.94 (1H, m), 7.41 (2H, m), 7.74-7.79 (8H, m), 7.82-7.86 (4H, m), 8.60 (1H, br) ppm
$^{19}$F-NMR (500 MHz, in DMSO-$d_6$): δ=-119.5 (1F, m), -113.5 (1F, m), -76.1 (6F, s), -72.5 (3F, m) ppm

[Synthesis Examples 1-12 to 1-16] Synthesis of PAG-12 to PAG-16

Furthermore, with reference to the Synthesis Examples, the following PAG-12 to PAG-16 were synthesized. Each of the PAG-12 to PAG-16 is the sulfonium salt of the present invention, (PAG-12)

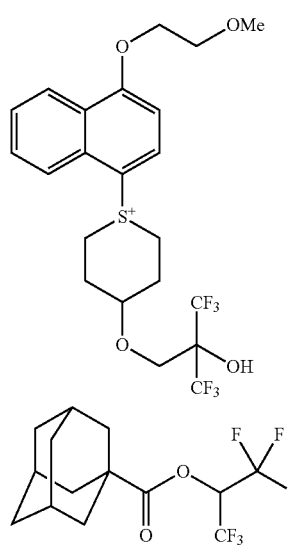

(PAG-13)

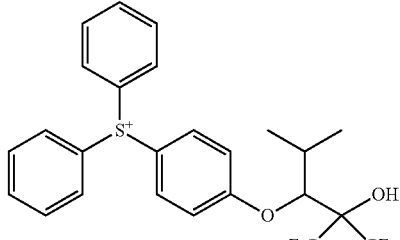

(PAG-14)

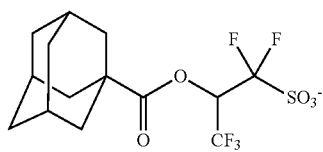

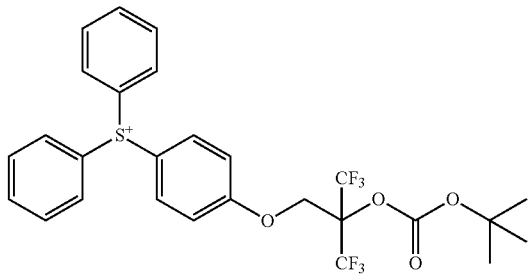

(PAG-15)

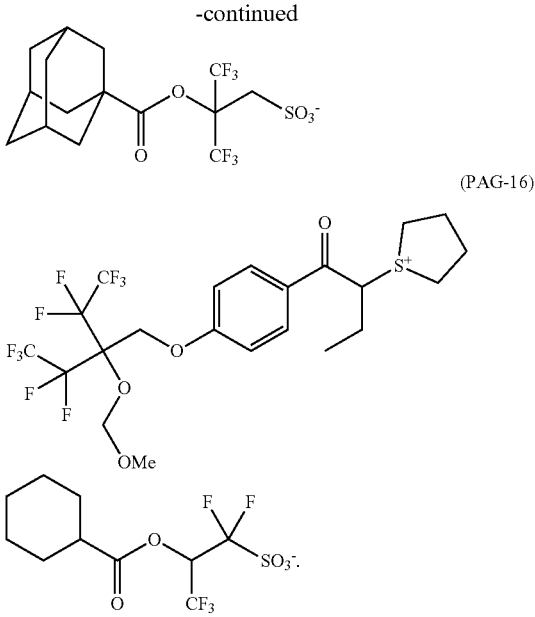

(PAG-16)

Synthesis Example 2

A polymer used in the resist composition of the present invention as a base resin was synthesized according to the following method.

[Synthesis Example 2-1] Synthesis of Polymer (P-1)

In nitrogen atmosphere, methacrylic acid=1-tert-butylcyclopentyl (22 g), methacrylic acid=2-oxotetrahydrofuran-3-yl (17 g), V-601 (Product from Wako Pure Chemical Industries, Ltd.) (0.48 g), 2-mercaptoethanol (0.41 g), and methylethylketone (50 g) were reacted to prepare a monomer-polymerization initiator solution. Methylethylketone (23 g) was placed into another flask in nitrogen atmosphere and stirred and heated up to 80° C., and then dropping the above monomer-polymerization initiator solution over 4 hours. After the dropping was completed, the temperature of a polymerization liquid was maintained at 80° C. and stirred for two hours and then cooled down to room temperature. The obtained polymerization liquid was dropped into strongly stirred methanol (640 g) and a deposited copolymer was filtered. The copolymer was cleaned with methanol (240 g) twice and vacuum-dried at 50° C. for 20 hours to obtain a white powdered copolymer (36 g) (yield: 90%). GPC analysis found that the weight average molecular weight (Mw) in terms of polystyrene was 8,200, and the degree of dispersion was 1.63.

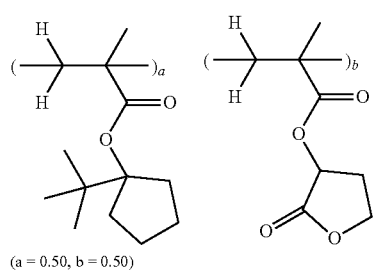

(P-1)

(a = 0.50, b = 0.50)

[Synthesis Examples 2-2 to 2-6] Synthesis of Polymers (P-2 to P-6)

The type of each monomer and the blending ratio were changed, and other conditions were the same as in Synthesis Example 2-1 to manufacture the following polymers.

The compositions of the manufactured polymers (P-2 to P-6) are shown in the following Table 1. In Table 1, the rate of introduction refers to molar ratio. The structure of each of the units in Table 1 is shown in the following Tables 2 and 3.

TABLE 1

| Resin | Unit 1 (Introduction ratio) | Unit 2 (Introduction ratio) | Unit 3 (Introduction ratio) | Unit 4 (Introduction ratio) | Mw | Degree of dispersion |
|---|---|---|---|---|---|---|
| P-1 | A-1 (0.50) | B-1 (0.50) | — | — | 8,200 | 1.63 |
| P-2 | A-1 (0.40) | B-2 (0.50) | B-4 (0.10) | — | 7,800 | 69 |
| P-3 | A-1 (0.40) | B-1 (0.35) | B-3 (0.15) | B-4 (0.10) | 8,400 | 1.75 |
| P-4 | A-2 (0.15) | A-3 (0.35) | B-1 (0.40) | B-4 (0.10) | 8,300 | 1.68 |
| P-5 | A-2 (0.15) | A-3 (0.35) | B-2 (0.40) | B-4 (0.10) | 9,000 | 1.80 |
| P-6 | A-1 (0.20) | A-4 (0.15) | B-1 (0.55) | B-4 (0.10) | 10,100 | 1.88 |

TABLE 2

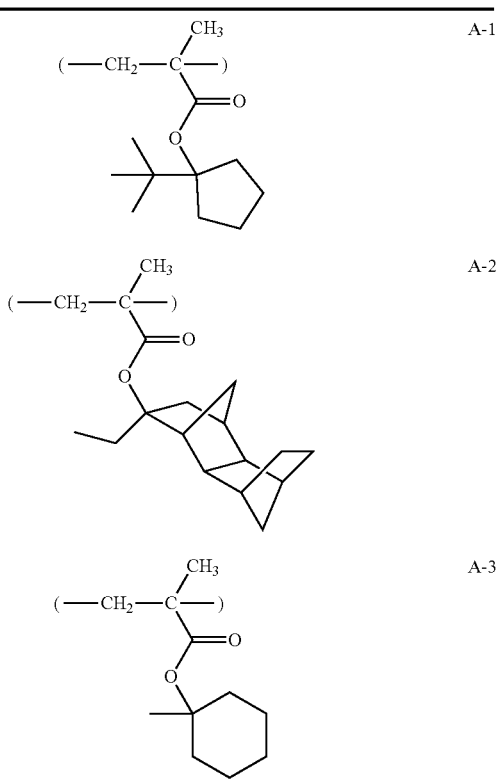

TABLE 2-continued

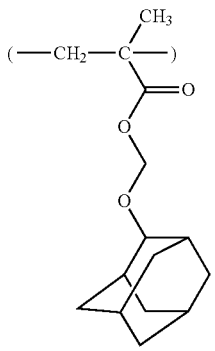

A-4

TABLE 3

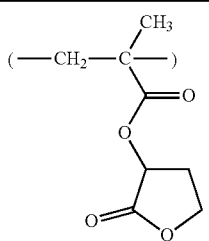

B-1

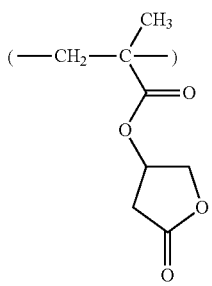

B-2

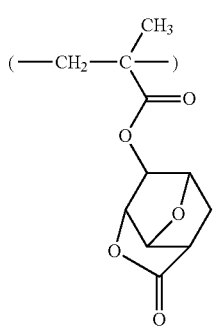

B-3

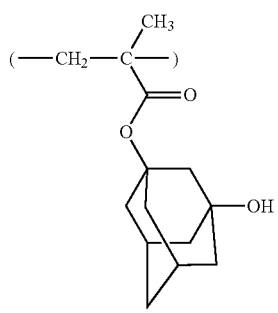

B-4

[Examples 1-1 to 1-12, Comparative Examples 1-1 to 1-8] Preparation of Resist Composition Solutions A photo acid generator shown in the above Synthesis Example, a polymer, and as required, sulfonium salts (PAG-A to F) other than the sulfonium salts shown in the above Synthesis Examples, a quencher (Q-1) and an alkaline soluble surfactant (SF-1) were dissolved into a solvent containing 0.01% by mass of a surfactant A (SF-A) (Product from OMNOVA Solutions Inc.) to prepare a resist composition, and the resist composition was filtrated with a filter of 0.2 μm Teflon (a registered trademark) to prepare resist composition solutions. The composition of each of the prepared resist composition solutions was shown in the following Tables 4 and 5.

In Tables 4 and 5, a quencher (Q-1) blended into resist compositions together with the sulfonium salts shown in the above Synthesis Examples and a polymer, a solvent, sulfonium salts other than the sulfonium salts shown in the above Synthesis Examples (PAG-A to PAG-F), and an alkaline soluble surfactant (SF-1) are as follows.

Quencher
Q-1: 1-(tert-butoxycarbonyl)-4-hydroxy piperidine

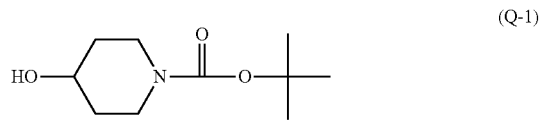

(Q-1)

Solvent
PGMEA: propylene glycol monomethyl ether acetate
GEL: γ-butyrolactone
Photo acid generator other than the onium salts of the above Synthesis Examples
PAG-A: Compound disclosed in JP-A-2007-145797

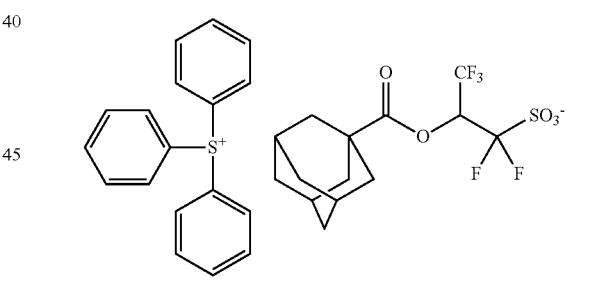

(PAG-A)

PAG-B: Compound disclosed in JP-A-2010-215608

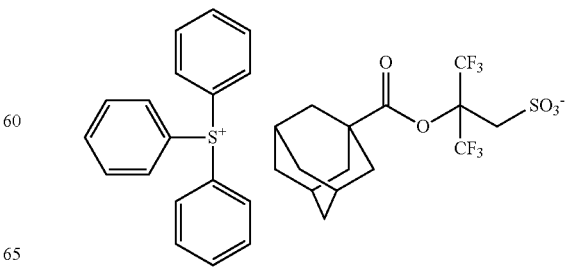

(PAG-B)

PAG-C: Compound disclosed in JP-A-2014-122204

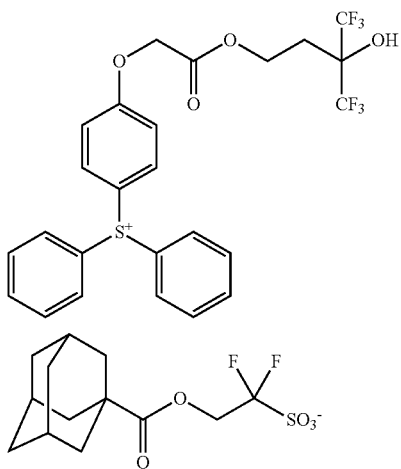
(PAG-C)

PAG-D: Compound having cation disclosed in JP-A-2014-122204

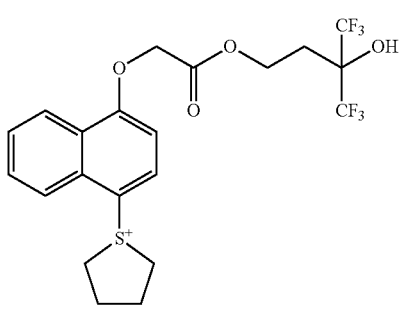
(PAG-D)

PAG-E: Compound disclosed in JP-B-4621806

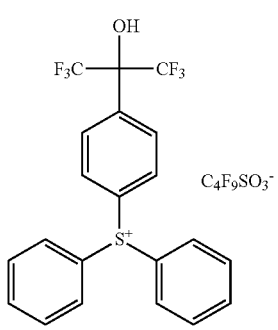
(PAG-E)

PAG-F: Compound disclosed in JP-B-4621806

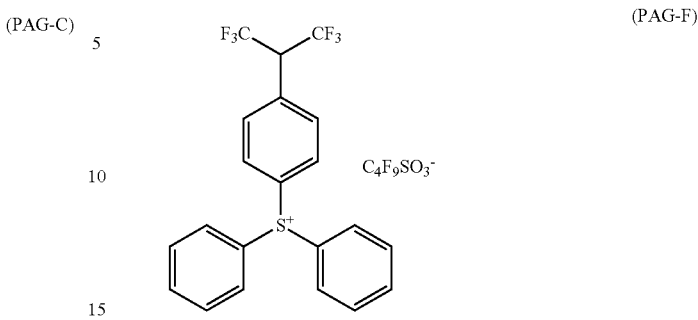
(PAG-F)

Alkaline soluble surfactant
SF-1: poly(methacrylic acid=2,2,3,3,4,4,4-heptafluoro-1-isobutyl-1-butyl.methacrylic acid=9-(2,2,2-trifluoro-1-trifluoroethyloxycarbonyl)-4-oxatricyclo[4.2.1.0$^{3,7}$]nonane-5-on-2-yl (compound represented by the following formula)
Molecular weight (Mw)=7,700
Degree of dispersion (Mw/Mn)=1.82

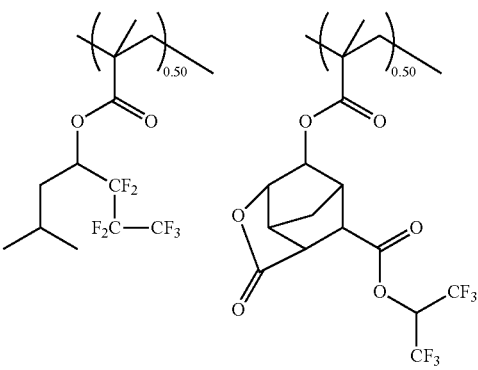
(SF-1)

Surfactant A (SF-A): 3-methyl-3-(2,2,2-trifluoroethoxymethyl)oxetane.THF.2,2-dimethyl-1,3-propanediol copolymer (Product from OMNOVA Solutions Inc.) (Compound represented by the following formula)

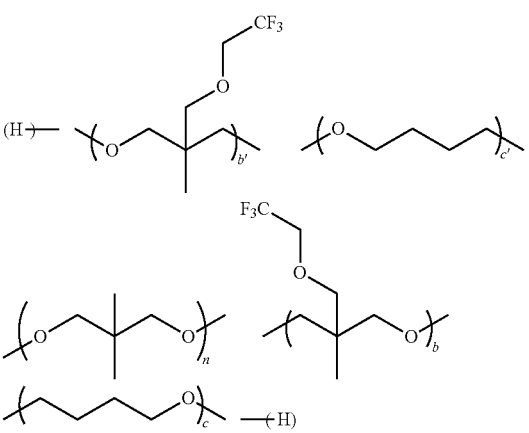

a:(b+b'):(c+c')=1:4~7:0.01~1 (molar ratio)
Weight average molecular weight: 1,500

TABLE 4

| | Resist | Resin (parts by mass) | Acid generator (parts by mass) | Quencher (parts by mass) | Surfactant (parts by mass) | Solvent 1 (parts by mass) | Solvent 2 (parts by mass) |
|---|---|---|---|---|---|---|---|
| Example 1-1 | R-1 | P-1 (80) | PAG-1 (8.0) PAG-B (3.0) | — | SF-1 (3.0) SF-A (0.01% by mass) | PGMEA (1.536) | GBL (384) |
| Example 1-2 | R-2 | P-1 (80) | PAG-2 (8.0) PAG-B (3.0) | — | SF-1 (3.0) SF-A (0.01% by mass) | PGMEA (1.536) | GBL (384) |
| Example 1-3 | R-3 | P-2 (80) | PAG-A (8.0) PAG-4 (2.5) | — | SF-1 (3.0) SF-A (0.01% by mass) | PGMEA (1.536) | GBL (384) |
| Example 1-4 | R-4 | P-3 (80) | PAG-A (8.0) PAG-5 (2.5) | — | SF-1 (3.0) SF-A (0.01% by mass) | PGMEA (1.536) | GBL (384) |
| Example 1-5 | R-5 | P-4 (80) | PAG-A (7.0) PAG-6 (3.0) | — | SF-1 (3.0) SF-A (0.01% by mass) | PGMEA (1.536) | GBL (384) |
| Example 1-6 | R-6 | P-6 (80) | PAG-A (7.0) PAG-7 (2.0) | — | SF-1 (3.0) SF-A (0.01% by mass) | PGMEA (1.536) | GBL (384) |
| Example 1-7 | R-7 | P-1 (80) | PAG-8 (8.0) PAG-B (3.0) | — | SF-1 (3.0) SF-A (0.01% by mass) | PGMEA (1.536) | GBL (384) |
| Example 1-8 | R-8 | P-3 (80) | PAG-12 (8.0) PAG-B (4.0) | Q-1 (1.0) | SF-1 (3.0) SF-A (0.01% by mass) | PGMEA (1.536) | GBL (384) |
| Example 1-9 | R-9 | P-1 (80) | PAG-13 (8.0) PAG-B (3.0) | — | SF-1 (3.0) SF-A (0.01% by mass) | PGMEA (1.536) | GBL (384) |
| Example 1-10 | R-10 | P-4 (80) | PAG-14 (8.0) PAG-B (3.0) | — | SF-1 (3.0) SF-A (0.01% by mass) | PGMEA (1.536) | GBL (384) |
| Example 1-11 | R-11 | P-3 (80) | PAG-A (6.0) PAG-15 (4.0) | Q-1 (1.0) | SF-1 (3.0) SF-A (0.01% by mass) | PGMEA (1.536) | GBL (384) |
| Example 1-12 | R-12 | P-5 (80) | PAG-16 (8.5) PAG-B (2.0) | Q-1 (1.0) | SF-1 (3.0) SF-A (0.01% by mass) | PGMEA (1.536) | GBL (384) |

TABLE 5

| | Resist | Resin (parts by mass) | Acid generator (parts by mass) | Quencher (parts by mass) | Surfactant (parts by mass) | Solvent 1 (parts by mass) | Solvent 2 (parts by mass) |
|---|---|---|---|---|---|---|---|
| Comparative Example 1-1 | R-13 | P-2 (80) | PAG-A (8.0) PAG-3 (2.5) | — | SF-1 (3.0) SF-A (0.01% by mass) | PGMEA (1.536) | GBL (384) |
| Comparative Example 1-2 | R-14 | P-3 (80) | PAG-A (8.0) PAG-9 (2.5) | — | SF-1 (3.0) SF-A (0.01% by mass) | PGMEA (1.536) | GBL (384) |
| Comparative Example 1-3 | R-15 | P-4 (80) | PAG-A (7.0) PAG-10 (3.0) | — | SF-1 (3.0) SF-A (0.01% by mass) | PGMEA (1.536) | GBL (384) |
| Comparative Example 1-4 | R-16 | P-1 (80) | PAG-11 (8.0) PAG-B (3.0) | — | SF-1 (3.0) SF-A (0.01% by mass) | PGMEA (1.536) | GBL (384) |

TABLE 5-continued

| Resist | | Resin (parts by mass) | Acid generator (parts by mass) | Quencher (parts by mass) | Surfactant (parts by mass) | Solvent 1 (parts by mass) | Solvent 2 (parts by mass) |
|---|---|---|---|---|---|---|---|
| Comparative Example 1-5 | R-17 | P-1 (80) | PAG-C (8.0) PAG-B (3.0) | — | SF-1 (3.0) SF-A (0.01% by mass) | PGMEA (1.536) | GBL (384) |
| Comparative Example 1-6 | R-18 | P-3 (80) | PAG-A (6.0) PAG-D (4.0) | Q-1 (1.0) | SF-1 (3.0) SF-A (0.01% by mass) | PGMEA (1.536) | GBL (384) |
| Comparative Example 1-7 | R-19 | P-1 (80) | PAG-E (8.0) PAG-B (3.0) | — | SF-1 (3.0) SF-A (0.01% by mass) | PGMEA (1.536) | GBL (384) |
| Comparative Example 1-8 | R-20 | P-1 (80) | PAG-F (8.0) PAG-B (3.0) | — | SF-1 (3.0) SF-A (0.01% by mass) | PGMEA (1.536) | GBL (384) |

[Examples 2-1 to 2-12, Comparative Examples 2-1 to 2-8] NTD; ArF Exposure Patterning Evaluation (1); Hole Pattern Evaluation The resist compositions of the present invention (R-1 to 12) prepared by the compositions according to the above Tables 4 and 5 and resist compositions (R-13 to 20) for Comparative Examples were spin-coated on a substrate for try layer process obtained by coating a spin-on carbon film ODL-101 (Product from Shin-Etsu Chemical Co., Ltd.) 200 nm in thickness, and a silicon-containing spin-on hard mask SHB-A940 (silicon content: 43% by mass) 35 nm in thickness thereon, and baked at 100° C. for 60 seconds using a hot plate to form a resist film 100 nm in thickness.

The product was subjected to first exposure using ArF immersion excimer laser stepper (Product from Nikon Corporation, NSR-6100, NA 1.30, σ 0.98/0.78, dipole opening 20 degrees, Azimuthally polarized illumination, 6% halftone phase shift mask, dipole illumination), and a mask with X-direction lines with a pitch of 80 nm and a line width of 40 nm (on-wafer size), and subsequently to second exposure using a mask with Y-direction lines with a pitch of 80 nm and a line width of 40 nm (on-wafer size) for post-exposure 60-second heat treatment (post-exposure baking: PEB). Thereafter, butyl acetate was discharged from a development nozzle by rotation for 3 seconds at 30 rpm and subjected to stationary puddle development for 27 seconds.
[Sensitivity Evaluation]

The obtained resist pattern was observed with electron microscope, and the exposure dose with a hole diameter of 40 nm in a 80 nm pitch was defined as the optimum exposure dose (Fop, mJ/cm$^2$).
[Mask Error Factor (MEF) Evaluation]

In the evaluation using the above mask, the mask pitch was fixed, and the mask line width was changed, and the films were irradiated with the optimum exposure dose in the above sensitivity evaluation to form patterns. From the changes in mask line width and pattern space width, MEF values were determined according to the following formula. The performance is favorable as the value approaches 1.

MEF=(pattern space width/mask line width)−b b: constant
[Critical Dimension Uniformity (CDU) Evaluation]

The obtained hole pattern was observed with TDSEM (CG-4000, Product from Hitachi High-Technologies Corporation) to measure hole diameters at 125 portions. The resulting standard deviation (σ) was multiplied by three (3σ) to be defined as a hole dimensional deviation. The smaller the 3σ value is, the smaller the dimensional deviation of a plurality of holes is.

[Exposure Latitude (EL) Evaluation]

In exposure latitude evaluation, the exposure latitude (unit: %) was determined from exposure dose which provided a hole pattern with a hole diameter of 40 nm±10% (36 nm to 44 nm), according to the following formula.

Exposure latitude (%)=(|E1−E2|/Eop)×100

E1: Optimum exposure dose providing hole pattern with a hole diameter of 36 nm and a pitch of 80 nm E2: Optimum exposure dose providing hole pattern with a hole diameter of 44 nm and a pitch of 80 nm Eop: Optimum exposure dose providing hole pattern with a hole diameter of 40 nm and a pitch of 80 nm Table 6 shows the results of the evaluations.

TABLE 6

| | Resist | PEB (° C.) | Eop (mJ/cm$^2$) | EL (%) | MEF | CDU (nm) |
|---|---|---|---|---|---|---|
| Example 2-1 | R-1 | 95 | 35 | 11.1 | 3.4 | 3.5 |
| Example 2-2 | R-2 | 95 | 34 | 11.0 | 2.9 | 3.4 |
| Example 2-3 | R-3 | 90 | 31 | 12.1 | 2.9 | 3.3 |
| Example 2-4 | R-4 | 90 | 29 | 12.0 | 2.8 | 3.4 |
| Example 2-5 | R-5 | 85 | 26 | 11.8 | 2.6 | 3.5 |
| Example 2-6 | R-6 | 85 | 31 | 12.4 | 2.9 | 3.2 |
| Example 2-7 | R-7 | 85 | 27 | 12.1 | 2.8 | 3.6 |
| Example 2-8 | R-8 | 90 | 30 | 11.9 | 3.3 | 3.4 |
| Example 2-9 | R-9 | 85 | 26 | 11.5 | 3.2 | 3.5 |
| Example 2-10 | R-10 | 95 | 25 | 11.6 | 3.3 | 3.2 |
| Example 2-11 | R-11 | 85 | 28 | 11.8 | 2.9 | 3.4 |
| Example 2-12 | R-12 | 85 | 27 | 11.3 | 2.8 | 3.6 |
| Comparative Example 2-1 | R-13 | 90 | 32 | 9.8 | 3.5 | 3.9 |
| Comparative Example 2-2 | R-14 | 90 | 29 | 9.7 | 3.4 | 3.9 |
| Comparative Example 2-3 | R-15 | 85 | 28 | 9.9 | 3.4 | 4.1 |
| Comparative Example 2-4 | R-16 | 85 | 29 | 10.0 | 3.6 | 4.1 |
| Comparative Example 2-5 | R-17 | 85 | 27 | 9.8 | 3.7 | 4.0 |

TABLE 6-continued

| | Resist | PEB (° C.) | Eop (mJ/cm²) | EL (%) | MEF | CDU (nm) |
|---|---|---|---|---|---|---|
| Comparative Example 2-6 | R-18 | 85 | 31 | 9.6 | 3.5 | 4.2 |
| Comparative Example 2-7 | R-19 | 85 | 25 | 9.0 | 4.0 | 4.6 |
| Comparative Example 2-8 | R-20 | 85 | 26 | 8.9 | 3.9 | 4.8 |

The results in Table 6 found the resist composition of the present invention demonstrates favorable lithography performance such as EL, MEF, and CDU in hole patterning by organic solvent development.

[Examples 3-1 to 3-12, Comparative Examples 3-1 to 3-8] NTD; ArF Exposure Patterning Evaluation (2); Line and Space Evaluation The resist compositions of the present invention (R-1 to 12) prepared by the compositions according to the above Tables 4 and 5 and resist compositions (R-13 to 20) for Comparative Examples were spin-coated on a substrate for try layer process obtained by coating a spin-on carbon film ODL-101 (Product from Shin-Etsu Chemical Co., Ltd.) 200 nm in thickness, and a silicon-containing spin-on hard mask SHB-A940 (silicon content: 43% by mass) 35 nm in thickness thereon, and baked at 100° C. for 60 seconds using a hot plate to form a resist film 100 nm in thickness.

The product was subjected to pattern exposure using ArF immersion excimer laser scanner (Product from Nikon Corporation, NSR-610C, NA1.30, σ0.98/0.78, 4/5 annular illumination), and a 6% halftone phase shift mask with a pitch of 100 nm a line width of 50 nm (on-wafer size) for post-exposure 60-second heat treatment (post-exposure baking: PEB). Thereafter, butyl acetate was discharged from a development nozzle by rotation for 3 seconds at 30 rpm and subjected to stationary puddle development for 27 seconds. Consequently, line and space pattern (LS pattern) where a non-exposed area protected from light by a mask is dissolved into a developer to cause image inversion was obtained with a space width of 50 nm and a pitch of 100 nm.

[Sensitivity Evaluation]

The obtained LS pattern was observed with electron microscope, and the optimum exposure dose (Eop, mJ/cm²) for obtaining a LS pattern with a space width of 50 nm and a pitch of 100 nm was determined.

[Exposure Latitude (EL) Evaluation]

In exposure latitude evaluation, the exposure latitude (unit: %) was determined from exposure dose which provided a LS pattern with a hole diameter of 50 nm±10% (45 nm to 55 nm), according to the following formula.

Exposure latitude (%)=(|E1−E2|/Eop)×100

E1: Optimum exposure dose providing LS pattern with a space width of 45 nm and a pitch of 100 nm
E2: Optimum exposure dose providing LS pattern with a space width of 55 nm and a pitch of 100 nm
Eop: Optimum exposure dose providing LS pattern with a space width of 50 nm and a pitch of 100 nm

[Mask Error Factor (MEF) Evaluation]

The mask pitch was fixed, and the mask line width was changed, and the films were irradiated with the optimum exposure dose in the above sensitivity evaluation to form patterns. From the changes in mask line width and pattern space width, MEF values were determined according to the following formula. The performance is favorable as the value approaches 1.

MEF=(pattern space width/mask line width)−b b: constant

[Line Width Roughness (LWR) Evaluation]

The LS pattern obtained by irradiating films with the optimum exposure dose was subjected to dimensional measurement at 10 portions in the longitudinal direction of the space width using TDSEM (S-9380, Product from Hitachi High-Technologies Corporation). The resulting standard deviation (σ) was multiplied by three (3σ) to be defined as a LWR. As the 3σ value is small, a pattern with small roughness and uniform space width can be obtained.

[Defect Density Evaluation]

The number of defects in a pattern formed after development was examined by a defect inspection system KLA2800 (Product from KLA-Tencor) to determine the defect density according to the following formula.

Defect density (number/cm²)=total number of detected defects/inspected area

Formed pattern: 50 nm 1:1 line and space's repeated pattern
Defect inspection conditions: light source UV, inspected pixel size 0.28 μm, cell to cell mode In this evaluation, "favorable" is under 0.05/cm², and "unfavorable" is 0.05/cm² or more.

Table 7 shows the results of the evaluations.

TABLE 7

| | Resist | PEB (° C.) | Eop (mJ/cm²) | EL (%) | MEF | LWR (nm) | Defect Density (number/cm²) |
|---|---|---|---|---|---|---|---|
| Example 3-1 | R-1 | 95 | 34 | 13.2 | 4.4 | 3.9 | Favorable |
| Example 3-2 | R-2 | 95 | 34 | 13.3 | 3.7 | 3.8 | Favorable |
| Example 3-3 | R-3 | 90 | 31 | 12.9 | 3.4 | 3.8 | Favorable |
| Example 3-4 | R-4 | 90 | 30 | 12.5 | 3.6 | 3.7 | Favorable |
| Example 3-5 | R-5 | 85 | 26 | 13.8 | 3.5 | 3.9 | Favorable |
| Example 3-6 | R-6 | 85 | 31 | 13.5 | 3.7 | 3.7 | Favorable |
| Example 3-7 | R-7 | 85 | 26 | 13.2 | 3.7 | 3.9 | Favorable |
| Example 3-8 | R-8 | 90 | 30 | 13.0 | 4.3 | 3.6 | Favorable |
| Example 3-9 | R-9 | 85 | 27 | 13.1 | 4.4 | 3.5 | Favorable |
| Example 3-10 | R-10 | 95 | 25 | 13.8 | 4.3 | 3.5 | Favorable |
| Example 3-11 | R-11 | 85 | 27 | 13.7 | 3.6 | 3.7 | Favorable |
| Example 3-12 | R-12 | 85 | 27 | 13.5 | 3.8 | 3.8 | Favorable |
| Comparative Example 3-1 | R-13 | 90 | 32 | 10.8 | 4.5 | 4.5 | Favorable |
| Comparative Example 3-2 | R-14 | 90 | 29 | 10.6 | 4.7 | 4.6 | Favorable |
| Comparative Example 3-3 | R-15 | 85 | 26 | 10.4 | 5.0 | 4.7 | Favorable |
| Comparative Example 3-4 | R-16 | 85 | 29 | 11.0 | 4.8 | 4.6 | Favorable |
| Comparative Example 3-5 | R-17 | 85 | 29 | 10.8 | 4.4 | 4.5 | Favorable |
| Comparative Example 3-6 | R-18 | 85 | 31 | 10.3 | 4.4 | 4.8 | Favorable |
| Comparative Example 3-7 | R-19 | 85 | 26 | 10.2 | 5.0 | 4.9 | Favorable |
| Comparative Example 3-8 | R-20 | 85 | 26 | 9.9 | 4.9 | 5.0 | unfavorable |

The results in Table 7 found the resist composition of the present invention demonstrates favorable lithography performance such as EL, MEF, and LWR in negative patterning by organic solvent development, as well as effective defect reduction. It was thus found that the resist composition of the present invention is effective in development process of an organic solvent.

[Examples 4-1 to 4-12, Comparative Examples 4-1 to 4-8] PTD; ArF Exposure Patterning Evaluation (3); Line and Space Evaluation The resist compositions of the present invention (R-1 to 12) prepared by the compositions according to the above Tables 4 and 5 and resist compositions (R-13 to 20) for Comparative Example were spin-coated on a substrate for try layer process obtained by coating a spin-on carbon film ODL-101 (Product from Shin-Etsu Chemical Co., Ltd.) 200 nm in thickness, and a silicon-containing spin-on hard mask SHB-A940 (silicon content: 43% by mass) 35 nm in thickness thereon, baked at 100° C. for 60 seconds using a hot plate to form resist film 100 nm in thickness.

The product was subjected to pattern exposure using ArF immersion excimer laser scanner (Product from Nikon Corporation, NSR-610C, NA 1.30, σ 0.98/0.78, 4/5 annular illumination), and a 6% halftone phase shift mask with a pitch of 100 nm and a space width of 50 nm (on-wafer size) for post-exposure 60-second heat treatment (post-exposure baking: PEB). Thereafter, a 2.38% tetramethylammonium-hydroxide aqueous solution was discharged from a development nozzle by rotation for 3 seconds at 30 rpm and subjected to stationary puddle development for 27 seconds. Consequently, line and space pattern (LS pattern) where an exposed area is dissolved into a developer was obtained with a space width of 50 nm and a pitch of 100 nm.

[Sensitivity Evaluation]

The LS obtained pattern was observed with electron microscope, and the optimum exposure dose (Eop, mJ/cm$^2$) for obtaining a LS pattern with a space width of 50 nm and a pitch of 100 nm was determined.

[Exposure Latitude (EL) Evaluation]

In exposure latitude evaluation, the exposure latitude (unit: %) was determined from an exposure dose which provided a LS pattern with a hole diameter of 50 nm±10% (45 nm to 55 nm), according to the following formula.

Exposure latitude (%)=(|E1−E2|/Eop)×100

E1: Optimum exposure dose providing LS pattern with a space width of 45 nm and a pitch of 100 nm
E2: Optimum exposure dose providing LS pattern with a space width of 55 nm and a pitch of 100 nm
Eop: Optimum exposure dose providing LS pattern with a space width of 50 nm and a pitch of 100 nm

[Mask Error Factor (MEF) Evaluation]

The mask pitch was fixed, and the mask line width was changed, and the films were irradiated with the optimum exposure dose in the above sensitivity evaluation to form patterns. From the changes in mask line width and pattern space width, MET values were determined according to the following formula. The performance is favorable as the value approaches 1.

MEF=(pattern space width/mask line width)−b b: constant

[Line Width Roughness (LWR) Evaluation]

The LS pattern obtained by irradiating films with the optimum exposure dose was subjected to dimensional measurement at 10 portions in the longitudinal direction of space width with using TOSEM (S-9380, Product from Hitachi High-Technologies Corporation). The resulting standard deviation (σ) was multiplied by three (3σ) to be defined as a LWR. As the 3σ value is small, a pattern with small roughness and uniform space width can be obtained.

[Defect Density Evaluation]

The number of defects in a pattern formed after development was examined by a defect inspection system KLA2800 (Product from KLA-Tencor) to determine the defect density according to the following formula.

Defect density (number/cm$^2$)=total number of detected defects/inspected area

Formed pattern: 50 nm 1:1 line and space's repeated pattern
Defect inspection condition: light source UV, inspected pixel size 0.241m, cell to cell mode
In this evaluation, "favorable" is under 0.05/cm$^2$, and "unfavorable" is 0.05/cm$^2$ or more.

Table 8 shows the results of the evaluations.

TABLE 8

| | Resist | PEB (° C.) | Eop (mJ/cm$^2$) | EL (%) | MEF | LWR (nm) | Defect Density (number/cm$^2$) |
|---|---|---|---|---|---|---|---|
| Example 4-1 | R-1 | 95 | 33 | 14.4 | 4.0 | 3.8 | Favorable |
| Example 4-2 | R-2 | 95 | 34 | 14.3 | 3.1 | 3.7 | Favorable |
| Example 4-3 | R-3 | 90 | 32 | 14.0 | 3.2 | 3.8 | Favorable |
| Example 4-4 | R-4 | 90 | 29 | 14.8 | 3.3 | 3.5 | Favorable |
| Example 4-5 | R-5 | 85 | 28 | 14.2 | 3.0 | 3.6 | Favorable |
| Example 4-6 | R-6 | 85 | 31 | 14.3 | 3.1 | 3.8 | Favorable |
| Example 4-7 | R-7 | 85 | 27 | 14.5 | 3.4 | 3.8 | Favorable |
| Example 4-8 | R-8 | 90 | 29 | 14.0 | 4.2 | 3.4 | Favorable |
| Example 4-9 | R-9 | 85 | 26 | 14.1 | 4.0 | 3.6 | Favorable |
| Example 4-10 | R-10 | 95 | 27 | 14.2 | 4.1 | 3.3 | Favorable |
| Example 4-11 | R-11 | 85 | 28 | 14.3 | 3.4 | 3.5 | Favorable |
| Example 4-12 | R-12 | 85 | 28 | 13.9 | 3.2 | 3.6 | Favorable |
| Comparative Example 4-1 | R-13 | 90 | 32 | 11.5 | 4.1 | 4.3 | Favorable |
| Comparative Example 4-2 | R-14 | 90 | 29 | 11.2 | 4.2 | 4.5 | Favorable |
| Comparative Example 4-3 | R-15 | 85 | 29 | 11.4 | 4.5 | 4.7 | Favorable |
| Comparative Example 4-4 | R-16 | 85 | 29 | 11.8 | 4.4 | 4.5 | Favorable |
| Comparative Example 4-5 | R-17 | 85 | 25 | 11.9 | 4.3 | 4.6 | Favorable |
| Comparative Example 4-6 | R-18 | 85 | 31 | 11.3 | 4.4 | 4.7 | Favorable |
| Comparative Example 4-7 | R-19 | 85 | 23 | 10.9 | 4.7 | 4.9 | Favorable |
| Comparative Example 4-8 | R-20 | 85 | 26 | 10.8 | 4.9 | 5.0 | unfavorable |

The results in Table 8 found the resist composition of the present invention demonstrates favorable lithography performance such as sensitivity, EL, MEF, and CDU in positive pattern by alkaline development, as well as effective defect reduction. It was thus found that the resist composition of the present invention is effective in alkaline development process.

It must be stated here that the present invention is not restricted to the embodiments shown by Examples. The embodiments shown by Examples are merely examples so that any embodiments composed of substantially the same technical concept as disclosed in the claims of the present invention and expressing a similar effect are included in the technical scope of the present invention.

EXPLANATIONS OF LETTERS OR NUMERALS

10 . . . Substrate, 20 . . . Layer to be processed, 30 . . . Intermediate interposed layer, 40 . . . Resist film, 50 . . . Light

What is claimed is:

1. A sulfonium salt comprising an anion and a cation, the cation having a partial structure represented by the following general formula (1),

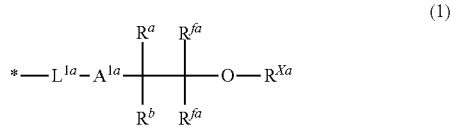

(1)

where each of $R^{fa}$ and $R^{fb}$ independently represents a fluoroalkyl group having 1 to 4 carbon atoms; $R^{Xa}$ represents a hydrogen atom or an acid labile group; each of $R^a$ and $R^b$ independently represents a hydrogen atom, or a monovalent hydrocarbon group having 1 to 10 carbon atoms optionally containing a heteroatom, $R^a$ and $R^b$ may be bonded to form a ring together with a carbon atom bonded thereto; $A^{1a}$ represents an ether bond or a thioether bond; $L^{1a}$ represents a single bond, or a divalent linking group having 1 to 20 carbon atoms optionally containing a heteroatom; "*" represents a bond; wherein
  the sulfonium salt has one sulfonium cation per molecule, and
  the sulfonium salt doesn't correspond to a sulfonium salt having a cation represented by the following general formula (1'),

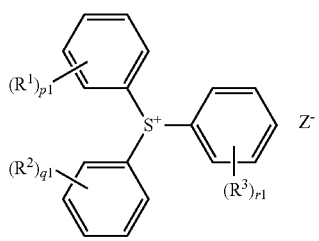

(1')

where $R^{fa}$ and $R^{fb}$ represent the same meanings as before.

2. The sulfonium salt according to claim 1, wherein the sulfonium salt is represented by the following general formula (2),

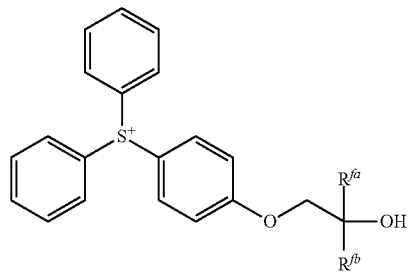

(2)

wherein, each of $R^1$, $R^2$, and $R^3$ independently represents any of a hydrogen atom, a partial structure represented by the general formula (1), a linear, a branched, or a cyclic monovalent hydrocarbon group having 1 to 20 carbon atoms optionally containing a heteroatom, or direct binding with an adjacent benzene ring; each of "p1", "q1", and "r1" independently represents an integer of 0 to 5, and when "p1", "q1", or "r1" represents 2 or more, a plurality of $R^1$s, $R^2$s, or $R^3$s corresponding thereto may be the same or different, when p1+q1+r1 represents 2 or more, a plurality of $R^1$s, $R^2$s, or $R^3$s may be bonded to form a ring together with a carbon atom on a benzene ring bonded thereto, and $R^1$ and $R^2$, $R^1$ and $R^3$, or $R^2$ and $R^3$ may be bonded to form a ring together with two benzene rings bonded thereto and a sulfur atom in the formula; one or more of $R^1$, $R^2$, and $R^3$ represent a partial structure represented by the general formula (1), "*" in the general formula (1) represents a bond with a benzene ring; and $Z^-$ represents a monovalent anion.

3. The sulfonium salt according to claim 1, wherein $R^{Xa}$ in the general formula (1) represents an acid labile group.

4. The sulfonium salt according to claim 1, wherein $R^{fa}$ and $R^{fb}$ in the general formula (1) represent a trifluoromethyl group; and $R^a$ and $R^b$ represent a hydrogen atom.

5. The sulfonium salt according to claim 1, wherein $L^{1a}$ in the general formula (1) represents a single bond.

6. The sulfonium salt according to claim 1, wherein $A^{1a}$ in the general formula (1) represents an ether bond.

7. The sulfonium salt according to claim 1, wherein the anion is represented by the following general formula (3),

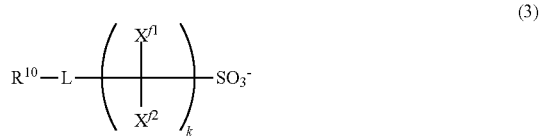

(3)

wherein, $R^{10}$ represents a linear, a branched, or a cyclic monovalent hydrocarbon group having 1 to 40 carbon atoms optionally containing a heteroatom; "L" represents a single bond or a divalent linking group; each of $X^{f1}$ and $X^{f2}$ independently represents a hydrogen atom, a fluorine atom, or an alkyl group substituted by one or more fluorine atoms; and "k" represents an integer of 0 to 4.

8. The sulfonium salt according to claim 1, wherein the anion is represented by the following general formula (4a), (4b), or (4c),

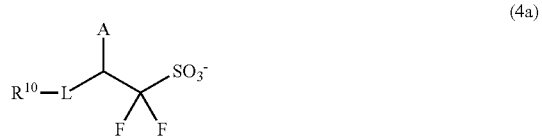

(4a)

(4b)

(4c)

wherein, $R^{10}$ represents a linear, a branched, or a cyclic monovalent hydrocarbon group having 1 to 40 carbon atoms optionally containing a heteroatom; "L" represents a single bond or a divalent linking group; "A" represents a hydrogen atom or a trifluoromethyl group; and "s" represents an integer of 0 to 5.

9. A resist composition comprising:
  (A) the sulfonium salt according to claim 1;
  (B) a base resin; and
  (C) an organic solvent.

10. The resist composition according to claim 9, further comprising one or more selected from:

(D) a photo acid generator other than the component (A);
(E) a quencher; and
(F) a surfactant.

11. The resist composition according to claim 10, wherein the component (D) is represented by the following general formula (8) or the following general formula (9),

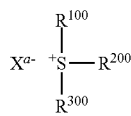

(8)

wherein, each of $R^{100}$, $R^{200}$, and $R^{300}$ independently represents a linear, a branched, or a cyclic monovalent hydrocarbon group having 1 to 20 carbon atoms optionally containing a heteroatom, and two or more of R100, $R^{200}$ and $R^{300}$ may be bonded to form a ring together with a sulfur atom in the formula; and $X^{a-}$ represents an anion represented by any of the following general formula (8A), (8B), (8C) or (8D),

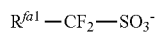

(8A)

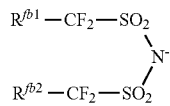

(8B)

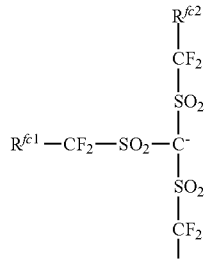

(8C)

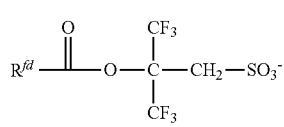

(8D)

wherein, each of $R^{fa1}$, $R^{fb1}$, $R^{fb2}$, $R^{fc1}$, $R^{fc2}$ and $R^{fc3}$ independently represents a fluorine atom, or a linear, a branched, or a cyclic monovalent hydrocarbon group having 1 to 40 carbon atoms optionally containing a heteroatom; $R^{fb1}$ and $R^{fb2}$, and $R^{fc1}$ and $R^{fc2}$ may be bonded to form a ring together with a carbon atom bonded thereto and an atom therebetween; and $R^{fd}$ represents a linear, a branched, or a cyclic monovalent hydrocarbon group having 1 to 40 carbon atoms optionally containing a heteroatom,

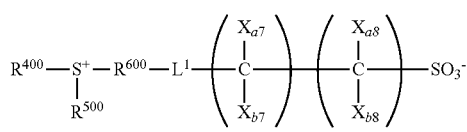

(9)

wherein, each of $R^{400}$ and $R^{500}$ independently represents a linear, a branched, or a cyclic monovalent hydrocarbon group having 1 to 30 carbon atoms optionally containing a heteroatom; $R^{600}$ represents a linear, a branched, or a cyclic divalent hydrocarbon group having 1 to 30 carbon atoms optionally containing a heteroatom; two or more of $R^{400}$, $R^{500}$, and $R^{600}$ may be bonded to form a ring together with a sulfur atom in the formula; $L^1$ represents a single bond, an ether bond, or a linear, a branched, or a cyclic divalent hydrocarbon group having 1 to 20 carbon atoms optionally containing a heteroatom; each of $X_{a7}$, $X_{b7}$, $X_{a8}$, and $X_{b8}$ independently represents any of a hydrogen atom, a fluorine atom, or a trifluoromethyl group; one or more of $X_{a7}$, $X_{b7}$, $X_{a8}$, and $X_{b8}$ represent a fluorine atom or a trifluoromethyl group.

12. The resist composition according to claim 10, wherein the component (E) comprises an amine compound or a compound represented by the following general formula (10) or the following general formula (11),

(10)

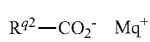

(11)

wherein, $R^{q1}$ represents a hydrogen atom, or a linear, a branched, or a cyclic monovalent hydrocarbon group having 1 to 40 carbon atoms optionally containing a heteroatom; except for cases where a hydrogen atom on a carbon atom at a-position of a sulfo group is substituted by a fluorine atom or a fluoroalkyl group when $R^{q1}$ represents a monovalent hydrocarbon group; $R^{q2}$ represents a hydrogen atom, or a linear, a branched, or a cyclic monovalent hydrocarbon group having 1 to 40 carbon atoms optionally containing a heteroatom; and Mq⁺ represents an onium cation.

13. The resist composition according to claim 10, wherein the component (F) is a surfactant that is insoluble or poorly soluble in water and soluble in an alkaline developer, or a surfactant that is insoluble or poorly soluble in water and an alkaline developer.

14. The resist composition according to claim 9, wherein the component (B) is a polymer comprising a repeating unit represented by the following general formula (6) and a repeating unit represented by the following general formula (7),

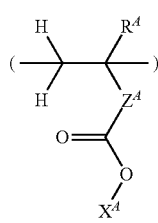

(6)

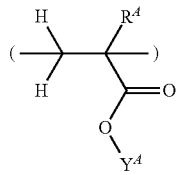

(7)

wherein, $R^A$ represents any of a hydrogen atom, a fluorine atom, a methyl group, or a trifluoromethyl group; $Z^A$ represents any of a single bond, a phenylene group, a naphthylene group, or a (main chain)-C(=O)—O—Z'—; Z' represents a linear, a branched, or a cyclic alkylene group having 1 to 10 carbon atoms optionally containing any of a hydroxy group, an ether bond, an ester bond, or a lactone ring, a phenylene group, or a naphthylene group; $X^A$ represents an acid labile group; and $Y^A$ represents a hydrogen atom, or a polar group having one or more structures selected from a hydroxy group, a cyano group, a carbonyl group, a carboxyl group, an ether bond, an ester bond, a sulfonic ester bond, a carbonate bond, a lactone ring, a sultone ring, and a carboxylic acid anhydride.

15. The resist composition according to claim 14, wherein $X^A$ in the general formula (6) is represented by any of the following general formula (6a), (6b), or (6c),

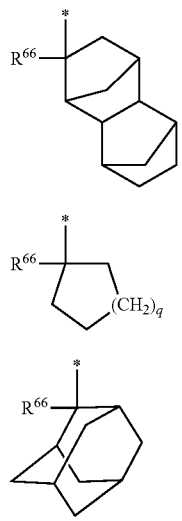

wherein, $R^{66}$ represents a linear, a branched, or a cyclic monovalent hydrocarbon group having 1 to 10 carbon atoms optionally containing a heteroatom; "q" represents 1 or 2; and "*" represents a bond with an ester site in the general formula (6).

16. The resist composition according to claim 14, wherein $Z^A$ in the general formula (6) represents a single bond.

17. The resist composition according to claim 9, wherein the resist composition is a chemically amplified resist composition.

18. A patterning process comprising:
applying the resist composition according to claim 9 to a substrate;
exposing the composition with any of a high energy beam with a wavelength of 140 to 250 nm, an electron beam, or EUV via a photo mask after heating the composition before exposure; and
developing the composition with a developer after heating the composition after exposure.

19. The patterning process according to claim 18, wherein an alkaline aqueous solution is used as the developer to obtain a positive pattern wherein an exposed area is dissolved and a non-exposed area is not dissolved.

20. The patterning process according to claim 18, wherein an organic solvent is used as the developer to obtain a negative pattern wherein a non-exposed area is dissolved and an exposed area is not dissolved.

21. The patterning process according to claim 20, wherein the developer comprises one or more of organic solvents selected from the group consisting of 2-octanone, 2-nonanone, 2-heptanone, 3-heptanone, 4-heptanone, 2-hexanone, 3-hexanone, disobutyl ketone, methyl cyclohexanone, acetophenone, methylacetophenone, propyl acetate, butyl acetate, isobutyl acetate, amyl acetate, butenyl acetate, isoamyl acetate, propyl formate, butyl formate, isobutyl formate, amyl formate, isoamyl formate, methyl valerate, methyl pentenoate, methyl crotonate, ethyl crotonate, methyl propionate, ethyl propionate, ethyl 3-ethoxy propionate, methyl lactate, ethyl lactate, propyl lactate, butyl lactate, isobuthyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate.

22. The patterning process according to claim 18, wherein in the step of exposure, a liquid with a refractive index of 1.0 or more is mediated between an applied resist film and a projection lens for liquid immersion exposure.

23. The patterning process according to claim 22, wherein a top coat is further formed on the applied resist film, and the liquid is mediated between the top coat and the projection lens for liquid immersion exposure.

* * * * *